US010966876B2

(12) United States Patent
Lenser et al.

(10) Patent No.: US 10,966,876 B2
(45) Date of Patent: *Apr. 6, 2021

(54) METHODS AND APPARATUSES FOR ASSEMBLING ELASTIC LAMINATES WITH DIFFERENT BOND DENSITIES FOR ABSORBENT ARTICLES

(71) Applicant: The Procter & Gamble Company, Cincinnati, OH (US)

(72) Inventors: Todd Douglas Lenser, Liberty Township, OH (US); Urmish Popatlal Dalal, Milford, OH (US); Uwe Schneider, Cincinnati, OH (US); Todd Joseph Statt, Kings Mills, OH (US); Joerg Mueller, Alte Haingasse (DE); Melanie Acevedo, Springfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/748,885

(22) Filed: Jan. 22, 2020

(65) Prior Publication Data

US 2020/0170846 A1    Jun. 4, 2020

Related U.S. Application Data

(63) Continuation of application No. 15/674,596, filed on Aug. 11, 2017, now Pat. No. 10,575,993.
(Continued)

(51) Int. Cl.
*B32B 37/00* (2006.01)
*A61F 13/15* (2006.01)
(Continued)

(52) U.S. Cl.
CPC .. *A61F 13/15699* (2013.01); *A61F 13/15593* (2013.01); *A61F 13/15601* (2013.01);
(Continued)

(58) Field of Classification Search
USPC ........................................................ 156/73.1
See application file for complete search history.

(56) References Cited

U.S. PATENT DOCUMENTS 3,113,225 A    12/1963   Kleesattel et al.
3,338,992 A    8/1967    Kinney
(Continued)

FOREIGN PATENT DOCUMENTS

CN    103434239 B    11/2015
CN    104837455 B    4/2018
(Continued)

OTHER PUBLICATIONS

PCT International Search Report and Written Opinion, dated Sep. 25, 2017, 16 pages.
(Continued)

*Primary Examiner* — James D Sells
(74) *Attorney, Agent, or Firm* — Wednesday G. Shipp

(57) ABSTRACT

The methods herein relate to assembling an elastic laminate with a first elastic material and a second elastic material bonded between first and second substrates. During assembly, an elastic laminate may be formed by positioning the first and second substrates in contact with stretched central regions of the first and second elastic materials. The elastic laminates may include two or more bonding regions that may be defined by the various layers or components of the elastic laminate that are laminated or stacked relative to each other. In some configurations, a first plurality of ultrasonic bonds are applied to the elastic laminate to define a first bond density in the first bonding region, and a second plurality of
(Continued)

ultrasonic bonds are applied to the elastic laminate to define a second bond density in the second bonding region, wherein the second bond density is not equal to the first bond density.

16 Claims, 29 Drawing Sheets

Related U.S. Application Data

(60) Provisional application No. 62/419,515, filed on Nov. 9, 2016, provisional application No. 62/406,025, filed on Oct. 10, 2016, provisional application No. 62/374,010, filed on Aug. 12, 2016.

(51) Int. Cl.

| | | |
|---|---|---|
| *B32B 7/05* | (2019.01) | |
| *A61F 13/49* | (2006.01) | |
| *B29C 55/02* | (2006.01) | |
| *B29C 65/74* | (2006.01) | |
| *B29C 65/00* | (2006.01) | |
| *B32B 5/02* | (2006.01) | |
| *B32B 37/10* | (2006.01) | |
| *B32B 37/14* | (2006.01) | |
| *B32B 38/00* | (2006.01) | |
| *B29C 65/08* | (2006.01) | |
| *B32B 27/12* | (2006.01) | |
| *B32B 15/09* | (2006.01) | |
| *B32B 27/30* | (2006.01) | |
| *B29C 65/78* | (2006.01) | |
| *B32B 7/04* | (2019.01) | |
| *B32B 27/06* | (2006.01) | |
| *B32B 27/40* | (2006.01) | |
| *B32B 5/22* | (2006.01) | |
| *B32B 27/34* | (2006.01) | |
| *B32B 15/088* | (2006.01) | |
| *B32B 27/28* | (2006.01) | |
| *B32B 15/095* | (2006.01) | |
| *B32B 15/14* | (2006.01) | |
| *B32B 15/082* | (2006.01) | |
| *B32B 15/04* | (2006.01) | |
| *B32B 5/26* | (2006.01) | |
| *B29C 55/08* | (2006.01) | |
| *B32B 3/08* | (2006.01) | |
| *B32B 15/08* | (2006.01) | |
| *B32B 37/20* | (2006.01) | |
| *B32B 38/18* | (2006.01) | |
| *B32B 15/06* | (2006.01) | |
| *B32B 25/14* | (2006.01) | |
| *B32B 27/36* | (2006.01) | |
| *B32B 27/08* | (2006.01) | |
| *B29K 21/00* | (2006.01) | |
| *B29L 9/00* | (2006.01) | |
| *B29L 31/48* | (2006.01) | |

(52) U.S. Cl.
CPC .. *A61F 13/15609* (2013.01); *A61F 13/15674* (2013.01); *A61F 13/15723* (2013.01); *A61F 13/15731* (2013.01); *A61F 13/15739* (2013.01); *A61F 13/15764* (2013.01); *A61F 13/49009* (2013.01); *A61F 13/49012* (2013.01); *A61F 13/49019* (2013.01); *B29C 55/02* (2013.01); *B29C 65/08* (2013.01); *B29C 65/74* (2013.01); *B29C 66/00145* (2013.01); *B29C 66/43* (2013.01); *B32B 5/022* (2013.01); *B32B 7/05* (2019.01); *B32B 27/12* (2013.01); *B32B 37/1018* (2013.01); *B32B 37/14* (2013.01); *B32B 38/0012* (2013.01); *A61F 2013/15715* (2013.01); *A61F 2013/15869* (2013.01); *A61F 2013/15926* (2013.01); *A61F 2013/49093* (2013.01); *B29C 55/08* (2013.01); *B29C 65/086* (2013.01); *B29C 65/7847* (2013.01); *B29C 66/1122* (2013.01); *B29C 66/21* (2013.01); *B29C 66/344* (2013.01); *B29C 66/433* (2013.01); *B29C 66/723* (2013.01); *B29C 66/7294* (2013.01); *B29C 66/81469* (2013.01); *B29C 66/83411* (2013.01); *B29C 66/83415* (2013.01); *B29K 2021/003* (2013.01); *B29K 2995/0046* (2013.01); *B29L 2009/00* (2013.01); *B29L 2031/4878* (2013.01); *B32B 3/08* (2013.01); *B32B 5/22* (2013.01); *B32B 5/26* (2013.01); *B32B 7/04* (2013.01); *B32B 15/04* (2013.01); *B32B 15/043* (2013.01); *B32B 15/06* (2013.01); *B32B 15/08* (2013.01); *B32B 15/082* (2013.01); *B32B 15/088* (2013.01); *B32B 15/09* (2013.01); *B32B 15/095* (2013.01); *B32B 15/14* (2013.01); *B32B 25/14* (2013.01); *B32B 27/06* (2013.01); *B32B 27/08* (2013.01); *B32B 27/285* (2013.01); *B32B 27/302* (2013.01); *B32B 27/34* (2013.01); *B32B 27/36* (2013.01); *B32B 27/40* (2013.01); *B32B 37/144* (2013.01); *B32B 37/20* (2013.01); *B32B 38/1858* (2013.01); *B32B 2038/0028* (2013.01); *B32B 2262/0207* (2013.01); *B32B 2262/14* (2013.01); *B32B 2270/00* (2013.01); *B32B 2274/00* (2013.01); *B32B 2307/51* (2013.01); *B32B 2307/718* (2013.01); *B32B 2307/732* (2013.01); *B32B 2555/02* (2013.01); *B32B 2556/00* (2013.01)

(56) References Cited

U.S. PATENT DOCUMENTS

| | | |
|---|---|---|
| 3,562,041 A | 2/1971 | Robertson |
| 3,566,726 A | 3/1971 | Politis |
| 3,692,613 A | 9/1972 | Pederson |
| 3,733,238 A | 5/1973 | Long et al. |
| 3,802,817 A | 4/1974 | Matsuki |
| 3,848,594 A | 11/1974 | Buell |
| 3,849,241 A | 11/1974 | Butin |
| 3,860,003 A | 1/1975 | Buell |
| 3,911,173 A | 10/1975 | Sprague, Jr. |
| 3,929,135 A | 12/1975 | Thompson |
| 4,116,892 A | 9/1978 | Schwarz |
| 4,324,314 A | 4/1982 | Beach et al. |
| 4,405,297 A | 9/1983 | Appel |
| 4,463,045 A | 7/1984 | Ahr et al. |
| 4,573,986 A | 3/1986 | Minetola et al. |
| 4,610,678 A | 9/1986 | Weisman |
| 4,629,643 A | 12/1986 | Curro et al. |
| 4,634,440 A | 1/1987 | Widlund |
| 4,662,875 A | 5/1987 | Hirotsu |
| 4,673,402 A | 6/1987 | Weisman |
| 4,780,352 A | 10/1988 | Palumbo |
| 4,785,996 A | 11/1988 | Ziecker et al. |
| 4,834,735 A | 5/1989 | Alemany |
| 4,834,741 A | 5/1989 | Sabee |
| 4,842,666 A | 6/1989 | Lverenicz |
| 4,846,815 A | 7/1989 | Scripps |
| 4,854,984 A | 8/1989 | Ball |
| 4,888,231 A | 12/1989 | Angstadt |
| 4,892,536 A | 1/1990 | DesMarais et al. |
| 4,894,060 A | 1/1990 | Nestegard |
| 4,919,738 A | 4/1990 | Ball et al. |
| 4,940,464 A | 7/1990 | Van Gompel et al. |
| 4,946,527 A | 8/1990 | Battrell |
| 4,990,147 A | 2/1991 | Freeland |

(56) References Cited

U.S. PATENT DOCUMENTS

| | | |
|---|---|---|
| 5,006,394 A | 4/1991 | Baird |
| 5,037,416 A | 8/1991 | Allen et al. |
| 5,092,861 A | 3/1992 | Nomura et al. |
| 5,137,537 A | 8/1992 | Herron |
| 5,143,679 A | 9/1992 | Weber et al. |
| 5,147,345 A | 9/1992 | Lavon |
| 5,149,720 A | 9/1992 | Desmarais |
| 5,151,092 A | 9/1992 | Buell |
| 5,156,793 A | 10/1992 | Buell et al. |
| 5,167,897 A | 12/1992 | Weber et al. |
| 5,221,274 A | 6/1993 | Buell |
| 5,242,436 A | 9/1993 | Weil |
| 5,246,433 A | 9/1993 | Hasse et al. |
| 5,260,345 A | 11/1993 | Desmarais |
| 5,266,392 A | 11/1993 | Land |
| 5,269,775 A | 12/1993 | Freeland et al. |
| 5,342,338 A | 8/1994 | Roe |
| 5,360,420 A | 11/1994 | Cook et al. |
| 5,382,400 A | 1/1995 | Pike |
| 5,387,207 A | 2/1995 | Dyer |
| 5,397,316 A | 3/1995 | Young |
| 5,418,045 A | 5/1995 | Pike |
| 5,422,172 A | 6/1995 | Wu |
| 5,433,715 A | 7/1995 | Tanzer et al. |
| 5,518,801 A | 5/1996 | Chappell et al. |
| 5,554,145 A | 9/1996 | Roe |
| 5,569,234 A | 10/1996 | Buell et al. |
| 5,571,096 A | 11/1996 | Dobrin |
| 5,580,411 A | 12/1996 | Nease |
| 5,591,155 A | 1/1997 | Nishikawa |
| 5,599,335 A | 2/1997 | Goldman et al. |
| 5,607,414 A | 3/1997 | Richards et al. |
| 5,607,760 A | 3/1997 | Roe |
| 5,609,587 A | 3/1997 | Roe |
| 5,622,772 A | 4/1997 | Stokes |
| 5,628,097 A | 5/1997 | Benson et al. |
| 5,635,191 A | 6/1997 | Roe et al. |
| 5,643,588 A | 7/1997 | Roe et al. |
| 5,658,639 A | 8/1997 | Curro et al. |
| 5,665,300 A | 9/1997 | Brignola |
| 5,674,216 A | 10/1997 | Buell et al. |
| 5,700,254 A | 12/1997 | McDowall et al. |
| 5,702,551 A | 12/1997 | Huber et al. |
| 5,707,468 A | 1/1998 | Arnold |
| 5,817,199 A | 10/1998 | Brennecke et al. |
| 5,827,909 A | 10/1998 | Desmarais |
| 5,865,823 A | 2/1999 | Curro |
| 5,897,545 A | 4/1999 | Kline et al. |
| 5,916,661 A | 6/1999 | Benson et al. |
| 5,957,908 A | 9/1999 | Kline et al. |
| 5,968,025 A | 10/1999 | Roe et al. |
| 5,972,806 A | 10/1999 | Weinberger |
| 5,993,432 A | 11/1999 | Lodge et al. |
| 6,004,306 A | 12/1999 | Robles |
| 6,030,373 A | 2/2000 | Vangompel |
| 6,036,796 A | 3/2000 | Halbert et al. |
| 6,096,668 A | 8/2000 | Abuto |
| 6,107,537 A | 8/2000 | Elder et al. |
| 6,118,041 A | 9/2000 | Roe et al. |
| 6,120,487 A | 9/2000 | Ashton |
| 6,120,489 A | 9/2000 | Johnson et al. |
| 6,123,792 A | 9/2000 | Samida |
| 6,140,551 A | 10/2000 | Niemeyer |
| 6,153,209 A | 11/2000 | Vega et al. |
| 6,169,151 B1 | 1/2001 | Waymouth |
| 6,255,236 B1 | 7/2001 | Cree |
| 6,369,121 B1 | 4/2002 | Catalfamo |
| 6,410,129 B2 | 6/2002 | Zhang et al. |
| 6,426,444 B2 | 7/2002 | Roe |
| 6,432,098 B1 | 8/2002 | Kline et al. |
| 6,454,989 B1 | 9/2002 | Neely |
| 6,458,447 B1 | 10/2002 | Cabell |
| 6,465,073 B1 | 10/2002 | Morman |
| 6,472,045 B1 | 10/2002 | Morman |
| 6,472,084 B1 | 10/2002 | Middlesworth et al. |
| 6,475,600 B1 | 11/2002 | Morman |
| 6,498,284 B1 | 12/2002 | Roe |
| 6,508,641 B1 | 1/2003 | Kubik |
| 6,513,221 B2 | 2/2003 | Vogt |
| 6,518,378 B2 | 2/2003 | Waymouth |
| 6,534,149 B1 | 3/2003 | Daley et al. |
| 6,540,854 B2 | 4/2003 | Couillard |
| 6,555,643 B1 | 4/2003 | Rieger |
| 6,559,262 B1 | 5/2003 | Waymouth |
| 6,572,595 B1 | 6/2003 | Klemp et al. |
| 6,572,598 B1 | 6/2003 | Ashton |
| 6,586,652 B1 | 7/2003 | Roe et al. |
| 6,610,390 B1 | 8/2003 | Kauschke |
| 6,617,016 B2 | 9/2003 | Zhang et al. |
| 6,627,564 B1 | 9/2003 | Morman |
| 6,627,787 B1 | 9/2003 | Roe et al. |
| 6,632,386 B2 | 10/2003 | Shelley |
| 6,645,330 B2 | 11/2003 | Pargass et al. |
| 6,645,569 B2 | 11/2003 | Cramer et al. |
| 6,649,001 B2 | 11/2003 | Heden |
| 6,677,258 B2 | 1/2004 | Carroll et al. |
| 6,692,477 B2 | 2/2004 | Gibbs |
| 6,713,159 B1 | 3/2004 | Blenke et al. |
| 6,758,925 B1 | 7/2004 | Stegelmann |
| 6,767,420 B2 | 7/2004 | Stegelmann |
| 6,825,393 B2 | 11/2004 | Roe et al. |
| 6,830,800 B2 | 12/2004 | Curro |
| 6,843,134 B2 | 1/2005 | Anderson et al. |
| 6,861,571 B1 | 3/2005 | Roe et al. |
| 6,863,933 B2 | 3/2005 | Cramer et al. |
| 6,878,433 B2 | 4/2005 | Curro |
| 6,974,514 B2 | 12/2005 | Hamulski |
| 7,056,404 B2 | 6/2006 | McFall et al. |
| 7,062,983 B2 | 6/2006 | Anderson et al. |
| 7,108,759 B2 | 9/2006 | You |
| 7,112,621 B2 | 9/2006 | Rohrbaugh et al. |
| 7,270,861 B2 | 9/2007 | Broering |
| 7,291,239 B2 | 11/2007 | Polanco |
| 7,435,243 B2 | 10/2008 | Miyamoto |
| 7,531,233 B2 | 5/2009 | Kling |
| 7,569,039 B2 | 8/2009 | Matsuda et al. |
| 7,572,249 B2 | 8/2009 | Betts |
| 7,582,075 B2 | 9/2009 | Betts |
| 7,625,363 B2 | 12/2009 | Yoshimasa |
| 7,741,235 B2 | 6/2010 | Hashimoto |
| 7,803,244 B2 | 9/2010 | Siqueira |
| 7,806,883 B2 | 10/2010 | Fossum et al. |
| 7,819,853 B2 | 10/2010 | Desai et al. |
| 7,824,594 B2 | 11/2010 | Qureshi et al. |
| 7,870,651 B2 | 1/2011 | Middlesworth |
| 7,896,641 B2 | 3/2011 | Qureshi et al. |
| 7,917,985 B2 | 4/2011 | Dorsey |
| 7,931,632 B2 | 4/2011 | Betts |
| 7,954,213 B2 | 6/2011 | Mizutani |
| 7,998,127 B2 | 8/2011 | Betts |
| 8,062,279 B2 | 11/2011 | Miyamoto |
| 8,062,572 B2 | 11/2011 | Qureshi et al. |
| 8,092,438 B2 | 1/2012 | Betts |
| 8,118,801 B2 | 2/2012 | Macura et al. |
| 8,158,043 B2 | 4/2012 | Gibson |
| 8,172,971 B2 | 5/2012 | Yamamoto |
| 8,186,296 B2 | 5/2012 | Brown et al. |
| 8,361,913 B2 | 1/2013 | Siqueira |
| 8,450,557 B2 | 5/2013 | Nishitani |
| 8,454,571 B2 | 6/2013 | Rezai |
| 8,480,642 B2 | 7/2013 | Betts |
| 8,491,557 B2 | 7/2013 | Kline |
| 8,491,742 B2 | 7/2013 | Waas |
| 8,496,775 B2 | 7/2013 | Deng |
| 8,502,013 B2 | 8/2013 | Zhao |
| 8,518,004 B2 | 8/2013 | Betts |
| 8,585,666 B2 | 11/2013 | Weisman et al. |
| 8,618,350 B2 | 12/2013 | Mansfield |
| 8,679,391 B2 | 3/2014 | Odonnell |
| 8,690,852 B2 | 4/2014 | Macura |
| 8,697,938 B2 | 4/2014 | Roe |
| 8,709,579 B2 | 4/2014 | Hoenigmann |
| 8,726,051 B2 | 5/2014 | Lu |
| 8,741,083 B2 | 6/2014 | Wennerback |

(56) References Cited

U.S. PATENT DOCUMENTS

| | | |
|---|---|---|
| 8,776,856 B2 | 7/2014 | Yamamoto |
| 8,795,809 B2 | 8/2014 | Mansfield |
| 8,858,523 B2 | 10/2014 | Sauer |
| 8,939,957 B2 | 1/2015 | Raycheck et al. |
| 8,940,116 B2 | 1/2015 | Gilgenbach |
| 9,102,132 B2 | 8/2015 | Wennerbck |
| 9,211,221 B2 | 12/2015 | Macura |
| 9,301,889 B2 | 4/2016 | Miyamoto |
| 9,358,161 B2 | 6/2016 | Lawson et al. |
| 9,434,143 B2 | 9/2016 | Sablone |
| 9,498,941 B2 | 11/2016 | Sablone |
| 9,533,067 B2 | 1/2017 | Schonbeck |
| 9,687,580 B2 | 6/2017 | Schonbeck |
| 9,724,248 B2 | 8/2017 | Hughes |
| 9,821,542 B2 | 11/2017 | Bruce |
| 10,524,964 B2 | 1/2020 | Sauer |
| 10,568,775 B2 | 2/2020 | Lenser |
| 10,568,776 B2 | 2/2020 | Lenser |
| 10,575,993 B2 * | 3/2020 | Lenser .................... B29C 65/08 |
| 10,588,789 B2 | 3/2020 | Surushe |
| 10,617,573 B2 | 4/2020 | Koshijima |
| 2001/0018579 A1 | 8/2001 | Klemp |
| 2001/0024940 A1 | 9/2001 | Cook et al. |
| 2002/0095129 A1 | 7/2002 | Friderich |
| 2002/0188268 A1 | 12/2002 | Kline |
| 2003/0021951 A1 | 1/2003 | Desai |
| 2003/0105446 A1 | 6/2003 | Hutson |
| 2003/0109843 A1 | 6/2003 | Gibbs |
| 2003/0109844 A1 | 6/2003 | Gibbs |
| 2003/0120240 A1 | 6/2003 | Buell |
| 2003/0124310 A1 | 7/2003 | Ellis |
| 2003/0148684 A1 | 8/2003 | Cramer et al. |
| 2003/0233082 A1 | 12/2003 | Kline |
| 2004/0091693 A1 | 5/2004 | Thomas |
| 2004/0102125 A1 | 5/2004 | Morman |
| 2004/0112509 A1 | 6/2004 | Morman |
| 2004/0121690 A1 | 6/2004 | Mleziva |
| 2004/0182499 A1 | 9/2004 | Collier |
| 2004/0224132 A1 | 11/2004 | Roe |
| 2005/0008839 A1 | 1/2005 | Cramer et al. |
| 2005/0065487 A1 | 3/2005 | Graef |
| 2005/0107764 A1 | 5/2005 | Matsuda et al. |
| 2005/0154362 A1 | 7/2005 | Warren |
| 2005/0245162 A1 | 11/2005 | Mccormack |
| 2005/0287892 A1 | 12/2005 | Fouse |
| 2006/0062963 A1 | 3/2006 | Middlesworth |
| 2006/0135024 A1 | 6/2006 | Thomas |
| 2006/0148361 A1 | 7/2006 | Mccormack |
| 2006/0149209 A1 | 7/2006 | Malchow |
| 2006/0287637 A1 | 12/2006 | Lam |
| 2007/0105472 A1 | 5/2007 | Marche |
| 2007/0123124 A1 | 5/2007 | Middlesworth |
| 2007/0142798 A1 | 6/2007 | Goodlander et al. |
| 2007/0142806 A1 | 6/2007 | Roe et al. |
| 2007/0142825 A1 | 6/2007 | Prisco |
| 2007/0143972 A1 | 6/2007 | Kline |
| 2007/0202767 A1 | 8/2007 | Anderson |
| 2007/0219521 A1 | 9/2007 | Hird |
| 2007/0249254 A1 | 10/2007 | Mansfield |
| 2007/0254176 A1 | 11/2007 | Patel |
| 2007/0254547 A1 | 11/2007 | Ducauchuis |
| 2007/0287983 A1 | 12/2007 | Lodge et al. |
| 2008/0003910 A1 | 1/2008 | Hughes |
| 2008/0003911 A1 | 1/2008 | Sabbagh |
| 2008/0051748 A1 | 2/2008 | Black |
| 2008/0076315 A1 | 3/2008 | Mccormack |
| 2008/0119102 A1 | 5/2008 | Hughes |
| 2008/0147031 A1 | 6/2008 | Long |
| 2008/0241476 A1 | 10/2008 | Olguin |
| 2008/0305298 A1 | 12/2008 | Lakshmi |
| 2008/0312622 A1 | 12/2008 | Hundorf |
| 2009/0035527 A1 | 2/2009 | Kobayashi |
| 2009/0069772 A1 | 3/2009 | Sauer |
| 2009/0069778 A1 | 3/2009 | Sauer |
| 2009/0191779 A1 | 7/2009 | Cree |
| 2009/0240222 A1 | 9/2009 | Tomoko |
| 2009/0258210 A1 | 10/2009 | Iyad et al. |
| 2009/0275909 A1 | 11/2009 | Sakaguchi |
| 2009/0292266 A1 | 11/2009 | Bäck |
| 2009/0294044 A1 | 12/2009 | Gill et al. |
| 2009/0299318 A1 | 12/2009 | Faulks |
| 2009/0299322 A1 | 12/2009 | Faulks |
| 2009/0325447 A1 | 12/2009 | Austin |
| 2009/0325448 A1 | 12/2009 | Welch |
| 2010/0062231 A1 | 3/2010 | Abed |
| 2010/0076390 A1 | 3/2010 | Norrby |
| 2010/0090363 A1 | 4/2010 | Larsen |
| 2010/0104830 A1 | 4/2010 | Jaeger |
| 2010/0112313 A1 | 5/2010 | Nakakado |
| 2010/0168704 A1 | 7/2010 | Thomas |
| 2010/0262105 A1 | 10/2010 | Turner |
| 2010/0268183 A1 | 10/2010 | Een |
| 2010/0280481 A1 | 11/2010 | Kline |
| 2011/0004176 A1 | 1/2011 | Andersson |
| 2011/0040273 A1 | 2/2011 | Sablone |
| 2011/0046594 A1 | 2/2011 | Sablone |
| 2011/0139657 A1 | 6/2011 | Hird |
| 2011/0139658 A1 | 6/2011 | Hird |
| 2011/0139659 A1 | 6/2011 | Hird |
| 2011/0144610 A1 | 6/2011 | Karlson |
| 2011/0152812 A1 | 6/2011 | Hird |
| 2011/0178490 A1 | 7/2011 | Lavon |
| 2011/0196332 A1 | 8/2011 | Cheng |
| 2011/0318987 A1 | 12/2011 | Ooishi |
| 2012/0045620 A1 | 2/2012 | Oba |
| 2012/0055613 A1 | 3/2012 | Back |
| 2012/0055615 A1 | 3/2012 | Back |
| 2012/0061015 A1 | 3/2012 | Lavon et al. |
| 2012/0061016 A1 | 3/2012 | Lavon et al. |
| 2012/0095429 A1 | 4/2012 | Kobayashi et al. |
| 2012/0100351 A1 | 4/2012 | Covelli |
| 2012/0116342 A1 | 5/2012 | Stjernholm |
| 2012/0141742 A1 | 6/2012 | Yamaguchi |
| 2012/0143165 A1 | 6/2012 | Macura et al. |
| 2012/0168063 A1 | 7/2012 | Beuther |
| 2012/0196091 A1 | 8/2012 | Mizutani |
| 2012/0209230 A1 | 8/2012 | Mansfield |
| 2012/0238980 A1 | 9/2012 | Lam |
| 2012/0251771 A1 | 10/2012 | Wilson |
| 2012/0277713 A1 | 11/2012 | Raycheck |
| 2012/0316526 A1 | 12/2012 | Rosati et al. |
| 2012/0321839 A1 | 12/2012 | Uematsu |
| 2013/0017370 A1 | 1/2013 | Yamaguchi |
| 2013/0022784 A1 | 1/2013 | Uematsu |
| 2013/0072887 A1 | 3/2013 | LaVon et al. |
| 2013/0082418 A1 | 4/2013 | Curro et al. |
| 2013/0090623 A1 | 4/2013 | Ohashi |
| 2013/0095279 A1 | 4/2013 | Hauschildt |
| 2013/0144245 A1 | 6/2013 | Roe |
| 2013/0158497 A1 | 6/2013 | Yamaguchi |
| 2013/0164480 A1 | 6/2013 | Sakurai et al. |
| 2013/0165883 A1 | 6/2013 | Kimura |
| 2013/0178815 A1 | 7/2013 | Ohashi |
| 2013/0184665 A1 | 7/2013 | Kato |
| 2013/0211356 A1 | 8/2013 | Nishikawa et al. |
| 2013/0213547 A1 | 8/2013 | Schneider et al. |
| 2013/0218116 A1 | 8/2013 | Schneider et al. |
| 2013/0230700 A1 | 9/2013 | Schoenbeck |
| 2013/0236700 A1 | 9/2013 | Yamanaka |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0280481 A1 | 10/2013 | Mitsuno |
| 2013/0284850 A1 | 10/2013 | Lenser |
| 2013/0306226 A1 | 11/2013 | Zink et al. |
| 2014/0018222 A1 | 1/2014 | Sablone |
| 2014/0018759 A1 | 1/2014 | Jayasinghe et al. |
| 2014/0039434 A1 | 2/2014 | Xu |
| 2014/0041786 A1 | 2/2014 | Henke et al. |
| 2014/0135194 A1 | 5/2014 | Sablone |
| 2014/0148774 A1 | 5/2014 | Brown |
| 2014/0163500 A1 | 6/2014 | Roe |

(56) References Cited

U.S. PATENT DOCUMENTS

| | | |
|---|---|---|
| 2014/0163506 A1 | 6/2014 | Roe |
| 2014/0163511 A1 | 6/2014 | Roe et al. |
| 2014/0234575 A1 | 8/2014 | Mitsuno et al. |
| 2014/0330232 A1 | 11/2014 | Schönbeck |
| 2014/0377506 A1 | 12/2014 | Eckstein et al. |
| 2014/0377513 A1 | 12/2014 | Galie et al. |
| 2014/0378924 A1 | 12/2014 | Turner |
| 2015/0032078 A1 | 1/2015 | Collins |
| 2015/0038929 A1 | 2/2015 | Van Malderen |
| 2015/0057630 A1 | 2/2015 | Tange |
| 2015/0126955 A1 | 5/2015 | Sauer et al. |
| 2015/0147530 A1 | 5/2015 | Mitsuno |
| 2015/0147539 A1 | 5/2015 | Thomas |
| 2015/0164699 A1 | 6/2015 | Schmitz |
| 2015/0164705 A1 | 6/2015 | Thomas |
| 2015/0173961 A1 | 6/2015 | Powell et al. |
| 2015/0202091 A1 | 7/2015 | Sablone |
| 2015/0297419 A1 | 10/2015 | Nelson |
| 2015/0297421 A1 | 10/2015 | Nelson |
| 2015/0313774 A1 | 11/2015 | Homoelle et al. |
| 2016/0013614 A1 | 1/2016 | Moto |
| 2016/0136014 A1 | 5/2016 | Arora |
| 2016/0167334 A1 | 6/2016 | Arora |
| 2016/0206485 A1 | 7/2016 | Seitz |
| 2016/0270972 A1 | 9/2016 | Surushe et al. |
| 2016/0324697 A1 | 11/2016 | Schoenbeck |
| 2017/0027775 A1 | 2/2017 | Barnes |
| 2017/0056256 A1 | 3/2017 | Smith et al. |
| 2017/0079851 A1 | 3/2017 | Greening, II |
| 2017/0079854 A1 | 3/2017 | Butler |
| 2017/0087029 A1 | 3/2017 | Nelson |
| 2017/0252229 A1 | 9/2017 | Bonelli |
| 2017/0335498 A1 | 11/2017 | Hansen |
| 2018/0014979 A1 | 1/2018 | Fujita |
| 2018/0015709 A1 | 1/2018 | Takeuchi |
| 2018/0042777 A1 | 2/2018 | Dalal et al. |
| 2018/0042778 A1 | 2/2018 | Lenser et al. |
| 2018/0042779 A1 | 2/2018 | Lenser |
| 2018/0042780 A1 | 2/2018 | Lenser et al. |
| 2018/0042784 A1 | 2/2018 | Koshijima |
| 2018/0042785 A1 | 2/2018 | Dalal et al. |
| 2018/0042786 A1 | 2/2018 | Mueller |
| 2018/0042787 A1 | 2/2018 | Lenser et al. |
| 2018/0271716 A1 | 9/2018 | Dalal |
| 2018/0271717 A1 | 9/2018 | Dria |
| 2018/0281296 A1 | 10/2018 | Uchida |
| 2019/0046363 A1 | 2/2019 | Lenser |
| 2019/0083323 A1 | 3/2019 | Sakai |
| 2019/0110936 A1 | 4/2019 | Becker |
| 2020/0179179 A1 | 6/2020 | Lenser |
| 2020/0268563 A1 | 8/2020 | Lenser |

FOREIGN PATENT DOCUMENTS

| | | |
|---|---|---|
| EP | 1256594 A1 | 11/2002 |
| EP | 1447066 A1 | 8/2004 |
| EP | 1263580 B1 | 9/2010 |
| EP | 1990188 B1 | 10/2012 |
| EP | 2891480 A1 | 7/2015 |
| EP | 2841364 B1 | 8/2016 |
| EP | 3246443 A1 | 11/2017 |
| EP | 2647360 B1 | 6/2018 |
| JP | 2004223238 A | 8/2004 |
| JP | 2007521036 A | 8/2007 |
| JP | 2011139843 A | 7/2011 |
| JP | 4934835 B2 | 3/2012 |
| JP | 5036641 B2 | 7/2012 |
| JP | 2012524645 A | 10/2012 |
| JP | 6240733 B1 | 11/2017 |
| JP | 2017065142 A | 11/2018 |
| WO | WO9510996 | 4/1995 |
| WO | WO9511652 | 5/1995 |
| WO | WO9516746 A1 | 6/1995 |
| WO | WO9828123 A1 | 7/1998 |
| WO | WO2000045763 | 8/2000 |
| WO | WO2000059430 | 10/2000 |
| WO | 0073031 A1 | 12/2000 |
| WO | WO2002067809 | 9/2002 |
| WO | WO2003007864 A1 | 1/2003 |
| WO | 2004017882 A2 | 3/2004 |
| WO | WO2004017885 | 3/2004 |
| WO | WO2004060652 A1 | 7/2004 |
| WO | 2006124337 A1 | 11/2006 |
| WO | 2006138725 A2 | 12/2006 |
| WO | WO2007036907 | 4/2007 |
| WO | 2008023291 A3 | 2/2008 |
| WO | WO2008156075 A1 | 12/2008 |
| WO | WO2009146307 A1 | 12/2009 |
| WO | WO2010055699 A1 | 5/2010 |
| WO | WO2010118214 A1 | 10/2010 |
| WO | WO2010126415 A1 | 11/2010 |
| WO | WO2011080643 A2 | 7/2011 |
| WO | WO2011125893 A1 | 10/2011 |
| WO | WO2012052172 | 4/2012 |
| WO | WO2012030571 A3 | 5/2012 |
| WO | WO2012112501 | 8/2012 |
| WO | WO2012137553 A1 | 10/2012 |
| WO | 2012154318 A1 | 11/2012 |
| WO | 2013027390 A1 | 2/2013 |
| WO | WO2013018846 A1 | 2/2013 |
| WO | WO2013047890 A1 | 4/2013 |
| WO | WO2013132403 A1 | 9/2013 |
| WO | WO2013157365 A1 | 10/2013 |
| WO | WO2013163141 A1 | 10/2013 |
| WO | WO2014011839 A1 | 1/2014 |
| WO | WO2015168032 A1 | 11/2015 |
| WO | WO2015195467 A1 | 12/2015 |
| WO | WO2015195468 A1 | 12/2015 |
| WO | WO2016069269 | 5/2016 |
| WO | WO2016073713 | 5/2016 |
| WO | 2016109514 A1 | 7/2016 |
| WO | 2018031841 A1 | 2/2018 |
| WO | 2018183315 A1 | 10/2018 |
| WO | WO2016121979 A1 | 1/2019 |
| WO | 2019089689 A2 | 5/2019 |

OTHER PUBLICATIONS

All Office Actions, U.S. Appl. No. 15/674,596.
All Office Actions, U.S. Appl. No. 15/674,559.
All Office Actions, U.S. Appl. No. 15/674,563.
All Office Actions, U.S. Appl. No. 15/674,566.
All Office Actions, U.S. Appl. No. 15/674,575.
All Office Actions, U.S. Appl. No. 15/674,625.
All Office Actions, U.S. Appl. No. 15/937,180.
All Office Actions, U.S. Appl. No. 15/937,235.
All Office Actions, U.S. Appl. No. 16/049,977.
All Office Actions, U.S. Appl. No. 16/741,819.
All Office Actions, U.S. Appl. No. 16/748,885.
PCT International Search Report, Appl. No. PCT/US2017/046388, dated Sep. 22, 2017, 15 pages.
International Search Report, Appl. No. PCT/US2017/046397, dated Sep. 28, 2017, 13 pages.
PCT International Search Report, Appl. No. PCT/US2017/046394, dated Sep. 28, 2017, 15 pages.
All Office Actions, U.S. Appl. No. 15/674,561.
EP Application No. 17754982.1, Third Party Observation, dated Jun. 17, 2020, 9 pages.
International Search Report, Appl. No. PCT/US2017/046398, dated Sep. 28, 2017, 13 pages.
International Search Report and Written Opinion, Appl. No. PCT/US2018/024549, dated May 30, 2018, 13 pages.
PCT International Search Report, Appl. No. PCT/US2017/046395, dated Sep. 20, 2017, 15 pages.
EP Application No. 17764961.3, Third Party Observation, dated Aug. 24, 2020, 6 pages.
International Search Report, Appl. No. PCT/US2017/049026, dated Oct. 19, 2017, 13 pages.
International Search Report, Appl. No. PCT/US2019/024011, dated Jul. 4, 2019, 14 pages.

(56) References Cited

OTHER PUBLICATIONS

U.S. Appl. No. 16/916,655, filed Jun. 30, 2020, Nelson Edward Greening, II et al.
Extended European Search Report and Search Opinion; Application No. 20183749.9; dated Nov. 9, 2020; 8 pages.
International Search Report and Written Opinion; Application No. PCT/US2020/070219; dated Oct. 1, 2020; 14 pages.

* cited by examiner

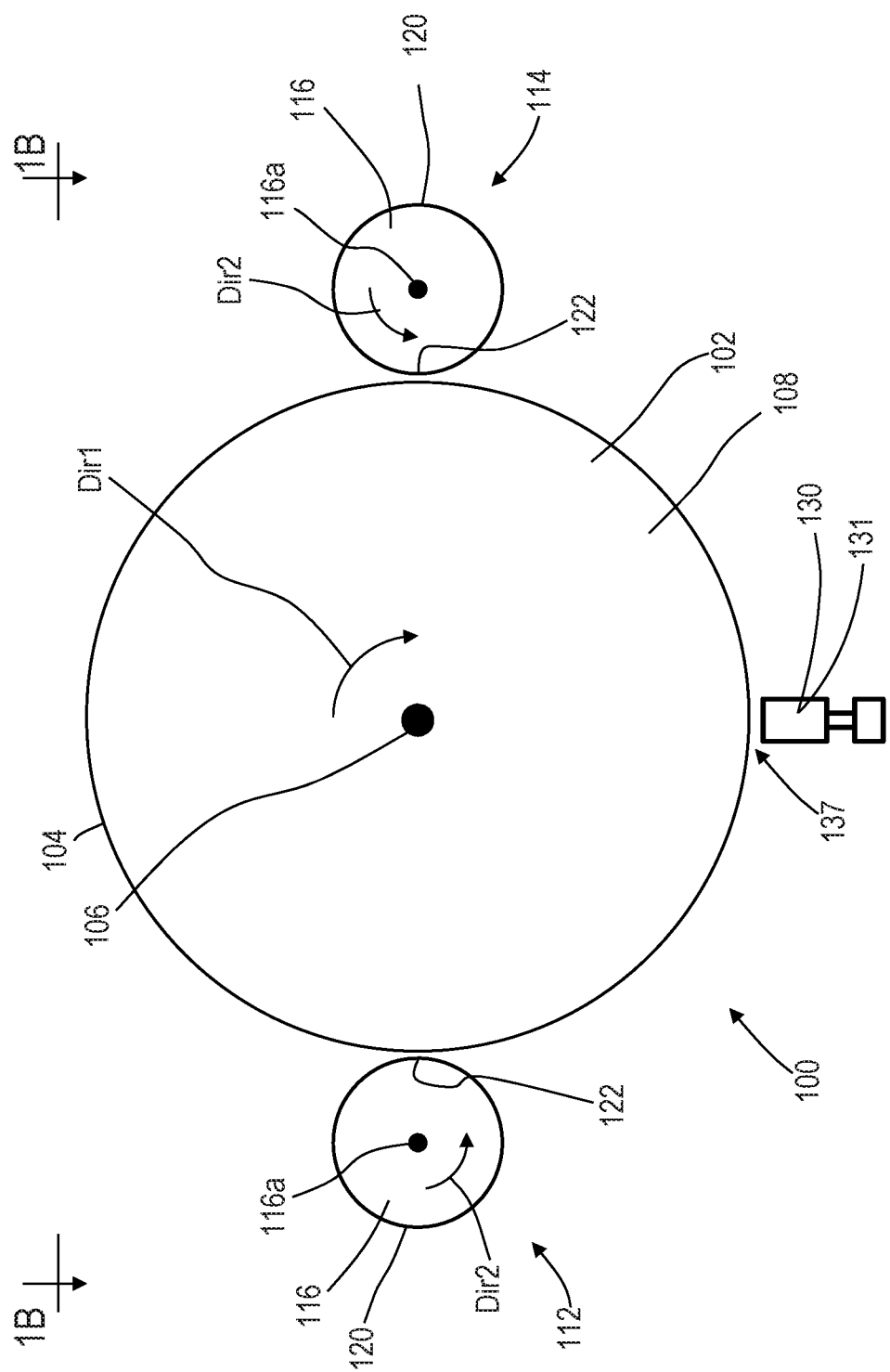

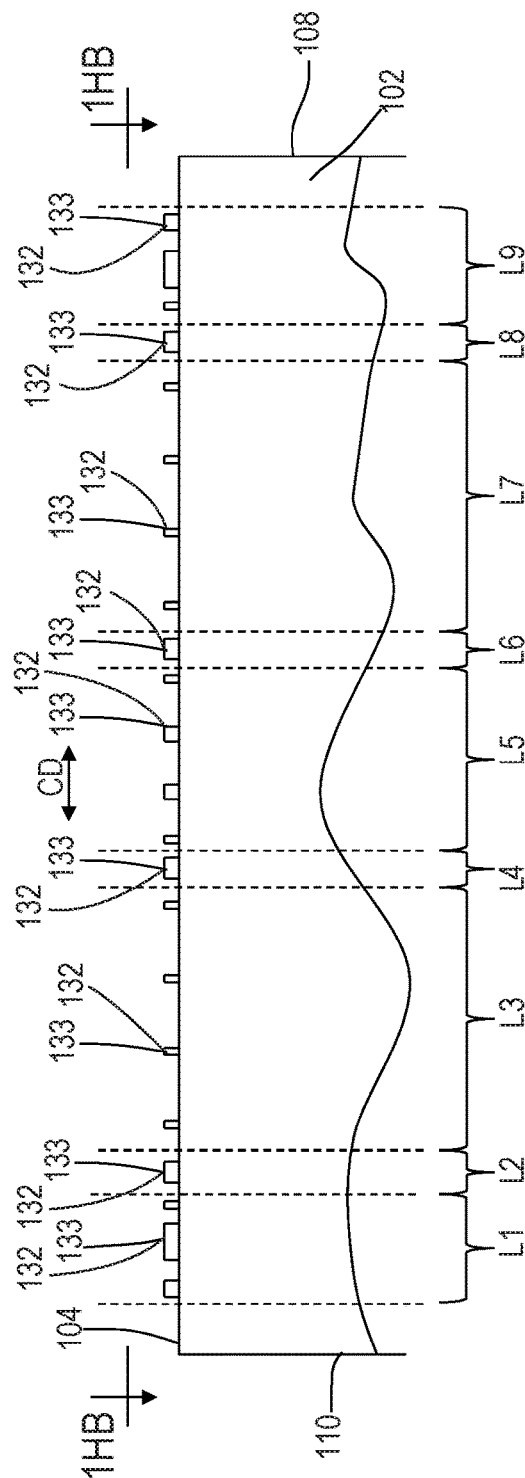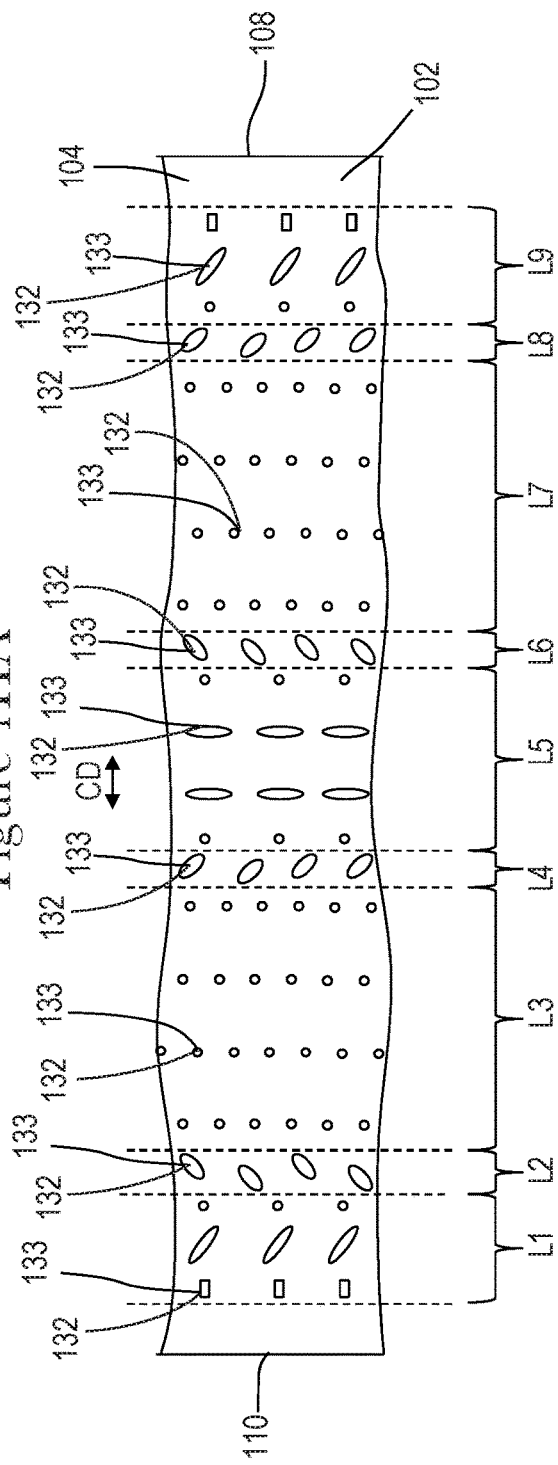

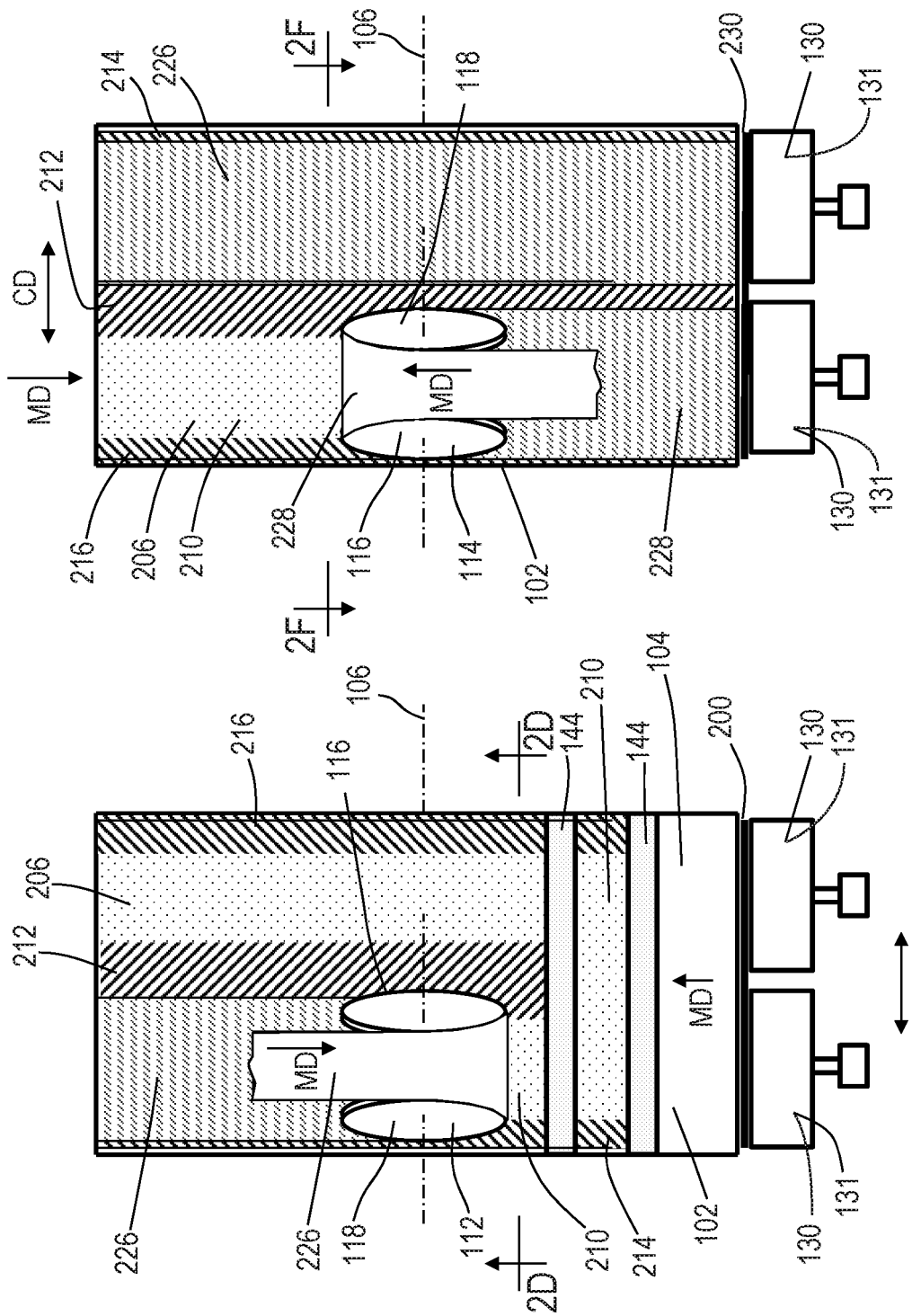

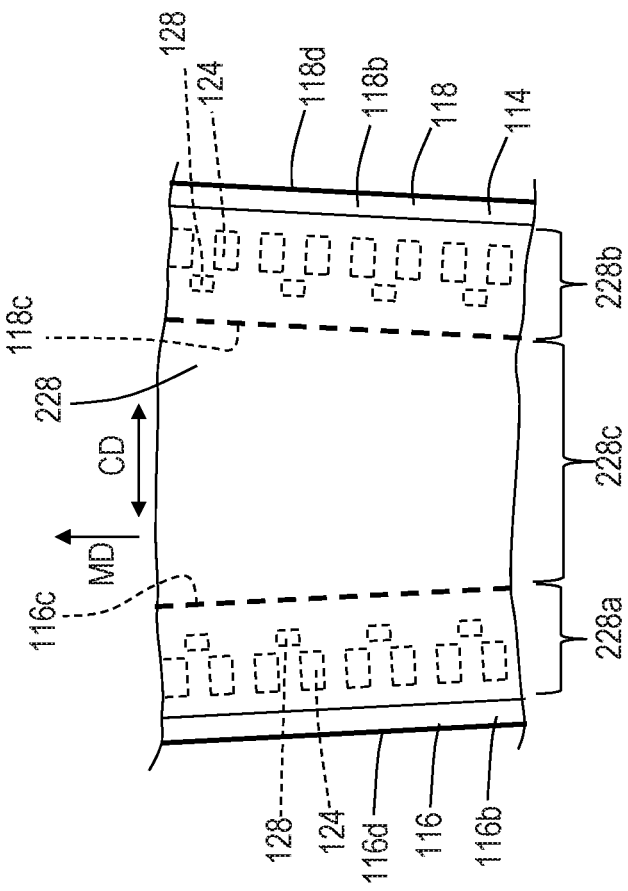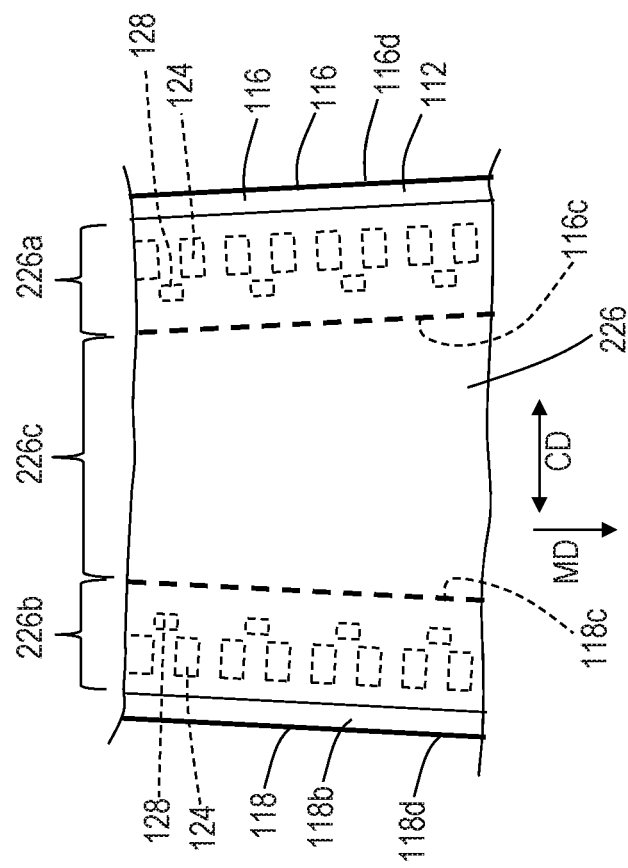

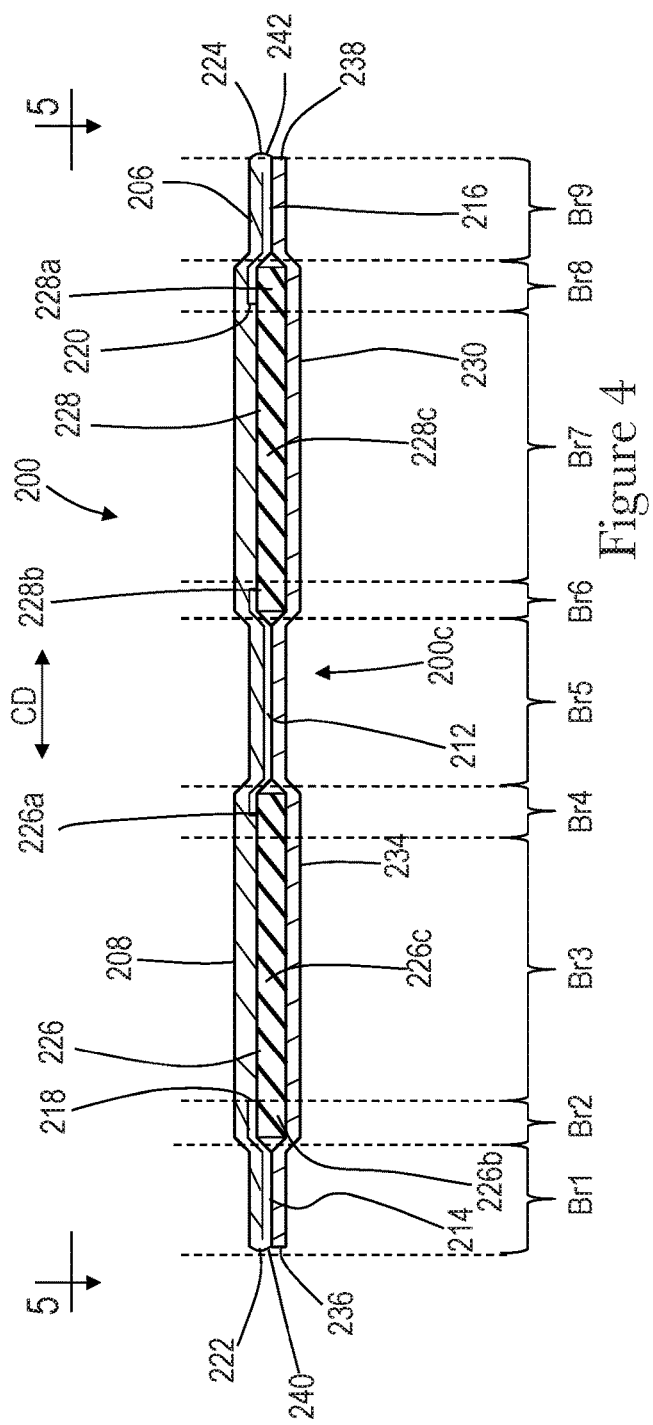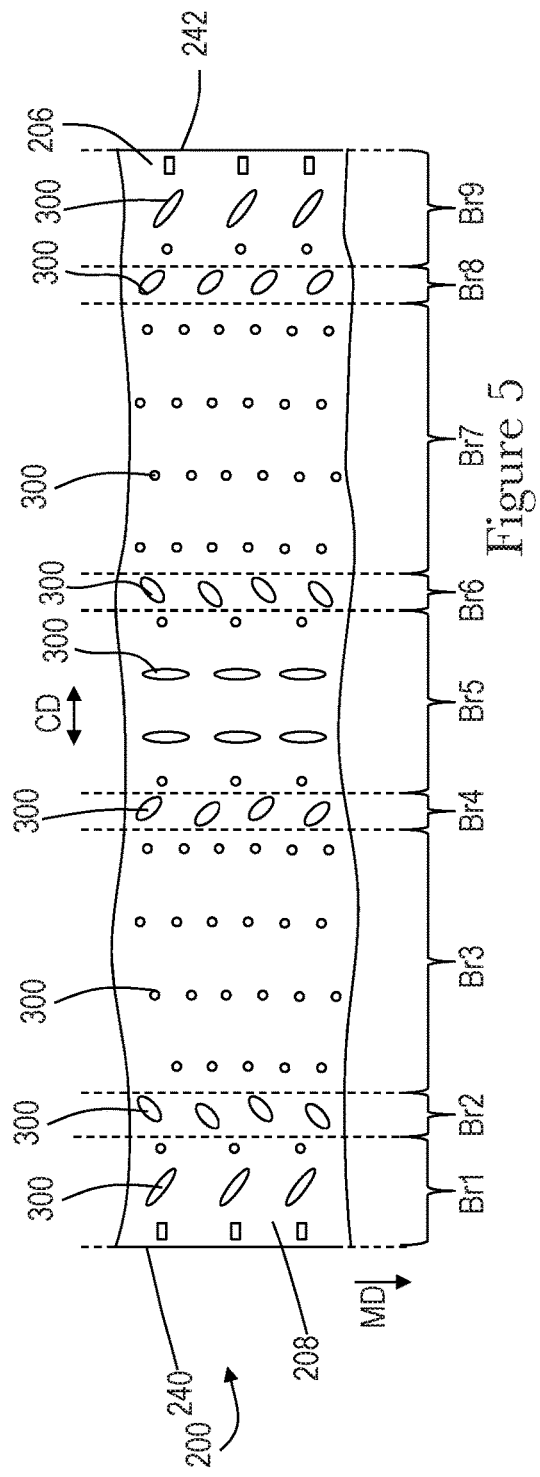

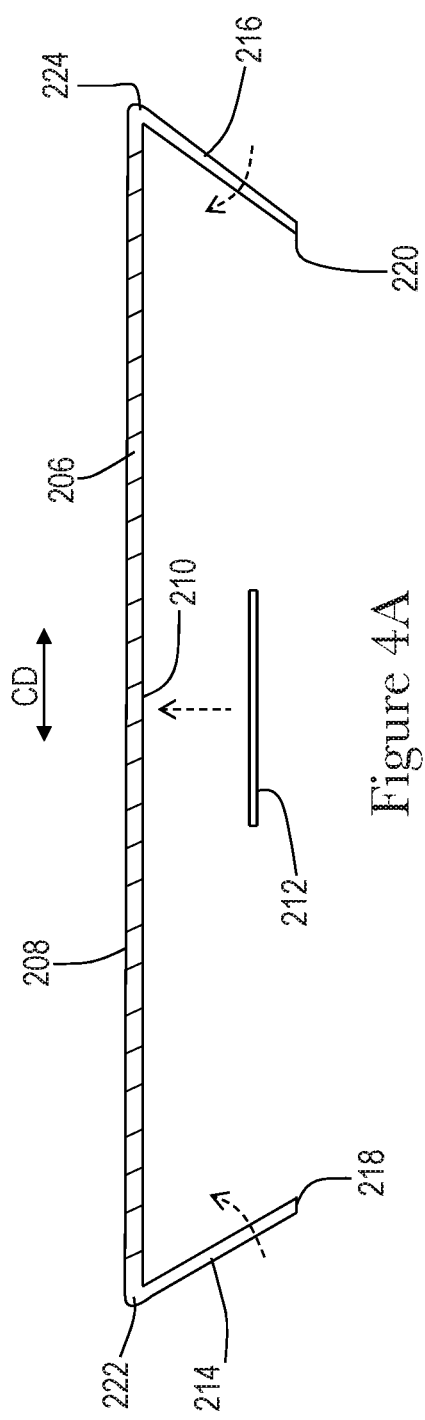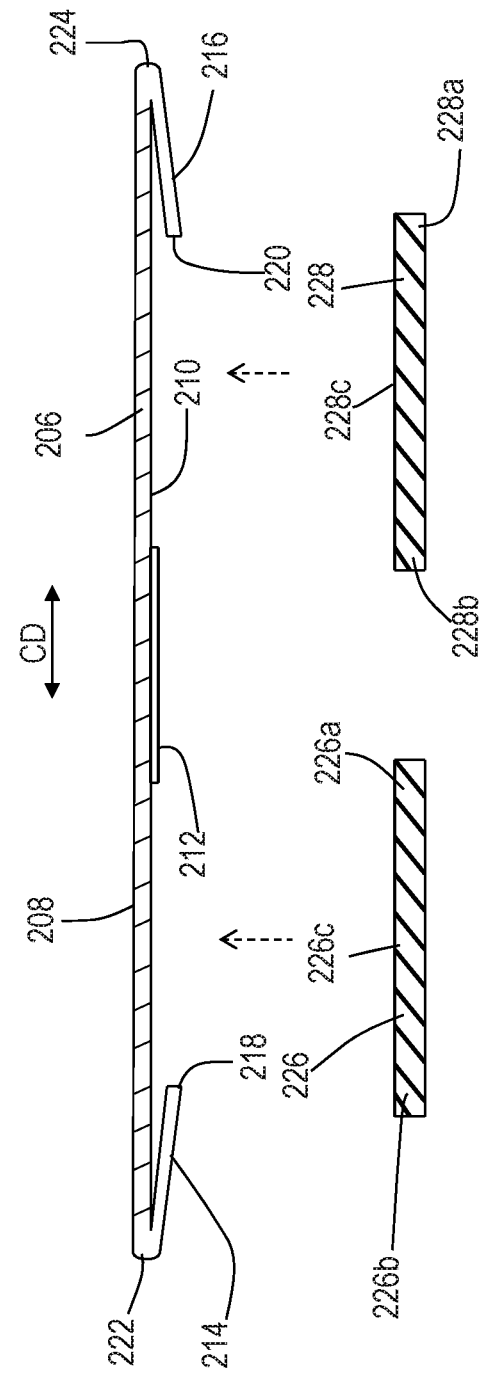

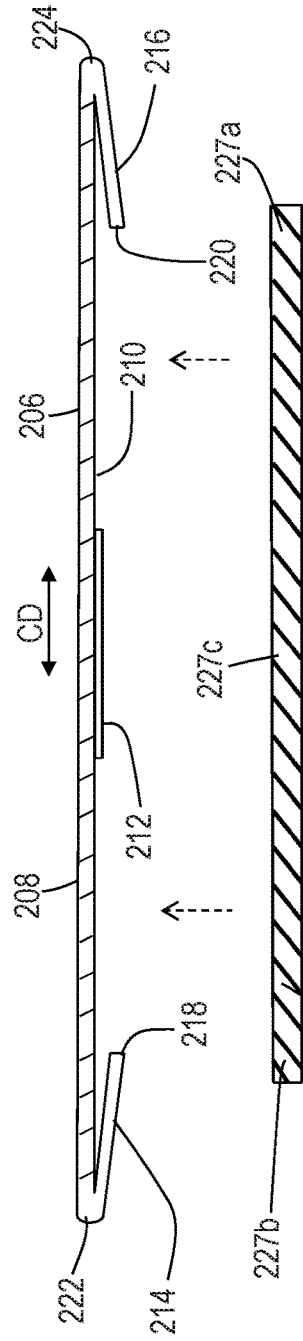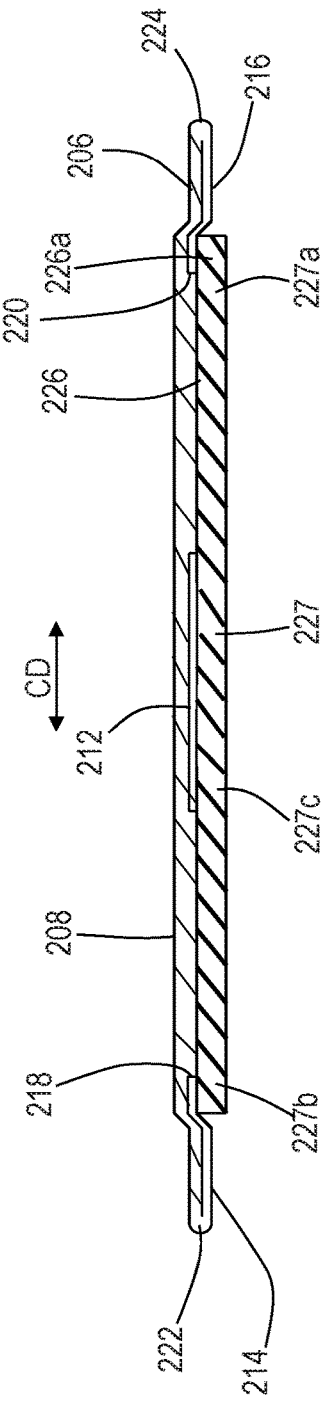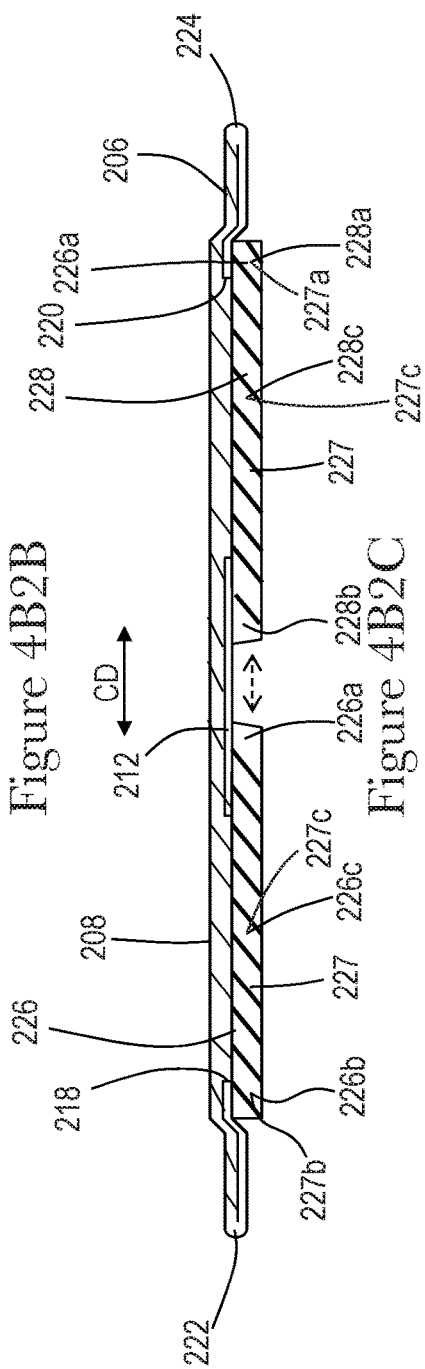

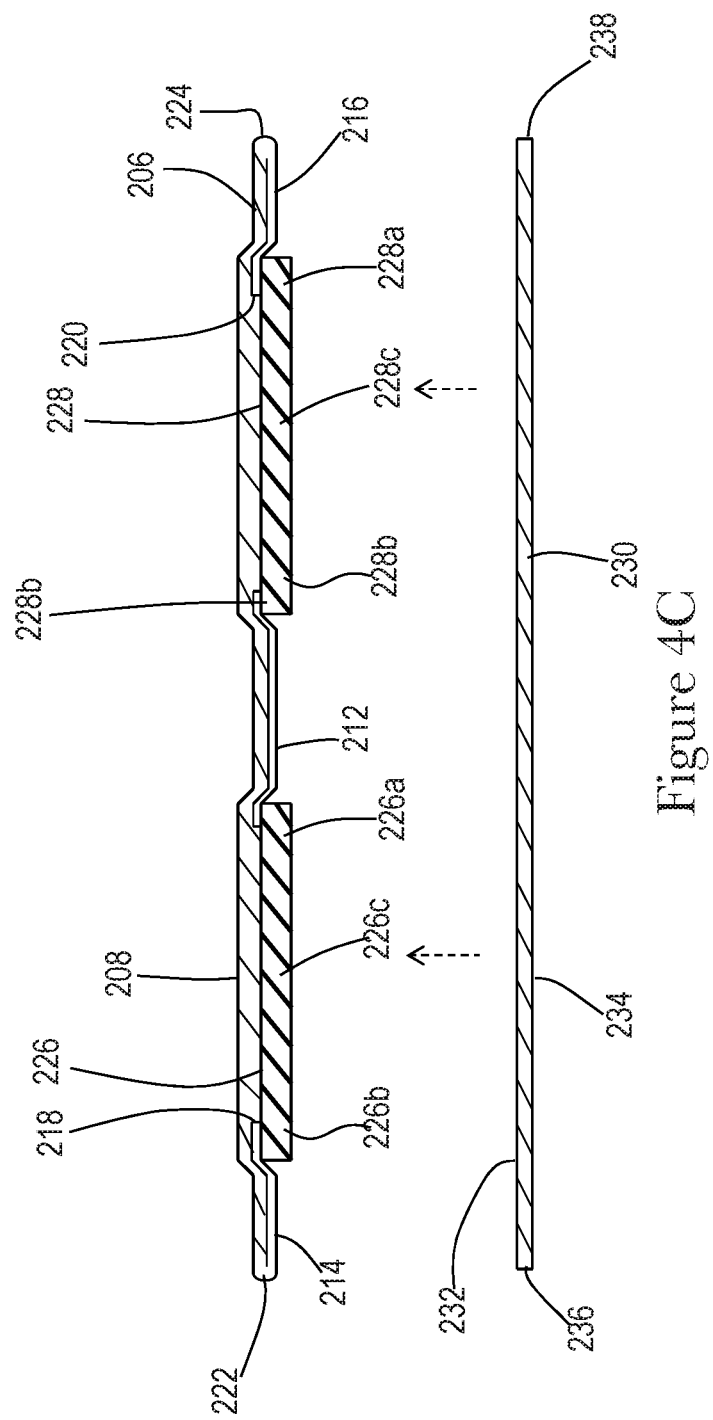

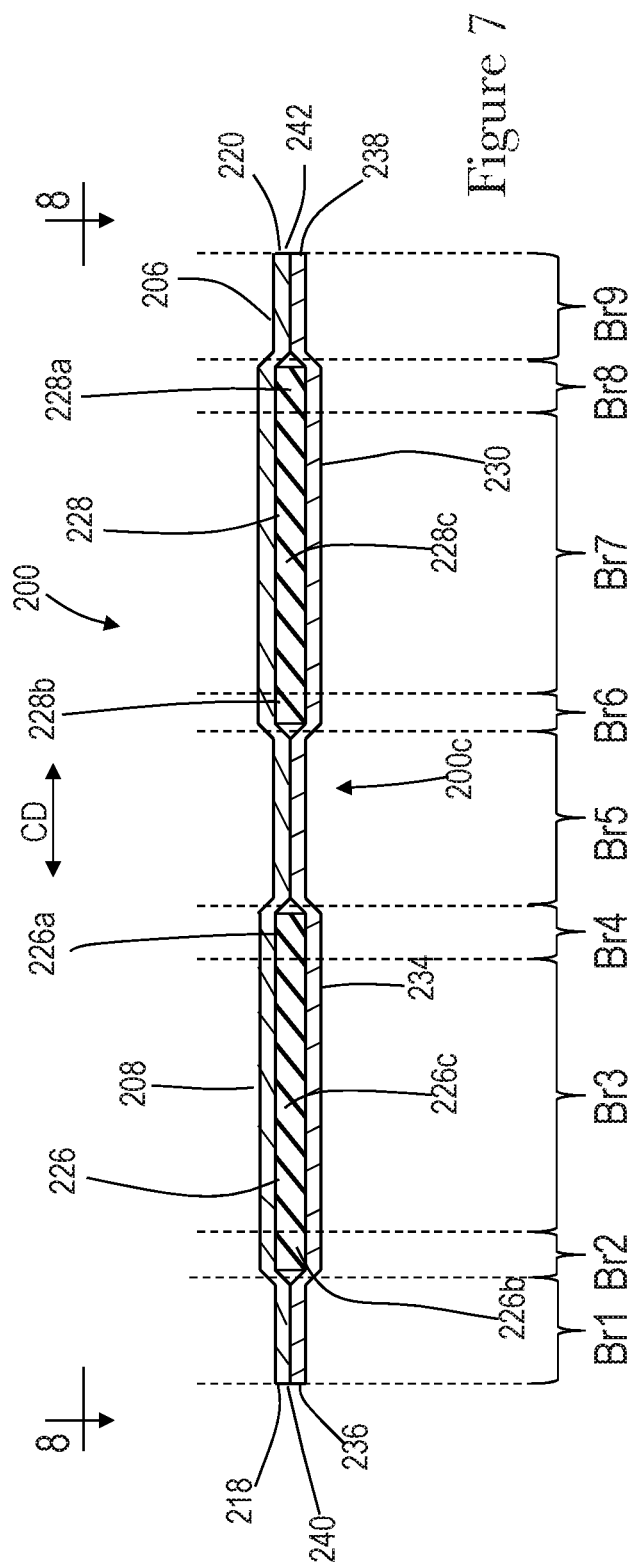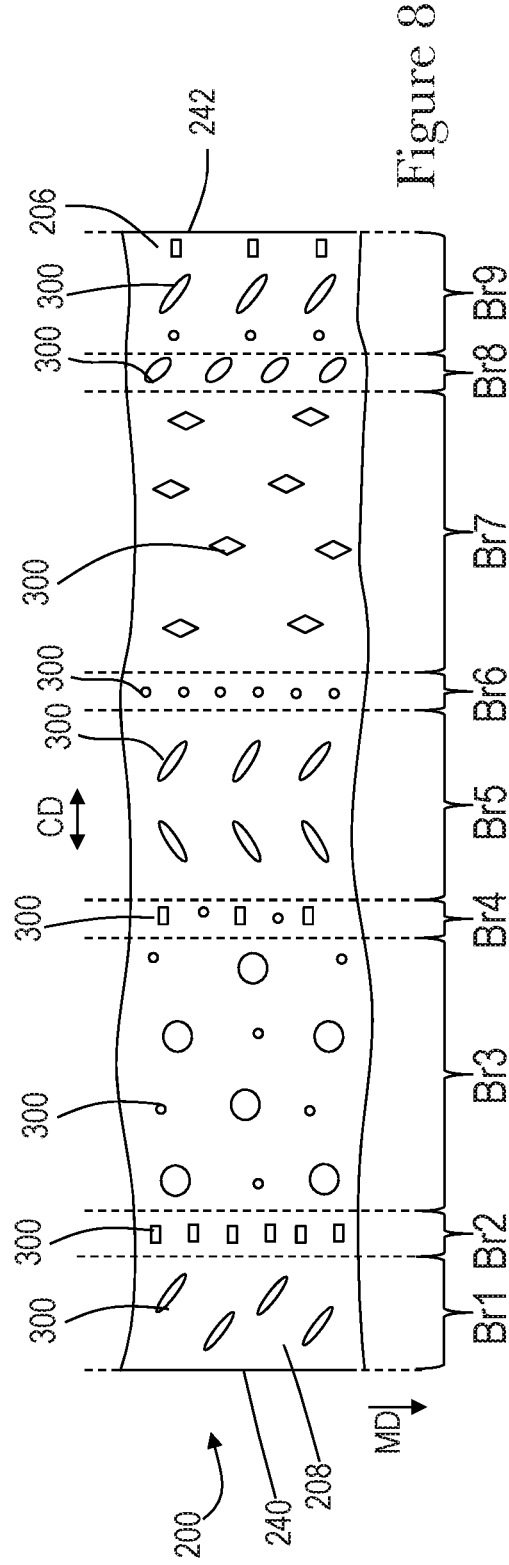

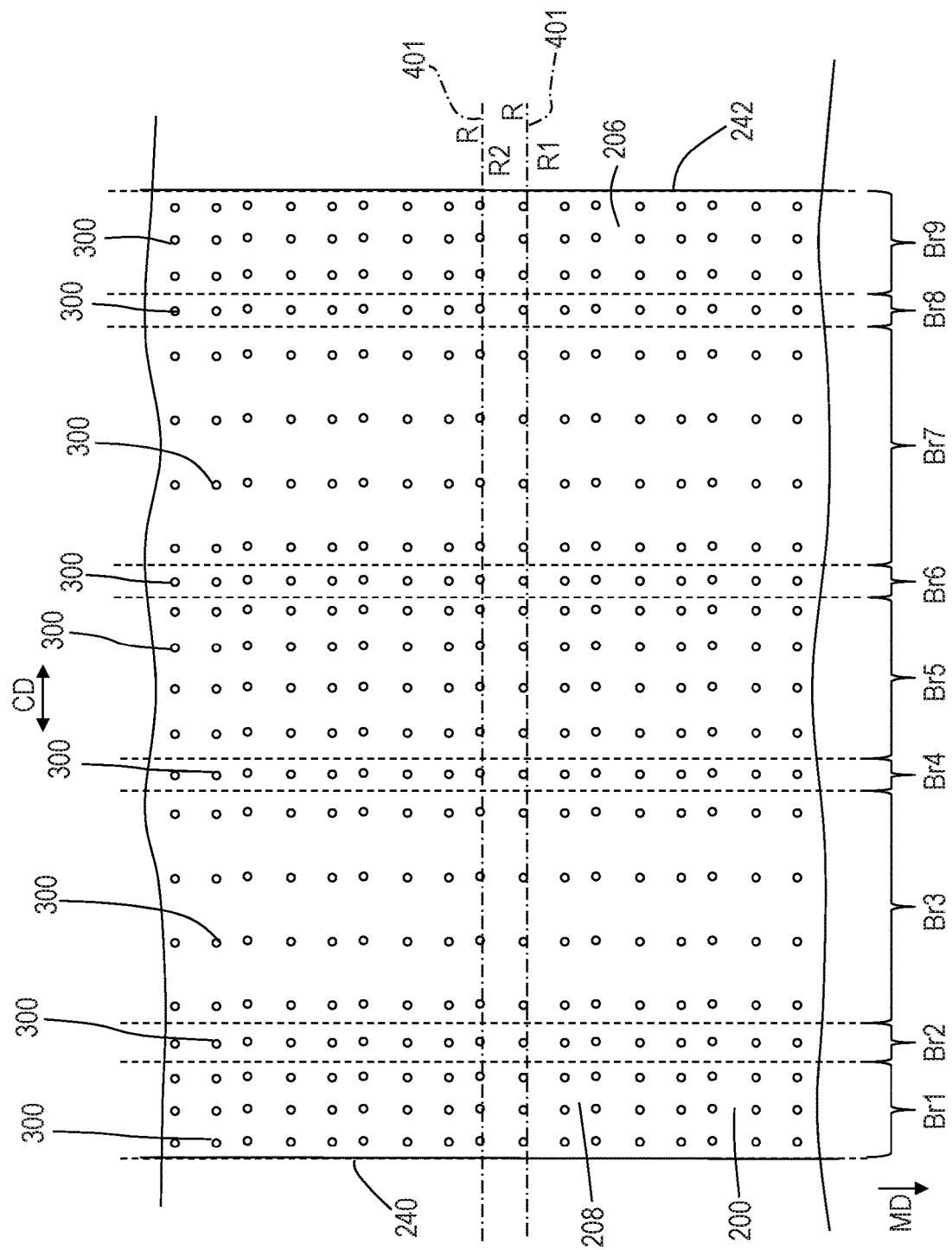

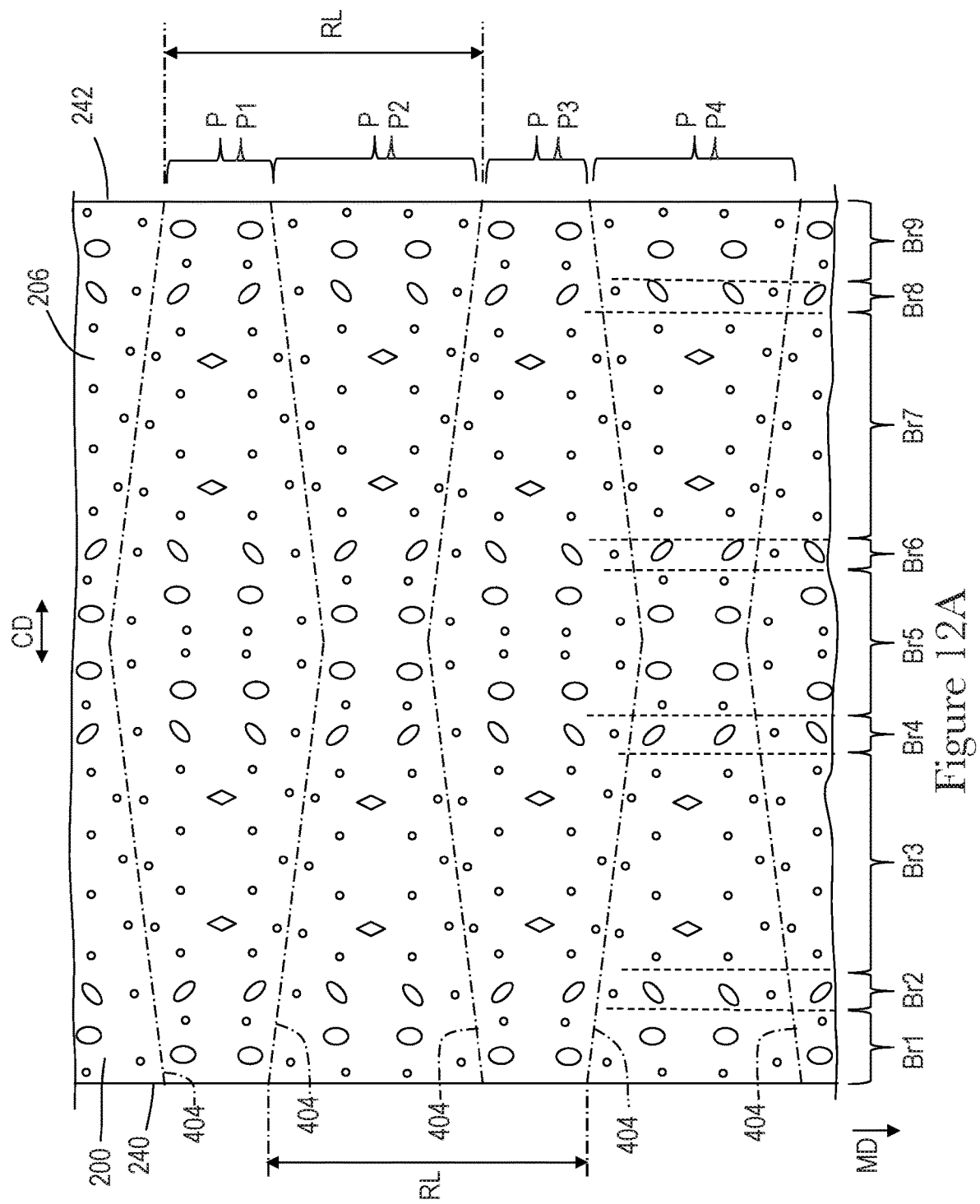

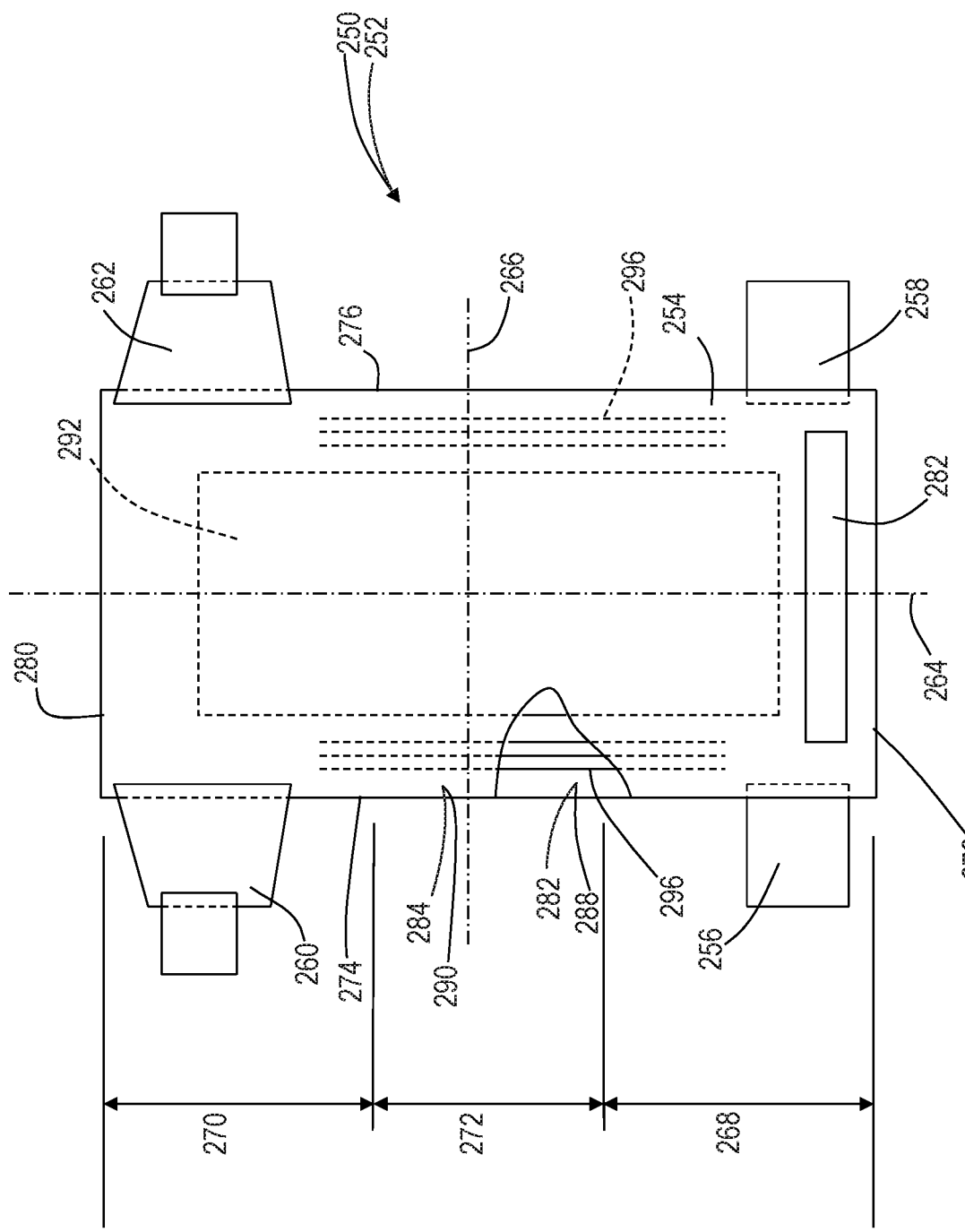

METHODS AND APPARATUSES FOR ASSEMBLING ELASTIC LAMINATES WITH DIFFERENT BOND DENSITIES FOR ABSORBENT ARTICLES

CROSS REFERENCE TO RELATED APPLICATIONS

This application is a continuation of U.S. application Ser. No. 15/674,596, filed on Aug. 11, 2017, which claims the benefit of U.S. Provisional Application Nos. 62/374,010, filed on Aug. 12, 2016; 62/406,025, filed on Oct. 10, 2016; and 62/419,515, filed on Nov. 9, 2016, the entireties of which are all incorporated by reference herein.

FIELD OF THE INVENTION

The present disclosure relates to methods for manufacturing absorbent articles, and more particularly, to apparatuses and methods for assembling elastic laminates for making absorbent article components.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, and fastening components. Once the desired component parts are assembled, the advancing web(s) and component parts are subjected to a final knife cut to separate the web(s) into discrete diapers or other absorbent articles.

Some diaper components, such as leg elastics, barrier leg cuff elastics, stretch side panels, and waist elastics, are constructed from elastic laminates. Such elastic laminates may be assembled in various ways depending on the particular diaper design. For example, some elastic laminates may be constructed from one or more nonwoven substrates bonded to an elastic film. In some configurations, the elastic film may be stretched and then bonded with the nonwoven substrates to form an elastic laminate.

Some existing elastic laminate assembly operations may have certain drawbacks. For example, manufacturing operations may be configured with machines adapted to grip and stretch the films before bonding the stretched films to other substrates, such as nonwoven layers. With some gripping operations, portions of the film may remain unstretched in the assembled elastic laminate. Such unstretched portions of the film may add no benefit with respect to the desired elasticity of the assembled elastic laminate. However, the unstretched portions of the film may be bonded with one or more nonwoven layers to help anchor and secure the film to the nonwoven substrates. In addition, the nonwoven layers may be bonded directly to each other in areas where the elastic film is not present. In use, the elastic laminates may be stretched by applying forces to the elastic laminates in the regions where the unstretched portions of the film are anchored to the nonwovens. As such, when assembling elastic laminates, it may be advantageous to utilize bond configurations that help to ensure that the unstretched portions of the film and the nonwovens remain bonded together and do not separate from each other during use. However, such bond configurations used to bond nonwovens to each other and/or to unstretched portions of the films may not be suitable for bonding stretchable portions of films to the nonwovens and may detract from the desired stretch properties, aesthetic appearance, and/or tactile impression of the assembled elastic laminate. Conversely, bond configurations used to bond stretchable portions of films to the nonwovens may not be suitable for bonding nonwovens to each other and/or to unstretched portions of the films, because such bond configurations may not provide the strength needed to ensure that unstretched portions of the film and/or nonwovens remain bonded together during use.

Consequently, it would be beneficial to provide methods and apparatuses for assembling elastic laminates that are configured to apply pluralities of bonds with different bond densities in different regions of the elastics laminates.

SUMMARY OF THE INVENTION

In one form, a method for assembling elastic laminates comprises the steps of: providing a first substrate and a second substrate, the first substrate and the second substrate each comprising a first surface and an opposing second surface, a first longitudinal edge and a second longitudinal edge separated from the first longitudinal edge to define a width in a cross direction; providing a first elastic film and a second elastic film, each of the first elastic film and the second elastic film comprising a stretched central region; positioning the stretched central region of the first elastic film in contact with the second surface of the first substrate; positioning the stretched central region of the second elastic film in contact with the second surface of the first substrate; forming an elastic laminate by advancing the second substrate in a machine direction to position the first surface of the second substrate in contact with the stretched central regions of the first and second elastic films, wherein the elastic laminate comprises a first bonding region and a second bonding region, wherein the first bonding region is defined where the stretched central region of the first elastic film is in direct contact with the second surface of the first substrate and the first surface of the second substrate, and wherein the second bonding region is positioned completely outside the first bonding region; applying a first plurality of ultrasonic bonds to the elastic laminate to define a first bond density in the first bonding region; and applying a second plurality of ultrasonic bonds to the elastic laminate to define a second bond density in the second bonding region, and wherein the elastic laminate comprises at least one more layer in the second bonding region than in the first bonding region.

In another form, a method for assembling elastic laminates comprises the steps of: providing a first substrate and a second substrate, the first substrate and the second substrate each comprising a first surface and an opposing second surface, a first longitudinal edge and a second longitudinal edge separated from the first longitudinal edge to define a width in a cross direction; providing a first elastic film and a second elastic film, each of the first elastic film and the second elastic film comprising a stretched central region; positioning the stretched central region of the first elastic film in contact with the second surface of the first substrate; positioning the stretched central region of the second elastic film in contact with the second surface of the first substrate; forming an elastic laminate by advancing the second substrate in a machine direction to position the first surface of the second substrate in contact with the stretched central regions of the first and second elastic films, wherein the elastic laminate comprises a first bonding region and a second bonding region, wherein the first bonding region is defined where the stretched central region of the first elastic film is in direct contact with the second surface of the first substrate and the first surface of the second substrate, and wherein the second bonding region is positioned completely outside the first bonding region; applying a first plurality of ultrasonic bonds to the elastic laminate to define a first bond density in the first bonding region; and applying a second plurality of ultrasonic bonds to the elastic laminate to define a second bond density in the second bonding region, wherein the first bond density is not equal to the second bond density, or wherein the first bond density is equal to the second bond density and wherein at least one of the first plurality of ultrasonic bonds comprises a shape that is different from a shape of at least one of the second plurality of ultrasonic bonds.

BRIEF DESCRIPTION OF THE DRAWINGS

FIG. 1A is a schematic side view of an apparatus for assembling an elastic laminate.

FIG. 1HB is a detailed view of a portion of the outer circumferential surface of the anvil from FIG. 1HA taken along line 1HB-1HB.

FIG. 1HC is a detailed view of an example bonding element.

FIG. 2B is a left side view of the apparatus from FIG. 2A taken along line 2B-2B.

FIG. 2D is a detailed view of a first elastic material advancing on a first spreader mechanism from FIG. 2B taken along line 2D-2D.

FIG. 2E is a right side view of the apparatus from FIG. 2A taken along line 2E-2E.

FIG. 2F is a detailed view of a second elastic material advancing on a second spreader mechanism from FIG. 2E taken along line 2F-2F.

FIG. 4 is a cross sectional view of the elastic laminate from FIG. 2A taken along line 4-4.

FIG. 4A is a cross sectional view of a first substrate and reinforcement layers being combined.

FIG. 4B1 is a cross sectional view of first and second elastic materials being combined with the first substrate and reinforcement layers of FIG. 4A.

FIG. 4B2A is a cross sectional view of a single elastic material being combined with the first substrate and reinforcement layers of FIG. 4A.

FIG. 4B2B is a cross sectional view of the combined single elastic material, first substrate, and reinforcement layers of FIG. 4B2A.

FIG. 4B2C is a cross sectional view of the elastic material of FIG. 4B2B being slit into a first elastic material and a second elastic material.

FIG. 4C is a cross sectional view of a second substrate being combined with the first substrate, reinforcement layers, and first and second elastic materials.

FIG. 5 is a detailed top plan view of the elastic laminate from FIG. 4 taken along line 5-5.

FIG. 7 is a cross sectional view of an alternative configuration of an elastic laminate.

FIG. 8 is a detailed top plan view of the elastic laminate from FIG. 7 taken along line 8-8.

FIG. 10B is a top plan view of an elastic laminate with bonds that correspond with bonding surfaces shown in FIG. 10A.

FIG. 12A is a top plan view of an elastic laminate with repeating patterns of bonds.

FIG. 13A is a partially cut away plan view of an absorbent article in the form of a taped diaper that may include one or more elastic laminates manipulated during manufacture according to the apparatuses and methods disclosed herein with the portion of the diaper that faces away from a wearer oriented towards the viewer.

DETAILED DESCRIPTION OF THE INVENTION

Figure 1B:
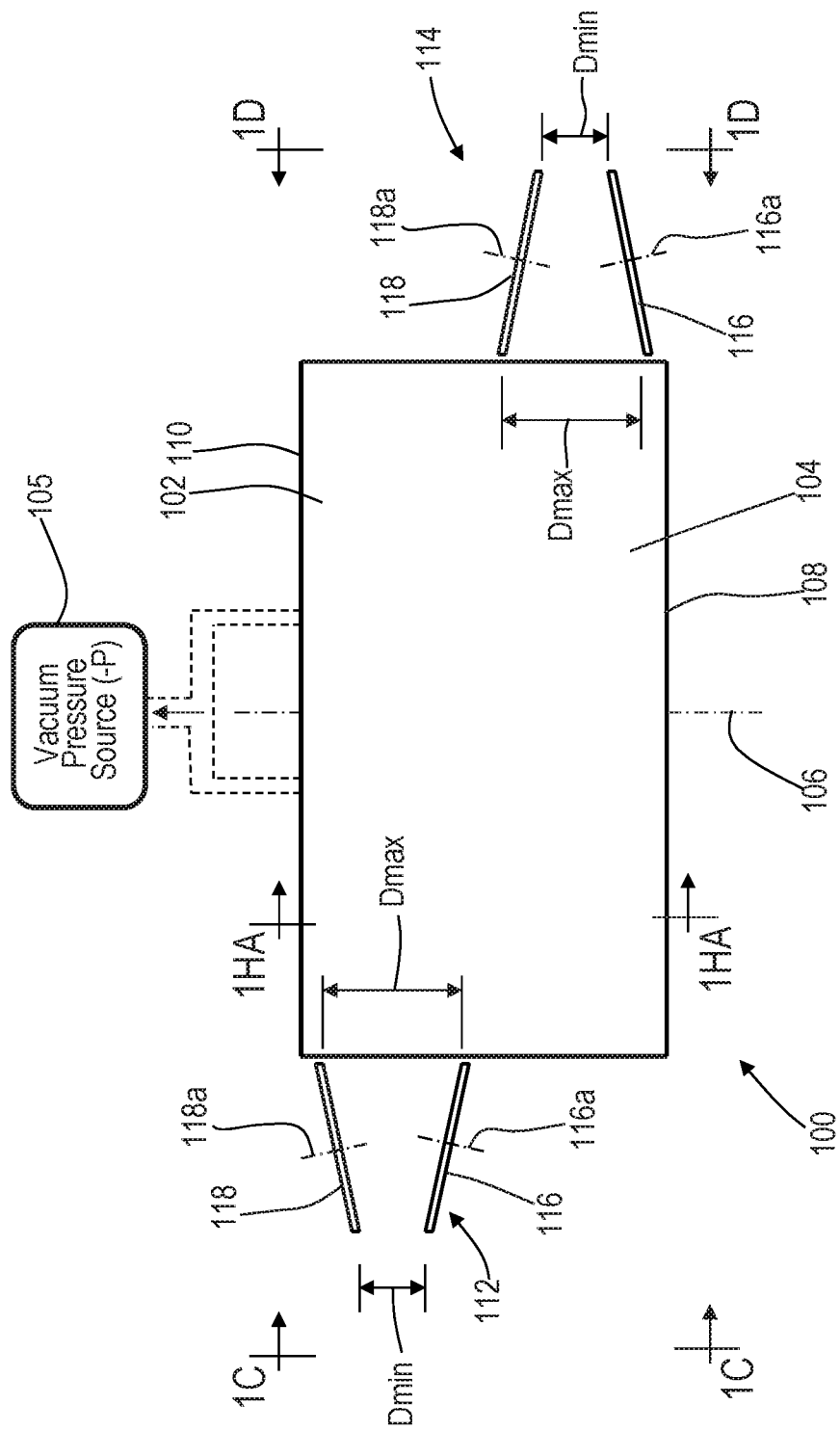
FIG. 1B is a top side view of the apparatus from FIG. 1A taken along line 1B-1B.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. In some configurations, "elastic," "elastomeric," or "elastically extensible" material be stretched by at least 50% strain without rupture or breakage at a given load at 0.1 sec-1 strain rate, and upon release of the load the elastic material or component exhibits at least 70% recovery (i.e., has less than 30% set). For example, an elastic material that may have an initial length of 25.4 mm may stretch to at least 38.1 mm (50% stretch) and, upon removal of the force, retract to a length of 27.95 mm (i.e., have a set of 2.54 mm or 20%) when measured immediately.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern. The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "bond density" refers to bond frequency and/or aggregate bond coverage. The term "bond frequency" refers to the number of bonds per $cm^2$ as determined by the Bond Dimension Test Method herein.

The term "aggregate bond coverage" refers to the sum of the bond areas in a given region as determined by the Bond Dimension Test Method herein.

"Design element" as used herein means a shape or combination of shapes that visually create a distinct and discrete component, regardless of the size or orientation of the component. A design element may be present in one or more patterns. A design element may be present one or more times within one pattern. In one nonlimiting example, the same design element is present twice in one pattern—the second instance of the design element is smaller than the first instance. One of skill in the art will recognize that alternative arrangements are also possible. Design elements may comprise insignia. Design elements and/or combinations of design elements may comprise letters, words and/or graphics such as flowers, butterflies, hearts, character representations and the like. Design elements may be formed from bonds, including the shape of one or more bond(s). Design elements and/or combinations of design elements may comprise instructional indicia providing guidance or instruction to the caregiver relative to placement and/or fit of the article about the wearer.

"Pattern" as used herein means a decorative or distinctive design, not necessarily repeating or imitative, including but not limited to the following: clustered, geometric, spotted, helical, swirl, arrayed, textured, spiral, cycle, contoured, laced, tessellated, starburst, lobed, blocks, pleated, concave, convex, braided, tapered, and combinations thereof. In some embodiments, the pattern includes one or more repeating design elements.

"Insignia" as used herein means objects, character representations, words, colors, shapes or other indicia that can be used to distinguish, identify or represent the manufacturer, retailer, distributor or brand of a product, including but not limited to trademarks, logos, emblems, symbols, designs, figures, fonts, lettering, crests or similar identifying marks.

The terms "registration process," "registration system," "registration," "register," "registered," or "registering" as used herein refer to a machine control process or system for controlling a substrate or laminate, (which can have multiplicity of pre-produced objects, such as graphics, bonds, patterns, design elements, and/or insignia spaced on the substrate or laminate at a pitch interval that may vary in the machine direction) through a converting line producing articles, by providing a positional adjustment of the pre-produced objects on the substrate or laminate to a target position constant associated with a pitched unit operation of the converting line.

The present disclosure relates to apparatuses and methods for manufacturing absorbent articles, and more particularly, apparatuses and methods for assembling elastic laminates that may be used to make absorbent article components. Particular aspects of the present disclosure involve methods for assembling an elastic laminate including a first substrate and a second substrate with a first elastic material and a second elastic material bonded between the first substrate and the second substrate. In addition, some configurations of the elastic laminates may include one or more reinforcement layers positioned between unstretched portions of the elastic materials and the substrates. It is to be appreciated that in some configurations, the first and/or second elastic materials may be elastic films and/or elastic laminates, and in some configurations, the first and/or second substrates and/or reinforcement layers may be nonwovens. The first and second elastic materials are separated from each other in a cross direction and each include a first edge region and a second edge region separated from the first edge region in the cross direction by a central region, wherein the central regions are stretched in the cross direction. During assembly, an elastic laminate may be formed by positioning the first and second substrates in contact with stretched central regions of the first and second elastic materials. As discussed in more detail below, the elastic laminate may include two or more bonding regions that may be defined by the various layers or components of the elastic laminate that are laminated or stacked relative to each other. In some configurations, a first bonding region is defined where the stretched central region of the first or second elastic film is in direct contact with the first substrate and the second substrate, and at least a second bonding region is positioned completely outside the first bonding region. In turn, a first plurality of bonds are applied to the elastic laminate to define a first bond density in the first bonding region, and a second plurality of bonds are applied to the elastic laminate to define a second bond density in the second bonding region, wherein the second bond density may not be equal to the first bond density. In some configurations, the first bond density may be equal to the second bond density and wherein at least one of the first plurality of bonds may define a shape that is different from a shape of at least one of the second plurality of bonds. After bonding, the elastic laminate may also be cut along the machine direction to form a first elastic laminate and a second elastic laminate. It is to be appreciated that the bonds described herein may be created with various types of method and apparatus configurations, such as for example, adhesives, thermal bonding, ultrasonic bonding, and/or high pressure bonding that may utilize non-heated or heated rolls.

It is to be appreciated that the elastic laminates herein may include two or more bonding regions that may be defined in various ways depending on how the elastic laminate is constructed. For example, in some configurations, a bonding region may be defined where the first substrate is in direct contact with the second substrate. In some elastic laminates, the first edge region and/or the second edge region of the first and/or second elastic materials may be unstretched when positioned in direct contact with both the first and second substrates. As such, a bonding region may be defined where an unstretched edge region of an elastic material is in direct contact with either or both the first substrate and the second substrate. As previously mentioned, in some elastic laminates, the first edge region and/or the second edge region of the first and/or second elastic materials may be unstretched when positioned in direct contact with reinforcement layers and/or the first and/or second substrates. Thus, a bonding region may be defined where a reinforcement layer is in direct contact with an unstretched edge region of an elastic material and either the first substrate or the second substrate. In addition, a bonding region may also be defined where the reinforcement layer is in direct contact with both the first substrate and the second substrate. As such, the methods and apparatuses herein may be configured to apply pluralities of bonds with different bond densities in different bonding regions of the elastics laminates during the assembly process. It is also to be appreciated that the methods and apparatuses herein may be configured to apply pluralities of bonds with equal bond densities in different bonding regions of the elastics laminates during the assembly process wherein one bonding region includes at least one bond defining a shape that is different from a shaped defined by at least one bond in another bonding region. Thus, different bonding configurations may be used to bond nonwovens to each other and/or to unstretched portions of the films may that might not otherwise be suitable for bonding stretchable portions of films to the nonwovens and/or may detract from the desired stretch properties, aesthetic appearance, and/or tactile impression of the assembled elastic laminate. For example, relatively high bond densities may be used when bonding nonwovens to each other and/or to unstretched portions of the films to help ensure the elastic films and nonwovens remain secured to each other during use, whereas relatively low bond densities may be used when bonding nonwovens to stretched portions of the films to help maintain desired stretchability characteristics of the elastic laminate.

It is to be appreciated that various configurations and arrangements of apparatuses may be used to assemble elastic laminates in accordance with the methods herein. For example, the apparatuses and methods disclosed in U.S. patent application Ser. No. 62/374,010, filed on Aug. 12, 2016, and U.S. Patent Application No. 62/406,025, filed on Oct. 10, 2016, may be configured to assemble elastic laminates having various bonding configurations such as described herein. To help provide additional context to the subsequent discussion of elastic laminates and assembly configurations, the following provides a description of an apparatus that may be configured to operate in accordance with the methods disclosed herein.

FIGS. 1A-1D show schematic side views of an apparatus 100 that may be configured to assemble the elastic laminates herein. As shown in FIGS. 1A-1D, the apparatus includes an anvil 102 having a cylindrically-shaped outer circumferential surface 104 and adapted to rotate in a first direction Dir1 about a first axis of rotation 106. Although the first direction Dir1 is depicted in FIG. 1A as clockwise, it is to be appreciated that the anvil 100 may be configured to rotate such that the first direction Dir1 is counterclockwise. The anvil roll 102 may extend axially for a length between a first end 108 and a second end 110. As discussed in more detail below, substrates, reinforcement layers, and elastic materials may be combined on the rotating anvil 102 to form at least one elastic laminate. It is to be appreciated that the substrates, the reinforcement layers, and the elastic materials herein may be configured in various ways. For example, the substrates and/or reinforcement materials may be configured as nonwovens, and the elastic materials may be configured as elastic films and/or elastic laminates. As shown in FIG. 1B, the anvil 102, and more particularly, the outer circumferential surface 104 may also be fluidly connected with a vacuum pressure source 105. As such, vacuum air pressure may be used to help hold the substrates, reinforcement layers, and elastic materials onto the outer circumferential surface 104 of the anvil 102 during operation. Rejects and/or line stops may also be trigged by a vacuum sensor operatively connected to anvil 102.

With continued reference to FIGS. 1A-1D, the apparatus 100 may also include a first spreader mechanism 112 and a second spread mechanism 114. As discussed in more detail below, the first and second spreader mechanisms 112, 114 operate to stretch elastic materials during the elastic laminate assembly process, and the stretched elastic materials are advanced from the spreader mechanisms 112, 114 onto substrates on the rotating anvil 102. As shown in FIG. 1A, the first spreader mechanism 112 may be angularly displaced from the second spreader mechanism 114 with respect to the first axis of rotation 106. As shown in FIG. 1B, the first spreader mechanism 112 may also be axially displaced from the second spreader mechanism 114 along the first axis of rotation 106.

As shown in FIGS. 1A-1F, each spreader mechanism 112, 114 includes a first disk 116 and a second disk 118, wherein the first disk 116 is displaced from the second disk 118 along the axis of rotation 106. The first disk 116 is adapted to rotate about an axis of rotation 116a and the second disk 118 is adapted to rotate about an axis of rotation 118a, wherein the first and second disks 116, 118 rotate in a second direction Dir2 that is opposite the first direction Dir1. Although the second direction Dir2 is depicted in FIG. 1A as counterclockwise, it is to be appreciated that the disks 116, 118 may be configured to rotate such that the second direction Dir2 is clockwise. In addition, the first disk 116 includes an outer rim 116b extending axially between an inner edge 116c and an outer edge 116d, and the second disk 118 includes an outer rim 118b extending axially between an inner edge 118c and an outer edge 118d.

As shown in FIGS. 1A, 1B, 1E, and 1F, the first disk 116 and the second disk 118 are canted relative to each other such that the outer rims 116b, 118b are separated from each other by a distance D that increases from a minimum distance Dmin at a first location 120 to a maximum distance Dmax at a second location 122. As discussed below, elastic materials, such as elastic films, are advanced in a machine direction MD onto the outer rims 116b, 118b during operation. Because the first and second disks 116, 118 are canted, rotation of the disks 116, 118 causes the rims 116b, 118b to pull on edge regions of elastic materials and stretch the elastic materials in a cross direction CD before the elastic materials advance onto the anvil 102. As such, the disks 116, 118 may also be configured to help grip opposing edge regions of the elastic material during operation. For example, with particular reference to FIGS. 1E and 1F, the first disk 116 and the second disk 118 may each include a channel 124 extending radially inward from the rims 116b, 118b. In turn, the channels 124 may be fluidly connected with a vacuum pressure source 129.

Figures 1C, 1D:
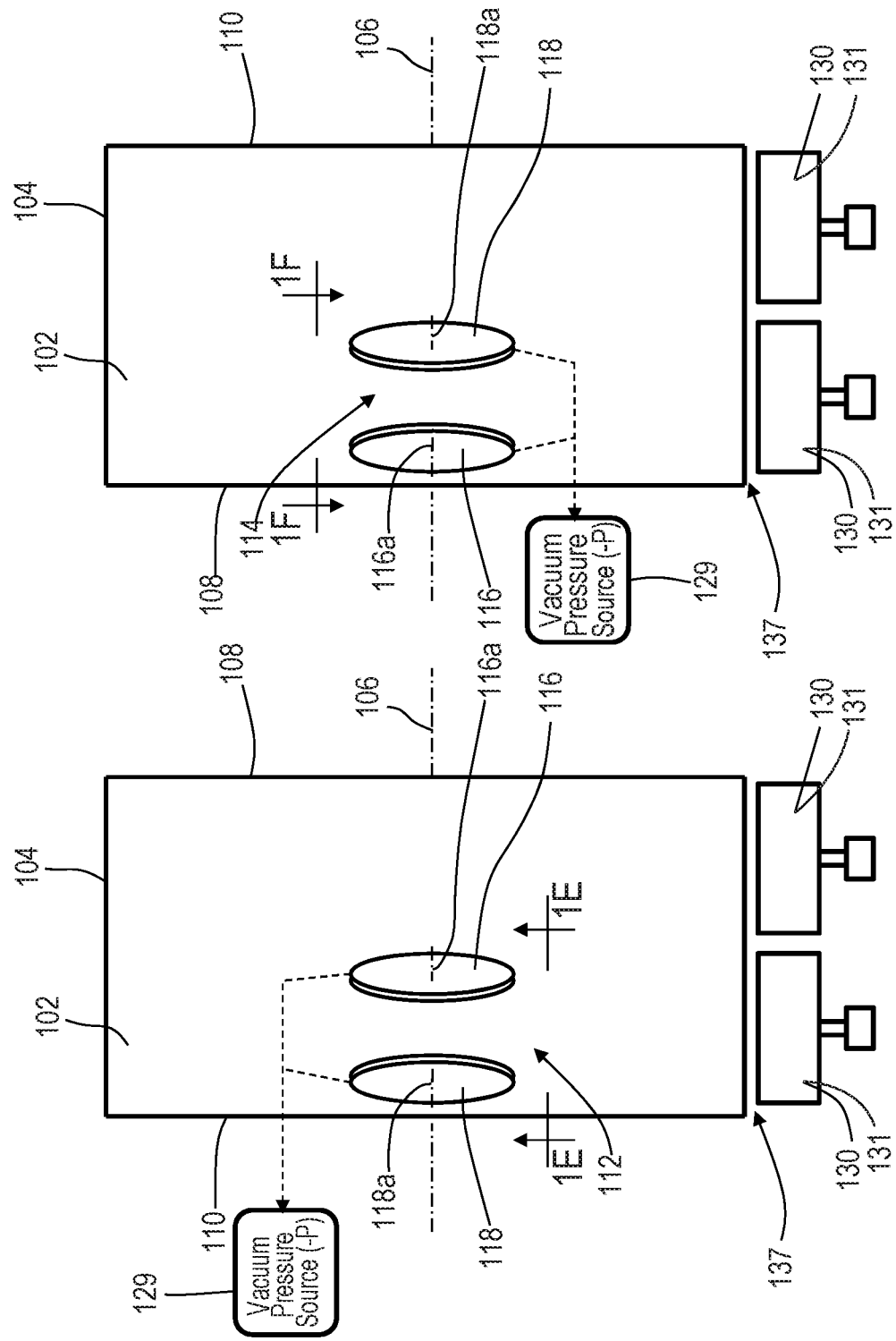
FIG. 1C is a left side view of the apparatus from FIG. 1B taken along line 1C-1C.
FIG. 1D is a right side view of the apparatus from FIG. 1B taken along line 1D-1D.
Figure 1E:
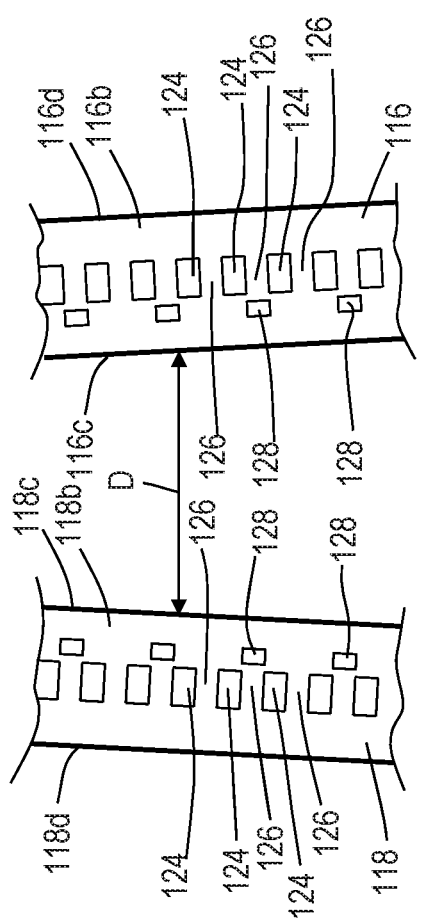
FIG. 1E is a detailed view of a first spreader mechanism from FIG. 1C taken along line 1E-1E.
Figure 1F:
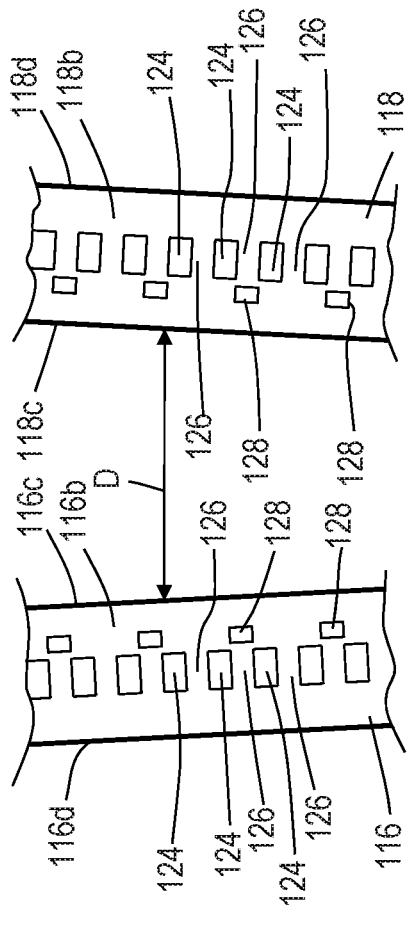
FIG. 1F is a detailed view of a second spreader mechanism from FIG. 1D taken along line 1F-1F.
Figure 1G:
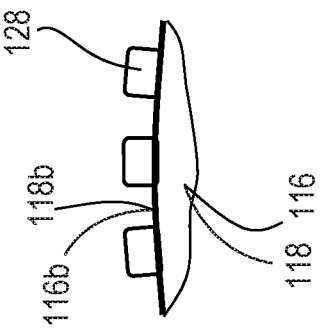
FIG. 1G is a detailed view of radially protruding nubs on an outer rim of a disk.

As such, vacuum air pressure may be used to help hold the elastic materials onto the rims 116b, 118b during operation. Rejects and/or line stops may also be trigged by a vacuum sensor operatively connected to spreader disks 116, 118. The disks 116, 118 may also include support members 126 extending across the channels 124 to the help prevent the elastic materials from being drawn into the channels 124 by the vacuum air pressure. As shown in FIGS. 1E, 1F, and 1G, the disks 116, 118 may also include nubs 128 that protrude radially outward from the rims 116b, 118b. As such, the nubs 128 may also act to help prevent the edge regions of the elastic materials from sliding along the rims 116b, 118b while stretching the elastic materials. It is to be appreciated that additional nubs 128 may be positioned inboard or outboard of the channels 124. In addition, nubs 128 may also be positioned on the support members 126.

Figure 1H:
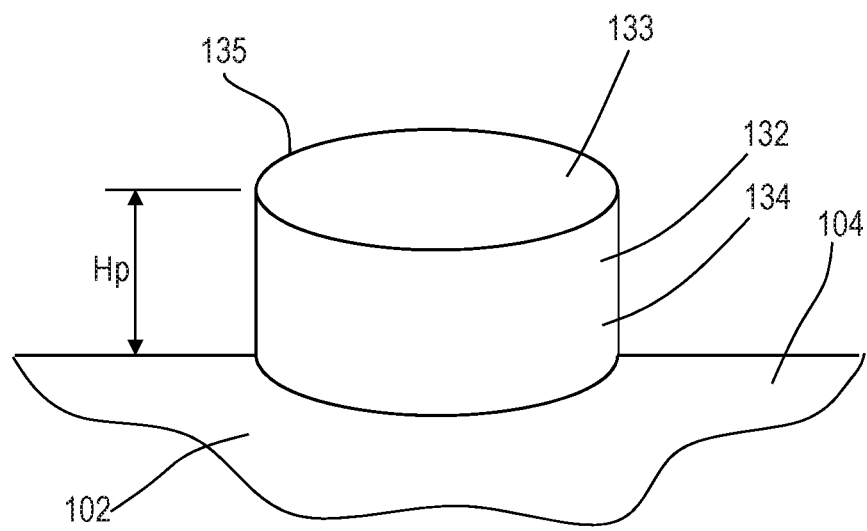
FIG. 1HA is a detailed cross sectional view of an anvil from FIG. 1B showing bonding elements extending radially outward from an outer circumferential surface taken along line 1HA-1HA.

As mentioned above, stretched elastic materials, reinforcement layers, and substrates may be combined on the anvil 102 to form elastic laminates having two or more bonding regions. The assembled components of the elastic laminates may then be bonded together on the anvil 102 in the bonding regions. As shown in FIGS. 1A, 1C, and 1D, the apparatus 100 may include one or more ultrasonic mechanisms 130 adjacent the anvil 102. It is to be appreciated that the ultrasonic mechanism 130 may include a horn 131 and may be configured to impart ultrasonic energy to the combined substrates and elastic materials on the anvil 102. As shown in FIGS. 1HA and 1HB, the anvil roll 102 may include a plurality of bonding elements 132 extending radially outward from the outer circumferential surface 104 of the anvil 102. As such, the ultrasonic mechanism may apply energy to the horn 131 to create resonance of the horn at frequencies and amplitudes so the horn 131 vibrates rapidly in a direction generally perpendicular to the substrates and elastic materials being advanced past the horn 131 on the rotating anvil 102. Vibration of the horn 131 generates heat to melt and bond the substrates, reinforcement layers, and elastic materials together in areas supported by the bonding elements 132 on the anvil 102. It is to be appreciated that aspects of the ultrasonic mechanisms may be configured in various ways, such as disclosed for example in U.S. Pat. Nos. 3,113,225; 3,562,041; 3,733,238; 6,036, 796; 6,508,641; and 6,645,330. In some configurations, the ultrasonic mechanism may be configured as a linear oscillating type sonotrode, such as for example, available from Herrmann Ultrasonic, Inc. In some configurations, the sonotrode may include a plurality of sonotrodes nested together in the cross direction CD.

Although the apparatus 100 is illustrated as including an ultrasonic mechanism 130, it is to be appreciated that that apparatus 100 may be configured to bond assembled components of the elastic laminates together in various ways. For example, the apparatus 100 may be configured to bond components of the elastic laminates together with adhesives, thermal bonding, ultrasonic bonding, and/or high pressure bonding that may utilize non-heated or heated rolls. Example methods and apparatuses that may be used to bond the elastic laminates herein are disclosed in U.S. Pat. Nos. 4,854,984 and 6,248,195 and U.S. Patent Publication Nos. 2013/0218116 A1; 2013/0213547 A1; 2014/0377513 A1; and 2014/0377506 A1.

As shown in FIGS. 1HA-1HC, the bonding elements 132 protrude radially outward from the anvil roll 102, wherein each bonding element 132 includes a bonding surface 133. In particular, each bonding element 132 includes a circumferential wall 134 that protrudes radially outward from the outer circumferential surface 104 of the anvil roll 102 to define a distance, Hp, between the bonding surface 133 and the outer circumferential surface 104. The circumferential wall 134 also defines an outer perimeter 135 of the bonding element 132 and bonding surface 133. It is to be appreciated that in some embodiments, the circumferential wall 134 may be perpendicular to outer circumferential surface 104 or may sloped or tapered with respect to the outer circumferential surface 104.

It is also to be appreciated that the anvil roll 102 may be configured with bonding elements 132 and/or bonding surfaces 133 having different sizes and shapes. For example, in some embodiments, the bonding elements 132 and/or bonding surfaces 133 may have perimeters 135 that define circular shapes, square shapes, rectangular shapes, diamond shapes, elliptical shapes, and various types of other shapes. The bonding elements 132 and/or bonding surfaces 133 may also be arranged with various sized gaps or distances between each other. The bonding surfaces 133 may also be configured to define various different areas and may also be configured to include channels. Additional configurations of bonding elements that may be used with the apparatuses and methods herein are disclosed in U.S. Patent Publication Nos. 2014/0377513 A1 and 2014/0377506 A1.

As shown in FIGS. 1A, 1C, and 1D, the anvil roll 102 is adjacent the horn 131 so as to define a nip 137 between the anvil roll 102 and the horn 131, and more particularly, to define a nip 137 between the bonding surfaces 133 of each bonding element 132 and the horn 131. During the bonding process, it is to be appreciated that bonds imparted into an elastic laminate may correspond with patterns and/or shapes defined by the plurality of bonding surfaces 133. As such, pluralities of bonding elements 132 may be arranged in two or more lanes extending circumferentially along the outer circumferential surface 104 of the anvil 102 and having various axial or cross directional widths. As discussed below, the two or more lanes may be arranged and configured to create pluralities of bonds in two or more corresponding bonding regions in the elastic laminate.

It is to be appreciated that the anvil may be configured with various numbers of lanes of bonding elements 132 and bonding surfaces 133 configured in various ways. For example, as shown in FIGS. 1HA and 1HB, the anvil 102 may include nine lanes L1-L9, wherein each lane includes a plurality of bonding elements 132. Each lane L1-L9 may extend for lengths along the outer circumferential surface 104 that extend less than or completely around the axis of rotation 106. Each lane L1-L9 may also define various axial or cross directional CD widths. For the purposes of clarity, dashed lines are shown in FIGS. 1HA and 1HB to represent example boundaries between the lanes L1-L9. It is to be appreciated that such boundaries between the lanes L1-L9 can also be curved, angled, and/or straight with respect to the cross direction CD. It is to be appreciated that bonding elements 132 within each of the lanes L1-L9 may be configured with the same or different quantities of bonding surfaces 133 having the same or different shapes, sizes, orientations, areas and/or distances between bonding surfaces. It is also to be appreciated that the lanes L1-L9 may include the same or different quantities of bonding elements 132 and that any of the lanes may include bonding surfaces 133 with shapes, sizes, orientations, areas, and/or distances between bonding surfaces that is the same or different from shapes, sizes, orientations, areas, and/or distances between bonding surfaces of bonding surfaces 133 included in other lanes. As such, a plurality of bonding surfaces in any one lane may be arranged to apply bonds to a substrate advancing between the anvil and the ultrasonic horn at a bond density that may be less than, equal to, or greater than a bond density defined by bonds created by a plurality of bonding surfaces in another lane.

Figure 2A:
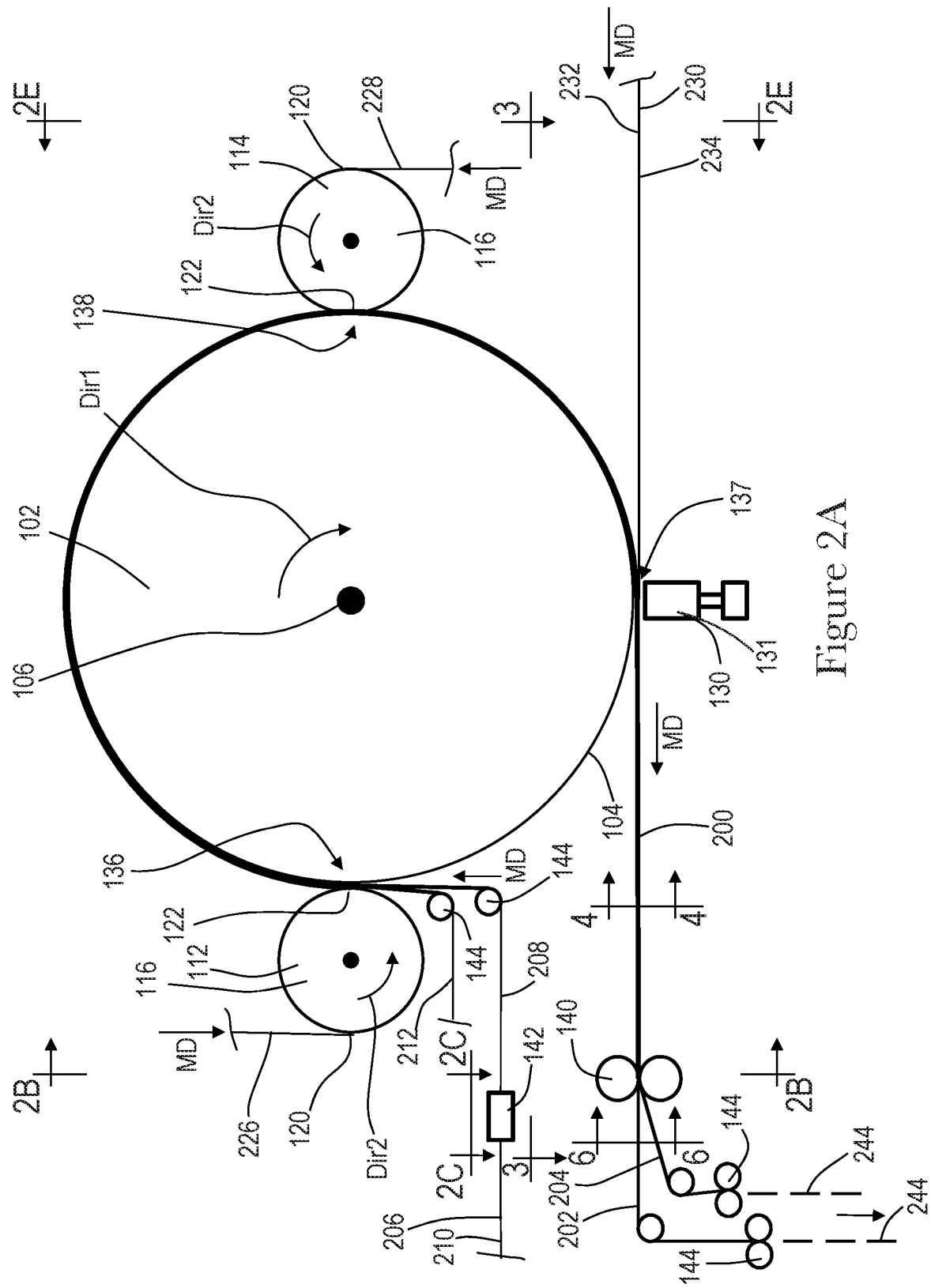
FIG. 2A is a schematic side view of an apparatus operating to assemble elastic laminates.
Figure 2C:
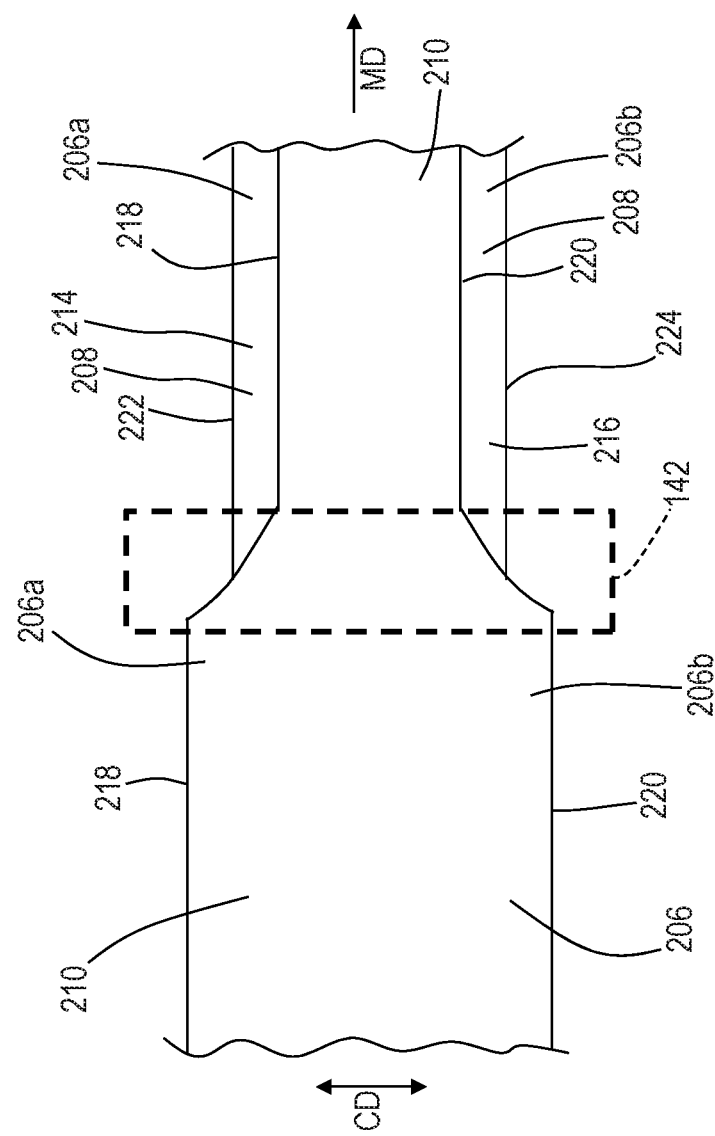
FIG. 2C is a top side view of the first substrate advancing through a folding apparatus from FIG. 2A taken along line 2C-2C.
Figure 3:
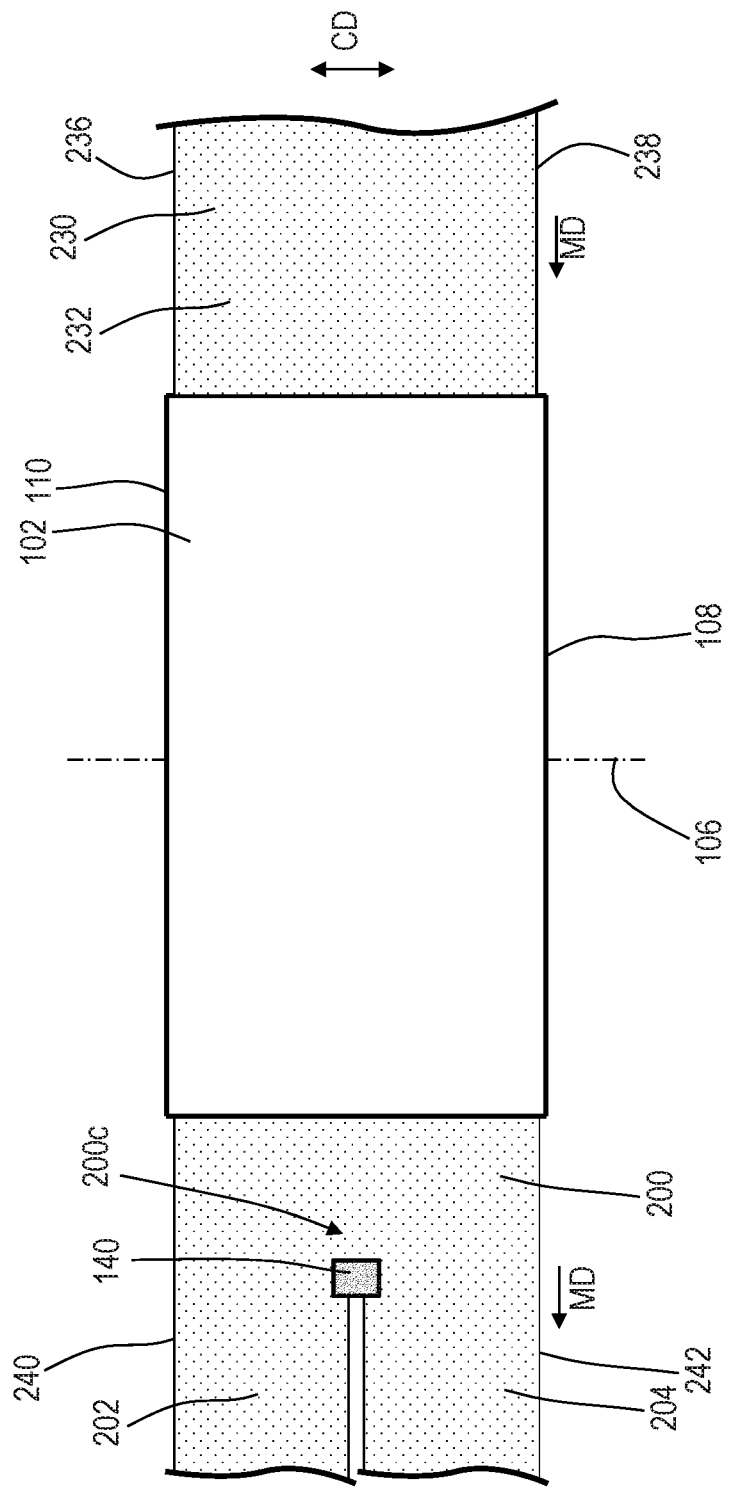
FIG. 3 is a top side view of an elastic laminate and apparatus from FIG. 2A taken along line 3-3.

As previously mentioned, the apparatus 100 described above with reference to FIGS. 1A-1HC may operate to assemble elastic laminates configured in various ways. For example, FIGS. 2A-3 show various schematic views of the apparatus 100 operating to assemble an elastic laminate 200 that is subsequently slit along the machine direction MD into a first elastic laminate 202 and a second elastic laminate 204. The first substrate 202 and/or the second substrate 204 may also advance through a cutter 144, such as a knife, that cuts and/or separates the first substrate 202 and/or the second substrate 204 along the cross direction CD into discrete parts or pieces 244.

As shown in FIGS. 2A and 2B, a first substrate 206 advances in a machine direction MD onto the rotating anvil 102. More particularly, the first substrate 206 includes a first surface 208 and an opposing second surface 210, and the first substrate 206 advances to wrap the first surface 208 onto the outer circumferential surface 104 of the rotating anvil 102. As shown in FIGS. 2A and 2B, a first reinforcement layer 212 is advanced onto the second surface 210 of the first substrate 206. It is to be appreciated that the first reinforcement layer 212 may be formed in various ways. For example, the first reinforcement layer 212 is depicted as a discrete strip of material advanced onto the first substrate 206. With continued reference to FIG. 2B, a second reinforcement layer 214 and a third reinforcement layer 216 may also advance with the first substrate 206 onto the anvil roll 102. It is also to be appreciated that the first substrate 206 and/or the reinforcement layers 212, 214, 216 may also advance around guide rollers 144 such as shown in FIGS. 2A and 2B before advancing onto the anvil roll 102.

It is also to be appreciated that the second and third reinforcement layers 214, 216 may be formed in various ways. For example, as shown in FIG. 2C, the first substrate 206 may advance through a folding apparatus 142 that operates to fold portions of the first substrate 206 to create the second and third reinforcement layers 214, 216. In some configurations such as shown in FIG. 2C, the folding apparatus 142 may operate to fold a first longitudinal edge 218 and/or a second longitudinal edge 220 of the first substrate 206 laterally inward in the cross direction CD. More particularly, the folding apparatus 142 may fold the first substrate 206 to position a first portion 206a and a second portion 206b of the second surface 210 of the first substrate 206 in a facing relationship with the second surface 210 of the first substrate 206. As such, the folding apparatus 142 creates a first fold line 222 and a second fold line 224 in the first substrate 206 that extend in the machine direction MD. In turn, the second reinforcement layer 214 may be defined by the first portion 206a of the first substrate 206 extending between the first fold line 222 and the first longitudinal edge 218, and the third reinforcement layer 216 may be defined by the second portion 206b of the first substrate 206 extending between the second fold line 224 and the second longitudinal edge 220.

With continued reference to FIGS. 2A and 2B, during the assembly process, a first elastic material 226 is stretched in the cross direction CD and is positioned into contact with the second surface 210 of the first substrate 204, the first reinforcement layer 212, and the second reinforcement layer 214. With particular reference to FIG. 2D, the first elastic material 226 includes a first edge region 226a and a second edge region 226b separated from the first edge region 226a in the cross direction CD by a central region 226c. As shown in FIG. 2A, the first elastic material 226 advances in a machine direction MD onto the first spreader mechanism 112 at or downstream of the first location 120. In particular, the first edge region 226a of the first elastic material 226 advances onto the outer rim 116b of the first disk 116 of the first spreader mechanism 112, and the second edge region 226b advances onto the outer rim 118b of the second disk 118. As previously discussed with reference to FIG. 1E, the outer rims 116b, 118b of the first and second disks 116, 118 of the first spreader mechanism 112 may include channels 124 fluidly connected to a vacuum pressure source 129 and may include radially protruding nubs 128. Thus, as shown in FIG. 2D, the first edge region 226a of the first elastic material 226 may be held in position on the outer rim 116b with vacuum air pressure in the channels 124 and with the radially protruding nubs 128. Similarly, the second edge region 226b of the first elastic material 226 may be held in position on the outer rim 118b with vacuum air pressure in the channels 124 and with the radially protruding nubs 128.

With continued reference to FIG. 2D, as the first disk 116 and the second disk 118 of the first spreader mechanism 112 rotate, the central region 226c of the first elastic material 226 is stretched in the cross direction CD. Because the first and second edge regions 226a, 226b are held in position on the outer rims 116b, 118b, some portions of the first and second edge regions 226a, 226b may remain unstretched in the cross direction CD as the first and second disks 116, 118 rotate. Referring now to the FIGS. 2A and 2B, the first elastic material 226 advances from the first spreader mechanism 112 and is transferred onto the second surface 210 of the first substrate 206 on the anvil 102 at a first application zone 136. In particular, the stretched central region 226c of the first elastic material 226 is positioned in direct contact with the second surface 210 of the first substrate 206. In addition, the first reinforcement layer 212 is positioned between and in direct contact with the second surface 210 of the first substrate 206 and the first edge region 226a of the first elastic material 226. The second reinforcement layer 214 is also positioned between and in direct contact with the second surface 210 of the first substrate 206 and the second edge region 226b of the first elastic material 226, wherein the first longitudinal edge 218 of the first substrate 206 is positioned between the second edge region 226b of the first elastic material 226 and second surface 210 of the first substrate 206.

It is to be appreciated that during the transfer from the first spreader mechanism 112 to the anvil 102, the first elastic material 226 may be removed from the first spreader mechanism 112 at or upstream of the second location 122. As previously mentioned, the outer circumferential surface 104 of the anvil 102 may be fluidly connected with the vacuum source 105, and as such, vacuum air pressure may be applied to the first substrate 206 on the anvil 102. In addition, when the first substrate 206 is configured as a porous substrate, such as a nonwoven, vacuum air pressure may also be applied to the first elastic material 226 on the anvil 102, and as such, may help maintain the stretched condition of the central region 226c of the first elastic material 216 while on the anvil 102.

Referring now to FIGS. 2A and 2F, during the assembly process, a second elastic material 228 is stretched in the cross direction CD and is positioned into contact with the second surface 210 of the first substrate 206. With particular reference to FIG. 2F, the second elastic material 228 includes a first edge region 228a and a second edge region 228b separated from the first edge region 228a in the cross direction CD by a central region 228c. As shown in FIG. 2A, the second elastic material 228 advances in a machine direction MD onto the second spreader mechanism 114 at or downstream of the first location 120. In particular, the first edge region 228a of the second elastic material 228 advances onto the outer rim 116b of the first disk 116 of the second spreader mechanism 114, and the second edge region 228b advances onto the outer rim 118b of the second disk 118. As previously discussed with reference to FIG. 1F, the outer rims 116b, 118b of the first and second disks 116, 118 of the second spreader mechanism 114 may include channels 124 fluidly connected to a vacuum pressure source 129 and may include radially protruding nubs 128. Thus, as shown in FIG. 2F, the first edge region 228a of the second elastic material 228 may be held in position on the outer rim 116b with vacuum air pressure in the channels 124 and with the radially protruding nubs 128. Similarly, the second edge region 228b of the second elastic material 228 may be held in position on the outer rim 118b with vacuum air pressure in the channels 124 and with the radially protruding nubs 128. It is to be appreciated that such nubs 128 may be formed in a metal disc, such as by laser, water jet cutting, or other common machining processes. In addition, such nubs 128 and/or vacuum channels 124 may be formed with an additive manufacturing process, such as SLA, FDM, or selective laser sintering With continued reference to FIG. 2F, as the first disk 116 and the second disk 118 of the second spreader mechanism 114 rotate, the central region 228c of the second elastic material 228 is stretched in the cross direction CD. Because the first and second edge regions 228a, 228b are held in position on the outer rims 116b, 118b, some portions of the first and second edge regions 228a, 228b may remain unstretched in the cross direction CD as the first and second disks 116, 118 rotate. Referring now to the FIGS. 2A and 2E, the second elastic material 228 advances from the second spreader mechanism 114 and is transferred onto the second surface 210 of the first substrate 206 on the anvil 102 at a second application zone 138. In particular, the stretched central region 228c of the second elastic material 228 is positioned in direct contact with the second surface 210 of the first substrate 206. In addition, the first reinforcement layer 212 is positioned between and in direct contact with the second surface 210 of the first substrate 206 and the second edge region 228b of the second elastic material 228. The third reinforcement layer 216 is positioned between and in direct contact with the second surface 210 of the first substrate 206 and the first edge region 228a of the second elastic material 228, wherein the second longitudinal edge 220 of the first substrate 206 is positioned between the first edge region 228a of the second elastic material 228 and second surface 210 of the first substrate 206.

As previously mentioned, the first spreader mechanism 112 may be angularly displaced from the second spreader mechanism 114 with respect to the first axis of rotation 106. As such, the second application zone 138 is positioned downstream of the first application zone 136. It is to be appreciated that during the transfer from the second spreader mechanism 114 to the anvil 102, the second elastic material 218 may be removed from the second spreader mechanism 114 at or upstream of the second location 122. As previously mentioned, the outer circumferential surface 104 of the anvil 102 may be fluidly connected with the vacuum source 105, and as such, vacuum air pressure may be applied to the first substrate 206 on the anvil 102. In addition, when the first substrate 206 is configured as a porous substrate, such as a nonwoven, vacuum air pressure may also be applied to the second elastic material 228 on the anvil 102, and as such, may help maintain the stretched condition of the central region 228c of the second elastic material 228 while on the anvil 102. Also, as shown in FIG. 2E, the second elastic material 228 may be axially separated or spaced from the first elastic material 226 in the cross direction CD such that a cross directional gap exists between the first elastic material 226 and the second elastic material 228.

As shown in FIGS. 2A, 2B, and 2E, an elastic laminate 200 may be formed by combining a second substrate 230 together with the first substrate 206, the first elastic material 226, the second elastic material 228, and the reinforcement layers 212, 214, 216 on the anvil 102. The elastic laminate 200 includes a first edge 240 separated from a second edge 242 in the cross direction CD. The second substrate 230 includes a first surface 232 and an opposing second surface 234 as well as a first longitudinal edge 236 that is separated from a second longitudinal edge 238 in the cross direction CD. The second substrate 230 advances to position the first surface 232 in contact with first elastic material 226, the second elastic material 228, the reinforcement layers 212, 214, 216, and the second surface 210 of the first substrate 206. In particular, the first edge region 226a of the first elastic material 226 and the second edge region 228b of the second elastic material 228 are positioned between the first reinforcement layer 212 and the first surface 232 of the second substrate 230. In addition, a central portion of the first reinforcement layer 212 between the first and second elastic materials 226, 228 is positioned between and in direct contact with the second surface 210 of the first substrate 206 and the first surface 232 of the second substrate 230. The first surface 232 of the second substrate 230 is also positioned in direct contact with the stretched central region 226c of the first elastic material 226 and the stretched central region 228c of the second elastic material 228. Further, the second edge region 226b of the first elastic material 226 is positioned between and in direct contact with the second reinforcement layer 214 and the first surface 232 of the second substrate 230. And the first edge region 228a of the second elastic material 228 is positioned between and in direct contact with the third reinforcement layer 216 and the first surface 232 of the second substrate 230.

As the anvil 102 rotates, the elastic laminate 200 including the first substrate 234, the first elastic material 216, the second elastic material 218, the second substrate 230, and the reinforcement layers 212, 214, 216 is advanced through the nip 137 between the bonding surfaces 133 on the anvil 102 and the ultrasonic horn 131. In turn, the ultrasonic horn 131 bonds the first substrate 206, the first elastic material 226, the second substrate 230, the first reinforcement layer 212, and the second reinforcement layer 214 together and also bonds the first substrate 206, the second elastic material 228, the second substrate 230, the first reinforcement layer 212, and the third reinforcement layer 216 together, such as shown in FIGS. 4 and 5.

It is to be appreciated that the elastic laminate 200 may include various portions of components bonded together in various ways and with bonds 300 having differing or identical bond patterns. For example, the unstretched portion of the first edge region 226a of the first elastic material 226 may be bonded together with the first substrate 206, the first reinforcement layer 212, and/or the second substrate 230. And similarly, the unstretched portion of the second edge region 228b of the second elastic material 228 may be bonded together with the first substrate 206, the first reinforcement layer 212, and/or the second substrate 230. The unstretched portion of the second edge region 226b of the first elastic material 226 may be bonded together with the first substrate 206, the second reinforcement layer 214, and/or the second substrate 230. And similarly, the unstretched portion of the first edge region 228a of the second elastic material 228 may be bonded together with the first substrate 206, the third reinforcement layer 216, and/or the second substrate 230. In addition, the stretched central region 226c of the first elastic material 226 may be bonded together with the first and/or second substrates 206, 230. Further, the stretched central region 228c of the second elastic material 228 may be bonded together with the first and/or second substrates 206, 230. Further, the first substrate 206 may be bonded directly to the second substrate 230 in areas of the elastic laminate 200. It is to be appreciated that the apparatus 100 may be adapted to create various types of bond configurations, such as disclosed, for example, in U.S. Pat. No. 6,572,595.

As previously mentioned above with reference to FIGS. 1HA and 1HB, the anvil 102 may include pluralities of bonding elements 132 that may be arranged and configured to create pluralities of bonds 300 in the elastic laminate 200. During the bonding process, it is to be appreciated that bonds 300 imparted into the elastic laminate 200 may correspond with patterns and/or shapes defined by the plurality of bonding surfaces 133 of the anvil 102. As such, the bonds 300 may have different sizes and shapes. For example, in some embodiments, the bonds 300 may define circular shapes, square shapes, rectangular shapes, elliptical shapes, diamond shapes, and various types of other shapes. The bonds 300 may also be arranged with various sized gaps or distances between other. The bonds 300 may also define various different areas. Additional configurations and arrangements of bonds are disclosed in U.S. Patent Publication Nos. 2014/0377513 A1 and 2014/0377506 A1.

Figure 6:
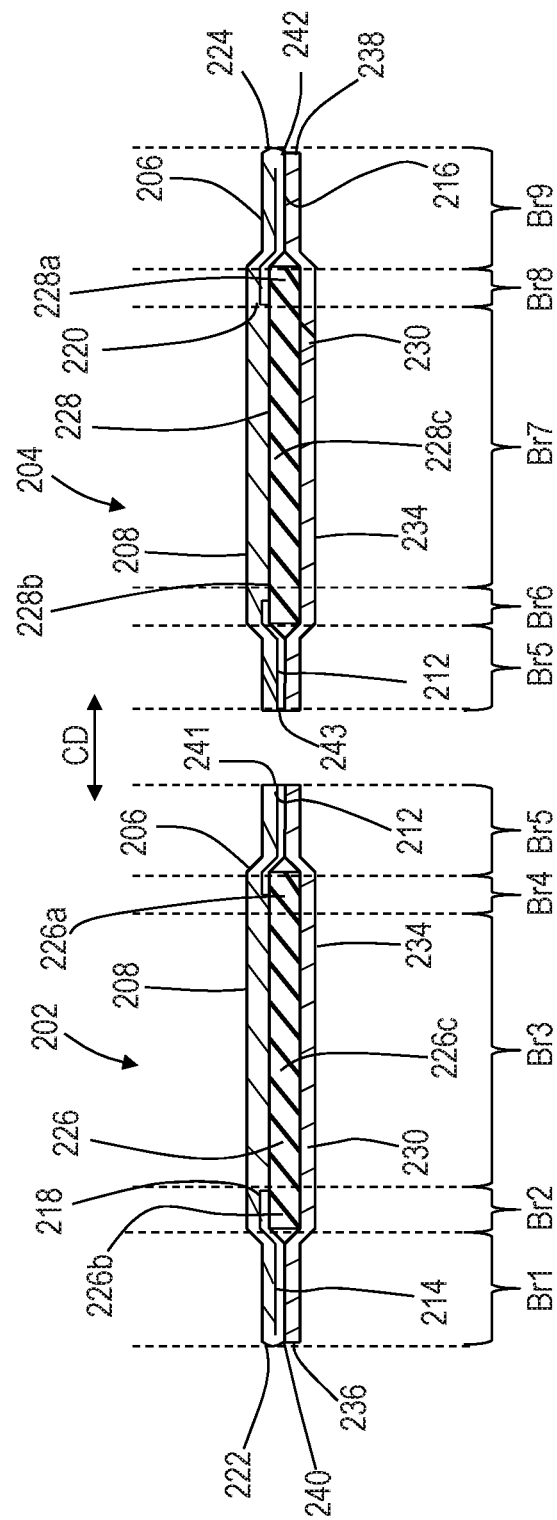
FIG. 6 is a cross sectional view of a first elastic laminate and a second elastic laminate from FIG. 2A taken along line 6-6.

As shown in FIGS. 2A and 6, the elastic laminate 200 may then advance from the anvil 102 to a cutter 140. In turn, the cutter 140 separates the elastic laminate 200 into the first elastic laminate 202 and the second elastic laminate 204. Thus, the first elastic laminate 202 includes a first edge 240 separated from a second edge 241 in the cross direction CD, and the second elastic laminate 204 includes a first edge 243 separated from a second edge 242 in the cross direction CD. It is to be appreciated that the cutter 140 may be configured in various ways. For example, in some embodiments the cutter 140 may be a slitter or a die cutter that separates the elastic laminate 200 into the first elastic laminate 202 and the second elastic laminate 204. The cutter 140 may cut through the first substrate 206, the first reinforcement layer 212, and the second substrate 230 with either a straight line cut and/or a curved line cut extending in machine direction MD. The cutter 140 may also be configured as a perforator that perforates the elastic laminate 200 with a line of weakness and wherein the elastic laminate 200 is separated along the line of weakness in a later step. It is also to be appreciated that the cutter 140 may be configured to cut elastic laminate 200 into the first and second elastic laminates 202, 204 while the elastic laminate 200 is positioned on the anvil 104.

In some configurations, the cutter 140 may cut the elastic laminate 200, such as shown in FIG. 3 along a line extending in the machine direction MD through a central region or location 200c of the elastic laminate 200. As such, the elastic laminate 200 may be separated into the first elastic laminate 202 and the second elastic laminate 204, such as shown in FIG. 6. After slitting the elastic laminate 200, the first elastic laminate 202 and the second elastic laminate 204 may be allowed to relax or contract in the cross direction CD, wherein the central region 226c of the first elastic material 226 is contracted in the cross direction CD and wherein the central region 228c of the second elastic material 228 is contracted in the cross direction CD. In some configurations, the elastic laminate 200 may be allowed to relax or contract in the cross direction CD before being separated by the cutter 140 into the first elastic laminate 202 and the second elastic laminate 204.

As shown in FIGS. 3 and 4, the central region or location 200c of the elastic laminate 200 may be defined in an area between the first elastic material 226 and the second elastic material 228 where first substrate 206, the first reinforcement layer 212, and the second substrate 230 are bonded directly to each other. As such, slitting the elastic laminate 200 with the cutter 140 along the central region 200c may eliminate the need to also cut through the first elastic material 226 and/or the second elastic material 228 when creating the first and second elastic laminates 202, 204. As such, the slit edges of the first and second elastic laminates 202, 204 may not have exposed elastic material 226, 228 and thus, may be relatively more aesthetically pleasing.

It is to be appreciated that various arrangements of apparatuses may be configured to operate with various process configurations to assemble elastic laminates 200 such as shown in FIG. 4 and wherein the assembly operations may be carried out in various orders and in various ways. For example, as shown in FIG. 4A, the first substrate 206 may be combined with the first reinforcement layer 212, and the first substrate 206 may be folded to define the second and third reinforcement layers 214, 216. The first substrate 206 and reinforcement layers 212, 214, 216 of FIG. 4A may be combined with the first elastic material 226 provided with unstretched edge regions 226a, 226b and the stretched central region 226c such as shown in FIG. 4B1. In addition, the first substrate 206 and reinforcement layers 212, 214, 216 of FIG. 4A may be combined with the second elastic material 228 provided with unstretched edge regions 228a, 228b and the stretched central region 228c such as shown in FIG. 4B1. The first substrate 206, elastic materials 226, 228, and reinforcement layers 212, 214, 216 of FIG. 4B1 may be combined with the second substrate 230 such as shown in FIG. 4C to arrive at the elastic laminate shown in FIG. 4. In some configurations, the first and second elastic materials 226, 228 may be formed after being combined with the first substrate 206 and/or the second substrate 230. For example, the first substrate 206 and reinforcement layers 212, 214, 216 of FIG. 4A may be combined with a single elastic material 227 provided with unstretched edge regions 227a, 227b and a stretched central region 227c such as shown in FIG. 4B2A to arrive at the configuration shown in FIG. 4B2B. The combined first substrate 206 and reinforcement layers 212, 214, 216 and elastic material 227 of FIG. 4B2B may be modified by cutting the elastic material 227 along the stretched central region 227c into the first elastic material 226 and the second elastic material 228. As shown in FIG. 4B2C, regions of the elastic material 227 adjacent the cut may retract in the cross direction CD to define the unstretched first edge region 226a of the first elastic material 226 and the unstretched second edge region 228b of the second elastic material 228. In turn, the first substrate 206, elastic materials 226, 228, and reinforcement layers 212, 214, 216 of FIG. 4B2C may be combined with the second substrate 230, such as shown in FIG. 4C to arrive at the elastic laminate shown in FIG. 4.

It is also to be appreciated that the elastic laminates 200 herein can be configured various different ways with different configurations of the first reinforcement layer 212, the second reinforcement layer 214, and the third reinforcement layer 216. For example, although the second reinforcement layer 214 and the third reinforcement layer 216 may be formed by only folding the first substrate 206 such as described above with reference to FIG. 2C, it is to be appreciated that portions of the second substrate 230 adjacent the first and second edges 236, 238 may also be folded laterally inward in the cross direction CD toward each other in addition to or alternatively to folding the first substrate 206. For example, in some configurations, the second reinforcement layer 214 may be formed by folding a portion of the first substrate 206 and/or the second substrate 230, and the third reinforcement layer 216 may be formed by folding a portion of the first substrate 206 and/or the second substrate 230. For example, the second reinforcement layer 214 may be formed by folding a portion of the first substrate 206 along the first longitudinal edge 218, and the third reinforcement layer 216 may be formed by folding a portion of the second substrate 230 along the second longitudinal edge 238.

It is also to be appreciated that the first reinforcement layer 212, the second reinforcement layer 214, and/or the third reinforcement layer 216 may be formed by discrete strips of material in addition to or alternative to folding portions of the first substrate 206 and/or second substrate 230. For example, the first reinforcement layer 212 may be defined by a first discrete strip of material, the second reinforcement layer 214 may be defined by a second discrete strip of material, and the third reinforcement layer 216 may be defined by a third discrete strip of material. It is to be appreciated that the first reinforcement layer 212 and/or the second reinforcement layer 214 may be positioned between the first elastic material 226 and the first substrate 206 or the second substrate 230; and the first reinforcement layer 212 and/or the third reinforcement layer 216 may be positioned between the second elastic material 228 and the first substrate 206 or the second substrate 230. It is also to be appreciated that the first reinforcement layer 212, the second reinforcement layer 214, and/or the third reinforcement layer 216 may define varying cross directional widths and may be located in various different positions along the cross direction CD within the elastic laminate 200. For example, the second reinforcement layer 214 may not extend in the cross direction entirely to the first edges 218, 236 of the first and second substrates 206, 230, and the third reinforcement layer 216 may not extend in the cross direction entirely to the second edges 220, 238 of the first and second substrates 206, 230. In addition, the first reinforcement layer 212 may be formed by folding a portion of the first substrate 206 and/or the second substrate 230 and/or in combination with a discrete strip of material. For example, the first reinforcement layer 212 may be formed by creating a Z-fold in the first substrate 206 and/or the second substrate 230.

It is also to be appreciated that the first reinforcement layer 212, the second reinforcement layer 214, and/or the third reinforcement layer 216 may be formed from material that is the same or different than the material of the first substrate 206 and/or second substrate 230. In some configurations, the first reinforcement layer 212, the second reinforcement layer 214, and/or the third reinforcement layer 216 may be formed from strips of material cut from the first substrate 206 and/or second substrate 230. It is to be appreciated that the first reinforcement layer 212, the second reinforcement layer 214, and/or the third reinforcement layer 216 may be formed from various types of materials. For example, the reinforcement layer may be a polymeric film layer that is mono-layer or multi-layer. It is to be appreciated that the polymeric material can be crystalline, semi-crystalline, or amorphous. In some configurations, the reinforcement layers may be made with polymers that are compatible with polymers of the first and/or second substrate. In some configurations, polymers may be homopolymers, co-polymers, or block co-polymers. For example, polyolefins may be used. In some configurations, polypropylene homopolymers may be compatible with polypropylene nonwoven substrates used commonly.

Similarly, if the first and/or second substrate is made of polyethylene, then a reinforcement layer may be made with polyethylene. In some configurations, multi-layer film made with polypropylene core and polyethylene skins will bond strongly with polyethylene nonwovens. Polypropylene co-polymers and polyethylene co-polymers may also be suitable polymers for the reinforcement layer. Other polymers that can be used to make reinforcement layers are: styrenic polymers, thermoplastic polyurethanes, polyamids, polylactic acid, polyesters, or blends thereof.

It is to be appreciated that aspects of the methods and/or apparatus 100 herein may be configured to assemble elastic laminates from various types of material and/or components. For example, it is to be appreciated that the first substrate 206, the second substrate 230, the first reinforcement layer 212, the second reinforcement layer 214, and/or the third reinforcement layer 216 may be configured as the same or different types of materials. For example, the substrates 206, 230 and/or the reinforcement layers 212, 214, 216 may be configured as single layer or multi-layer nonwovens. In some examples wherein the elastic laminates 202, 204 may be used to manufacture diaper components, the substrate 206 may define garment facing surfaces of the elastic laminates 202, 204 in diaper components, whereas the substrate 230 may define body facing surfaces of the elastic laminates 202, 204 in diaper components. As such, the substrate 206 may be configured as a relatively high cost, premium material for aesthetic purposes, such as soft feel and appearance. In contrast, the substrate 230 may be configured as a cost optimized nonwoven, a premium nonwoven marketed as soft against a wearer's skin, or a high coefficient of friction nonwoven for improved fit. In some examples, the substrates may be configured as a relatively low basis weight nonwoven intended define a wearer facing surface, which may help to reduce the changes of pressure marks on the wearer's skin from corrugations in the elastic laminates. A relatively low basis weight nonwoven may also have a relatively low bending stiffness, and thus any corrugations against the wearer's skin collapse at relatively lower forces.

As previously mentioned the first and second elastic materials 226, 228 may be configured in various ways and from various materials. For example, the elastic materials may be formed by any suitable method in the art, for example, by extruding molten thermoplastic and/or elastomeric polymers or polymer blends through a slit die and subsequently cooling the extruded sheet. Other non-limiting examples for making film forms include casting, blowing, solution casting, calendaring, and formation from aqueous or, non-aqueous cast dispersions. The elastomer composition of the present disclosure may be made into a film having a basis weight of from about 5 to about 150 g/m². The elastic material can also be an apertured film made of elastomeric material to provide breathability. In some configurations, the first and second elastic materials include a nonwoven web of synthetic fibers. The web can be made of fibers from elastomers or can be mixture of elastomeric fibers with plastic fibers. The first and second elastic materials may also be configured as laminates including elastic material connected with and/or interposed between an outer layer and an inner layer. The elastic material may include one or more elastic elements such as strands, ribbons, or panels. Suitable elastomeric compositions for making elastic materials comprise thermoplastic elastomers selected from the group consisting of Styrenic block copolymers, poly-esters, polyurethanes, polyether amides, polyolefin elastomers, and combinations thereof.

Figure 9:
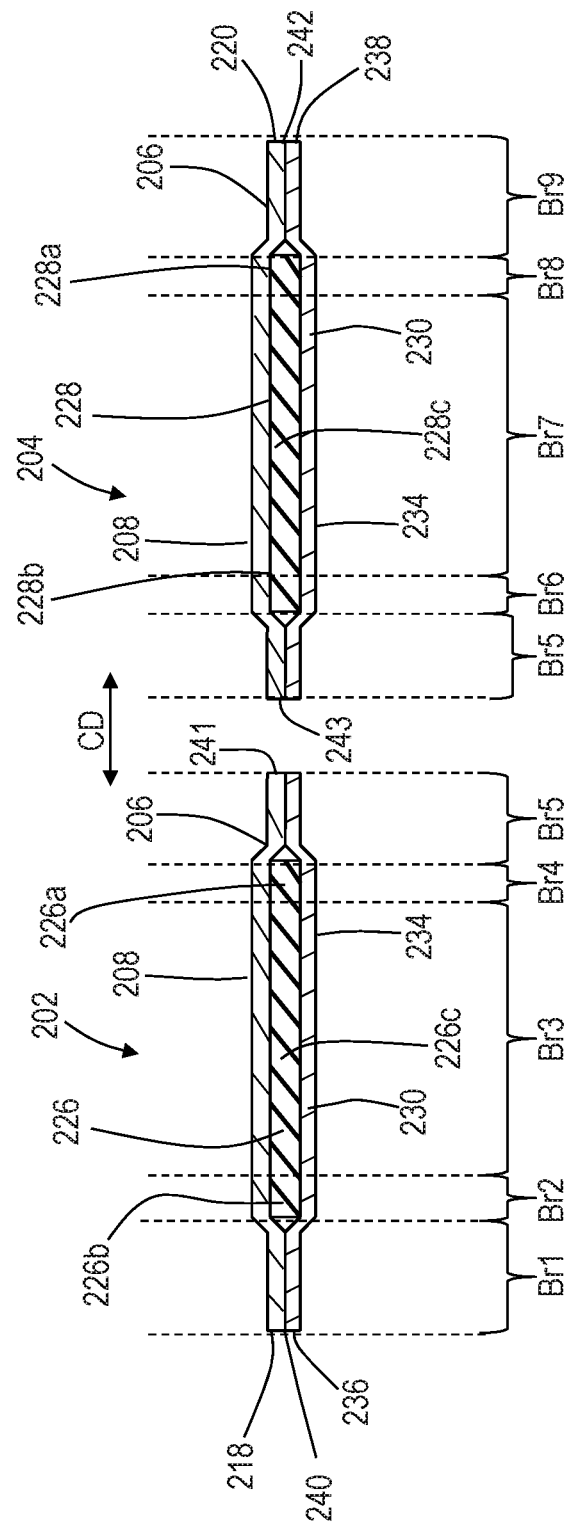
FIG. 9 is a cross sectional view of an alternative configuration of the first elastic laminate and a second elastic laminate.

It is also to be appreciated that the elastic laminates 200 formed herein may not include the first reinforcement layer 212, the second reinforcement layer 214, or the third reinforcement layer 216. For example, the elastic laminate 200 may include only the second and third reinforcement layers 214, 216 and may not include the first reinforcement layer 212. In another example, the elastic laminate 200 may include only the first reinforcement layer 212 and may not include the second and/or third reinforcement layers 214, 216. In yet another example, such as shown in FIGS. 7-9, the elastic laminates 200, 202, 204 may be assembled with no reinforcement layers.

As previously mentioned above with reference to FIGS. 1HA and 1HB, the anvil 102 may include two or more lanes, such as for example lanes L1-L9. And each lane may include pluralities of bonding elements 132 that may be arranged and configured to create pluralities of bonds in two or more corresponding bonding regions in the elastic laminate 200. Thus, elastic laminates herein may be constructed to include two or more bonding regions that do not overlap each other, wherein the bonding regions may be defined by where various layers or components of the elastic laminate are laminated or stacked relative to each other. For example, the elastic laminate 200 shown in FIGS. 4-5 and 7-8 includes bonding regions Br1-Br9 that extend in the machine direction MD and may have various cross directional CD widths. As discussed above, the cutter 140 may cut the elastic laminate 200 along a line extending in the machine direction MD through a central region or location 200c into the first elastic laminate 202 and the second elastic laminate 204. As such, in some configurations, the central region or location 200c of the elastic laminate 200 may be defined bonding region Br5. After the elastic laminate 200 is cut into the first elastic laminate 202 and the second elastic laminate 204 as described above, the first elastic laminate 202 may include bonding regions Br1-B4 and a portion of bonding region Br5, and the second elastic 204 laminate may include bonding regions Br6-B9 and a portion of bonding region Br5. Although some of the bonding regions B1-B9 may border another bonding region, none of the bonding regions Br1-Br9 overlaps another bonding region such that each bonding region is positioned completely outside of all other bonding regions. For the purposes of clarity, dashed lines are shown in FIGS. 4-6 and 7-9 to represent example boundaries between the bonding regions Br1-Br9. It is to be appreciated that such boundaries between the bonding regions Br1-Br9 can also be curved, angled, and/or straight with respect to the cross direction CD.

It is to be appreciated that the bonding regions may be defined in various ways depending on how an elastic laminate is constructed. For example, with reference to FIGS. 4 and 7, a first bonding region Br1 may be defined where the first substrate 206 is in direct contact with the second substrate 230 between the second unstretched edge region 226b of the first elastic material 226 and the longitudinal edge 240. And as shown in FIG. 4, the first bonding region Br1 may also be defined where the second reinforcement layer 214 is in direct contact with both the second surface 210 of the first substrate 206 and the first surface 232 of the second substrate 230. As shown in FIGS. 4 and 7, a second bonding region Br2 may be defined where the second unstretched edge region 226b of the first elastic material 226 is in direct contact with either the first substrate 206 or the second substrate 230. And as shown in FIG. 4, the second bonding region Br2 may also be defined where the second unstretched edge region 226b of the first elastic material 226 is in direct contact with both the second reinforcement layer 214 and the first surface 232 of the second substrate 230. As shown in FIGS. 4 and 7, a third bonding region Br3 may be defined where the stretched central region 226c of the first elastic material 226 is in direct contact with either or both the second surface 210 of the first substrate 206 and the first surface 232 of the second substrate 230. As shown in FIGS. 4 and 7, a fourth bonding region Br4 may be defined where the first unstretched edge region 226a of the first elastic material 226 is in direct contact with either the first substrate 206 or the second substrate 230. And as shown in FIG. 4, the fourth bonding region Br4 may also be defined where the first unstretched edge region 226a of the first elastic material 226 is in direct contact with both the first reinforcement layer 212 and the first surface 232 of the second substrate 230. As shown in FIG. 4, a fifth bonding region Br5 may be defined where the first reinforcement layer 212 is in direct contact with both the second surface 210 of the first substrate 206 and the first surface 232 of the second substrate 230. And as shown in FIG. 7, the fifth bonding region Br5 may also be defined where the first substrate 206 is in direct contact with the second substrate 230 between the first unstretched edge region 226a of the first elastic material 226 and the second unstretched edge 228b of the second elastic material 228. As shown in FIGS. 4 and 7, a sixth bonding region Br6 may be defined where the second unstretched edge region 228b of the second elastic material 228 is in direct contact with either the first substrate 206 or the second substrate 230. As shown in FIG. 4, the sixth bonding region Br6 may also be defined where the second unstretched edge region 228b of the second elastic material 228 is in direct contact with both the first reinforcement layer 212 and the first surface 232 of the second substrate 230. As shown in FIGS. 4 and 7, a seventh bonding region Br7 may be defined where the stretched central region 228c of the second elastic material 228 is in direct contact with either or both the second surface 210 of the first substrate 206 and the first surface 232 of the second substrate 230. As shown in FIGS. 4 and 7, an eighth bonding region Br8 may be defined where the first unstretched edge region 228a of the second elastic material 228 is in direct contact with either the first substrate 206 or the second substrate 230. And as shown in FIG. 4, the eighth bonding region Br8 may also be defined where the first unstretched edge region 228a of the second elastic material 228 is in direct contact with both the third reinforcement layer 216 and the first surface 232 of the second substrate 230. As shown in FIGS. 4 and 7, a ninth bonding region Br9 may be defined where the first substrate 206 is in direct contact with the second substrate 230 between the first unstretched edge region 228a of the second elastic material 228 and the longitudinal edge 242. And as shown in FIG. 4, the ninth bonding region Br9 may be defined where the third reinforcement layer 216 is in direct contact with both the second surface 210 of the first substrate 206 and the first surface 232 of the second substrate 230.

It is to be appreciated that the elastic laminates herein may be configured with various number of bonding regions, each including pluralities of bonds 300 that may also be formed in various ways. For example, the bonds 300 may include pressure bonds, heat bonds, ultrasonic bonds, and/or adhesive bonds. It is also to be appreciated that the elastic laminates herein may be configured with various number of bonding regions, each including pluralities of bonds 300 configured in various ways. For example, as shown in FIGS. 5 and 8, the bonds 300 within each of the bonding regions Br1-Br9 may be configured with the same or different shapes, sizes, orientations, areas and/or distances between bonds 300. It is also to be appreciated that the bonding regions Br1-Br9 may include the same or different quantities of bonds 300 and that any of the bonding regions may include bonds 300 with shapes, sizes, orientations, areas, and/or distances between bonds that are the same or different from shapes, sizes, orientations, areas, and/or distances between bonds 300 included in other bonding regions.

It is to be appreciated that some or all the bonding regions of an elastic laminate may have the same or different bond densities. As such, some or all the bonding regions of an elastic laminate may have the same or different bond frequencies. In addition, some or all the bonding regions of an elastic laminate may have the same or different aggregate bond coverage. Further, the bond frequency and aggregate bond coverage in a first bonding region may be the same as the bond frequency and aggregate bond coverage in a second bonding region while at least one bond in the first bonding region may define a shape that is different from a shaped defined by at least one bond in the second bonding region.

For example with reference to FIGS. 4-6 and 7-9, in some configurations, the bond density of the third bonding region Br3 may be less than the bond density of the second bonding region Br2 and/or the fourth bonding region B4. In turn, the bond frequency and/or the aggregate bond coverage of the third bonding region Br3 may be less than the bond frequency and/or the aggregate bond coverage of the second bonding region Br2 and/or the fourth bonding region B4. In some configurations, the bond density of the third bonding region Br3 may be less than the bond density of the first bonding region Br1 and/or the fifth bonding region B5. In turn, the bond frequency and/or the aggregate bond coverage of the third bonding region Br3 may be less than the bond frequency and/or the aggregate bond coverage of the first bonding region Br1 and/or the fifth bonding region B5. In some configurations, the bond density of the third bonding region Br3 may be less than the bond densities of bonding regions Br2 and/or Br4, and the bond densities of bonding regions Br2 and Br4 may be greater or less than the bond densities of bonding regions B1 and/or Br5. In turn, the bond frequency and/or aggregate bond coverage of the third bonding region Br3 may be less than the bond frequency and/or aggregate bond coverage of bonding regions Br2 and/or Br4, and the bond frequency and/or aggregate bond coverage of bonding regions Br2 and Br4 may be greater than or less than the bond frequency and/or aggregate bond coverage of bonding regions B1 and/or Br5.

In additional examples with reference to FIGS. 4-6 and 7-9, in some configurations, the bond density of the seventh bonding region Br7 may be less than the bond density of the sixth bonding region Br6 and/or the eighth bonding region B8. In turn, the bond frequency and/or the aggregate bond coverage of the seventh bonding region Br7 may be less than the bond frequency and/or the aggregate bond coverage of the sixth bonding region Br6 and/or the eighth bonding region B8. In some configurations, the bond density of the seventh bonding region Br7 may be less than the bond density of the ninth bonding region Br9 and/or the fifth bonding region B5. In turn, the bond frequency and/or the aggregate bond coverage of the seventh bonding region Br7 may be less than the bond frequency and/or the aggregate bond coverage of the ninth bonding region Br9 and/or the ninth bonding region B9. In some configurations, the bond density of the seventh bonding region Br7 may be less than the bond densities of bonding regions Br6 and/or Br8, and the bond densities of bonding regions Br6 and Br8 may be greater or less than the bond densities of bonding regions B9 and/or Br5. In turn, the bond frequency and/or aggregate bond coverage of the seventh bonding region Br7 may be less than the bond frequency and/or aggregate bond coverage of bonding regions Br6 and/or Br8, and the bond frequency and/or aggregate bond coverage of bonding regions Br6 and Br8 may be greater than or less than the bond frequency and/or aggregate bond coverage of bonding regions B5 and/or Br9. It is also appreciated that the bond densities, bond frequencies, and/or aggregate bond coverage of any of the bonding regions B1-Br5 may be greater than, equal to, or less than the bond densities, bond frequencies, and/or aggregate bond coverage of any of the bonding regions B6-Br9. In some configurations, the bond density, bond frequency, and/or aggregate bond coverage of any one of the bonding regions Br1-Br6 may be equal to the bond density, bond frequency, and/or aggregate bond coverage of any other one of the bonding regions Br1-Br6 while a shape of at least one bond in any one of the bonding regions Br1-Br6 may be different from a shape of at least one bond in any other one of the bonding regions Br1-Br6.

Figure 10A:
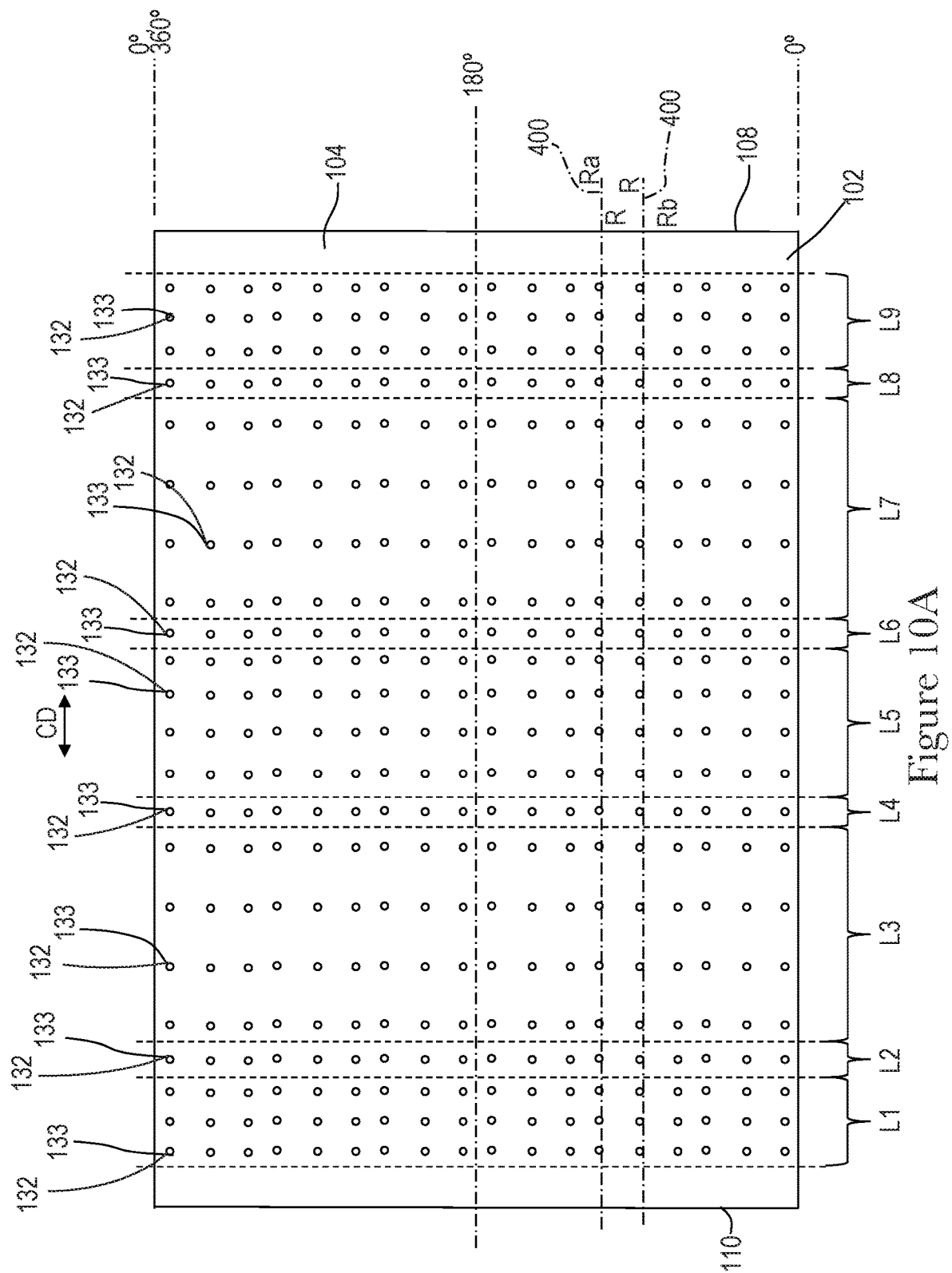
FIG. 10A is a view of an outer circumferential surface of an anvil laid out flat and showing pluralities of bonding surfaces.

It is to be appreciated that the apparatuses and methods herein may be configured to create various configurations of bonds 300 in an elastic laminate. For example, as previously mentioned, the anvil 102 may be configured with lanes of bonding elements 132, such that the bonding elements that may extend for various lengths along the outer circumferential surface 104 that may be less than or completely around the axis of rotation 106. For example, FIG. 10A shows a view of an outer circumferential surface 104 of an anvil 102 laid out flat showing bonding elements 132 at various cross directional CD positions and various angular positions from 0° to 360° with respect to the axis of rotation 106. As shown in FIG. 10A, pluralities of bonding elements 132 with bonding surfaces 133 may be arranged in lanes L1-L9 extending along the outer circumferential surface 104. The bonding elements 132 and bonding surfaces 133 may also be arranged in rows R extending in the cross direction CD, wherein the rows R may be angularly separated from each other by various distances along the outer circumferential surface 104. It is to be appreciated that the anvil 102 may include more or less than the quantity of rows R shown in FIG. 10A. For the purposes of clarity, dashed lines 400 are shown in FIG. 10A to represent example orientations and shapes of a first row Ra and a second row Rb of bonding elements 132 and bonding surfaces 133. It is to be appreciated that such orientations and shapes of the rows R of bonding elements 132 and bonding surfaces 133 can also be curved, angled, and/or straight with respect to each other and/or the cross direction CD.

It is to be appreciated that the anvil 102 may be configured with rows R having the same or different quantities of bonding surfaces 133 having the same or different shapes, sizes, orientations, areas and/or distances between bonding surfaces. It is also to be appreciated that the rows R may include the same or different quantities of bonding elements 132 and that any of the rows R may include bonding surfaces 133 with shapes, sizes, orientations, areas, and/or distances between bonding surfaces that is the same or different from shapes, sizes, orientations, areas, and/or distances between bonding surfaces of bonding surfaces 133 included in other rows R. As such, a plurality of bonding surfaces in any one row R may be arranged to apply bonds 300 in corresponding rows R to an elastic laminate 200 at a bond density that may be less than, equal to, or greater than a bond density defined by bonds created by a plurality of bonding surfaces in another row R. Thus, the rows R of bonding elements 132 on the anvil 102 may create corresponding rows R of bonds 300 in an advancing elastic laminate 200, such as shown FIG. 10B. As such, the rows R of bonds 300 may be repeated along the machine direction MD of the elastic laminate 200. For the purposes of clarity, dashed lines 401 are shown in FIG. 10B to represent example orientations and shapes of a first row R1 and a second row R1 of bonds 300. It is to be appreciated that such orientations and shapes of the rows R of bonds 300 can also be curved, angled, and/or straight with respect to each other and/or the cross direction CD. In turn, the rows R of bonds 300 may be repeated along the machine direction MD of the elastic laminate 200.

Figure 11A:
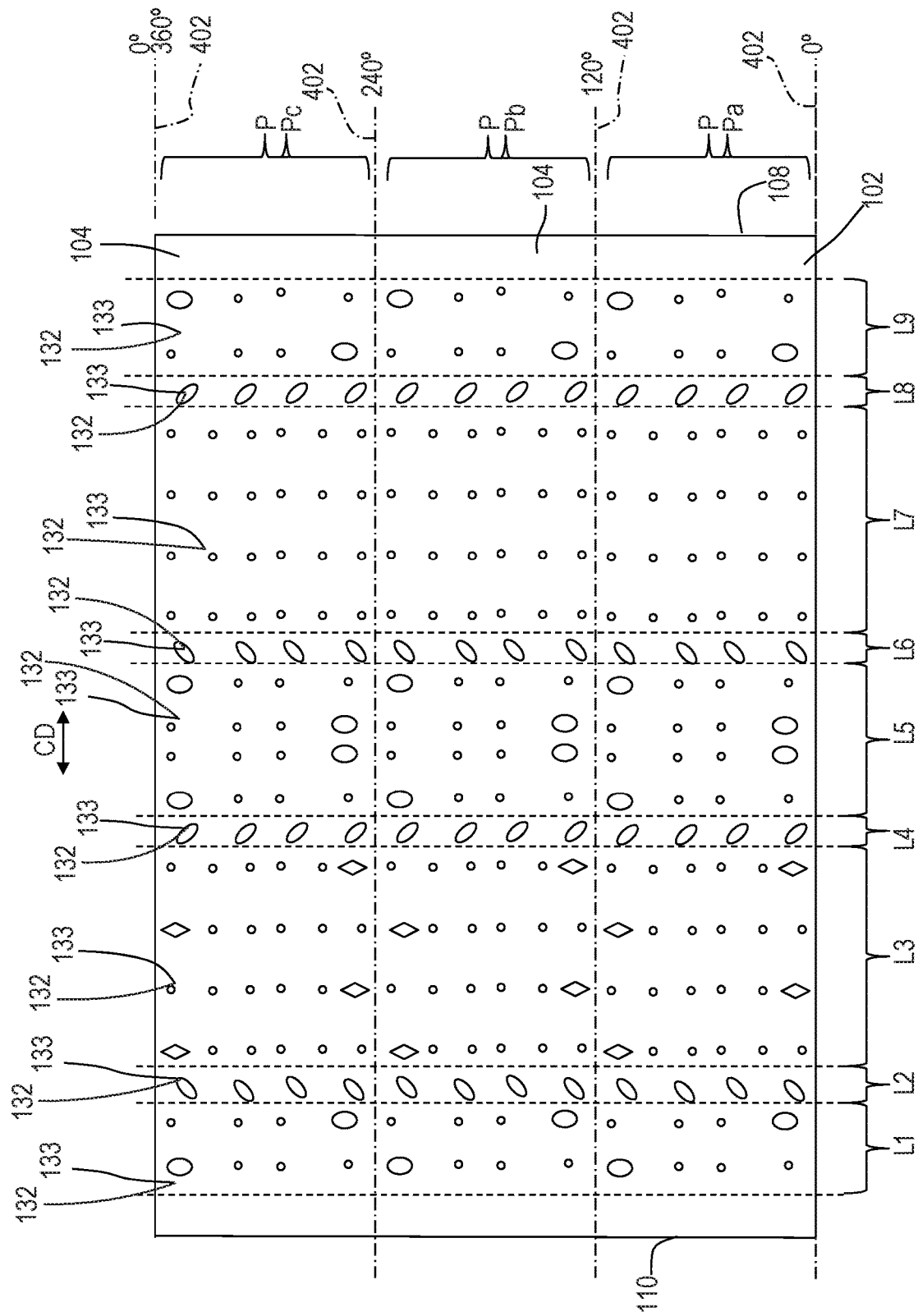
FIG. 11A is a view of an outer circumferential surface of an anvil laid out flat and showing pluralities of bonding surfaces arranged to define repeating patterns.

It is also to be appreciated that the bonding elements 132 and bonding surfaces 133 may be arranged to define repeating patterns along the outer circumferential surface 104 of the anvil 102. For example, FIG. 11A shows a view of an outer circumferential surface 104 of an anvil 102 laid out flat showing bonding elements 132 arranged to define patterns P at various angular positions from 0° to 360° with respect to the axis of rotation 106. The pluralities of bonding elements 132 with bonding surfaces 133 are illustrated as being arranged to define three patterns Pa, Pb, Pc that may extend angularly for various distances along the outer circumferential surface 104. The bonding elements 132 and bonding surfaces 133 may also be arranged in lanes L1-L9 extending along the outer circumferential surface 104. It is to be appreciated that the anvil 102 may include more or less than the quantity of patterns P shown in FIG. 11A. For the purposes of clarity, dashed lines 402 are shown in FIG. 11A to represent example boundaries and shapes of patterns P of bonding elements 132 and bonding surfaces 133. It is to be appreciated that such boundaries and shapes of the patterns P of bonding elements 132 and bonding surfaces 133 can also be curved, angled, and/or straight with respect to each other and/or the cross direction CD.

Figure 11B:
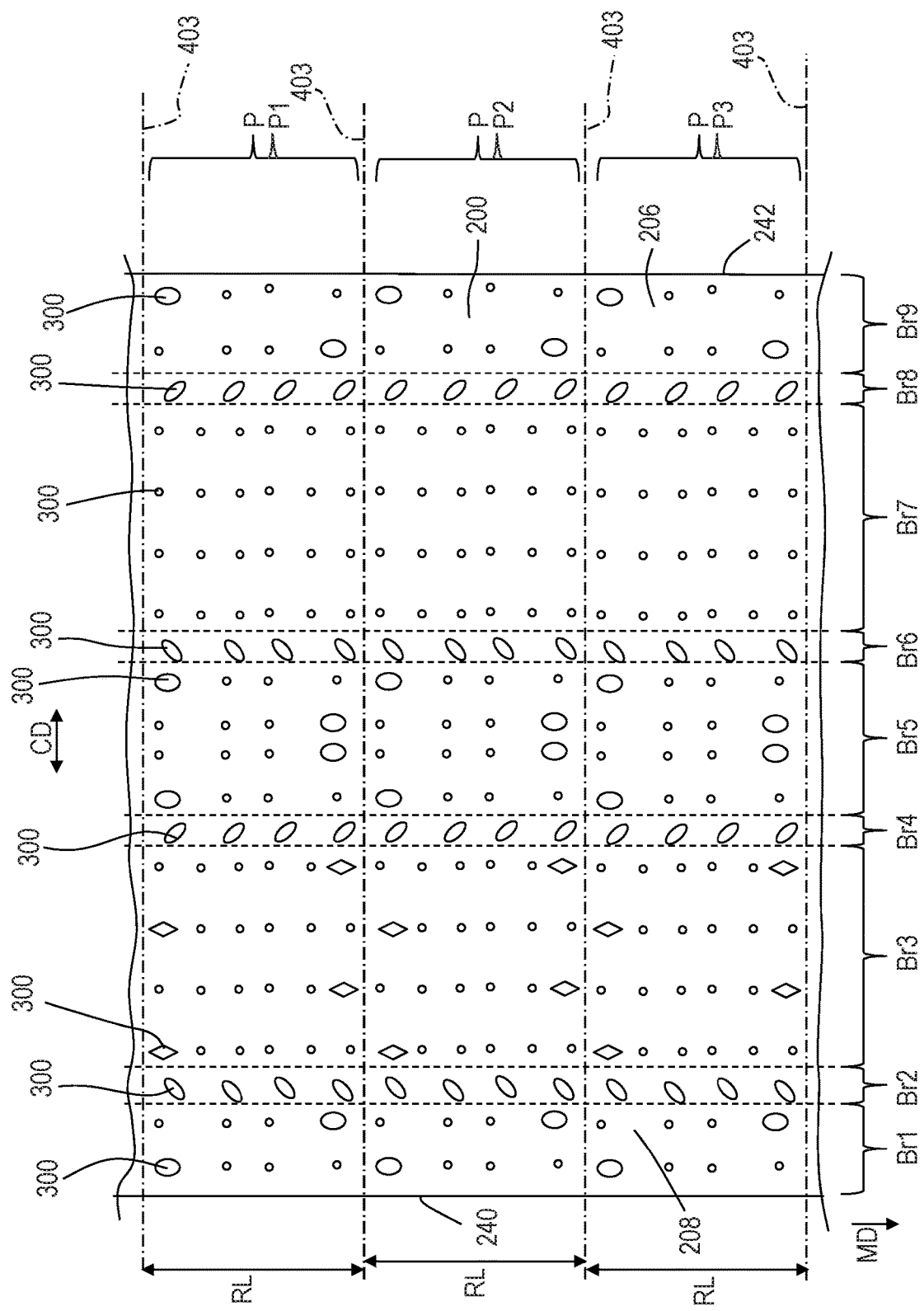
FIG. 11B is a top plan view of an elastic laminate with repeating patterns of bonds corresponding with the bonding surfaces shown in FIG. 11A.

It is to be appreciated that the anvil 102 may be configured with patterns P having the same or different quantities of bonding surfaces 133 having the same or different shapes, sizes, orientations, areas and/or distances between bonding surfaces. It is also to be appreciated that the patterns P may include the same or different quantities of bonding elements 132 and that any of the patterns P may include bonding surfaces 133 with shapes, sizes, orientations, areas, and/or distances between bonding surfaces that is the same or different from shapes, sizes, orientations, areas, and/or distances between bonding surfaces of bonding surfaces 133 included in other patterns P. As such, a plurality of bonding surfaces in any one pattern P may be arranged to apply bonds 300 to an elastic laminate 200 in corresponding patterns P at a bond density that may be less than, equal to, or greater than a bond density defined by bonds 300 created by a plurality of bonding surfaces 133 in another pattern P. Thus, the patterns P of bonding elements 132 on the anvil 102 may create corresponding patterns P of bonds 300 in an advancing elastic laminate 200, such as shown FIG. 11B. As such, the patterns P of bonds 300 may be repeated along the machine direction MD of the elastic laminate 200. For the purposes of clarity, dashed lines 403 are shown in FIG. 11B to represent example boundaries and shapes of a first pattern P1, a second pattern P2, and a third pattern P3 of bonds 300. It is to be appreciated that such boundaries and shapes of the patterns P of bonds 300 can also be curved, angled, and/or straight with respect to each other and/or the cross direction CD.

Figure 11C:
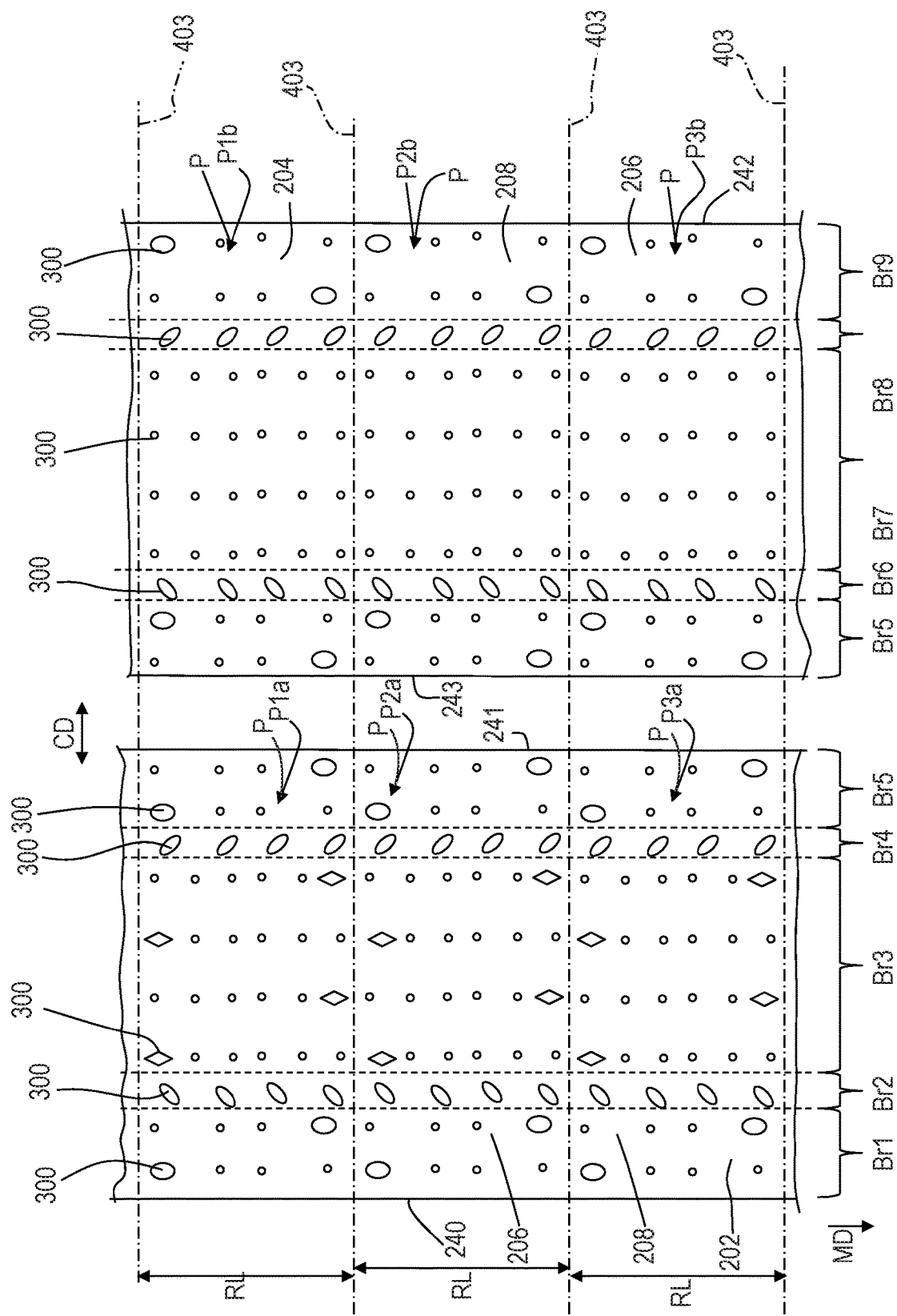
FIG. 11C is a top plan view of a first elastic laminate and a second elastic laminate formed from the elastic laminate in FIG. 11B.
Figure 11D:
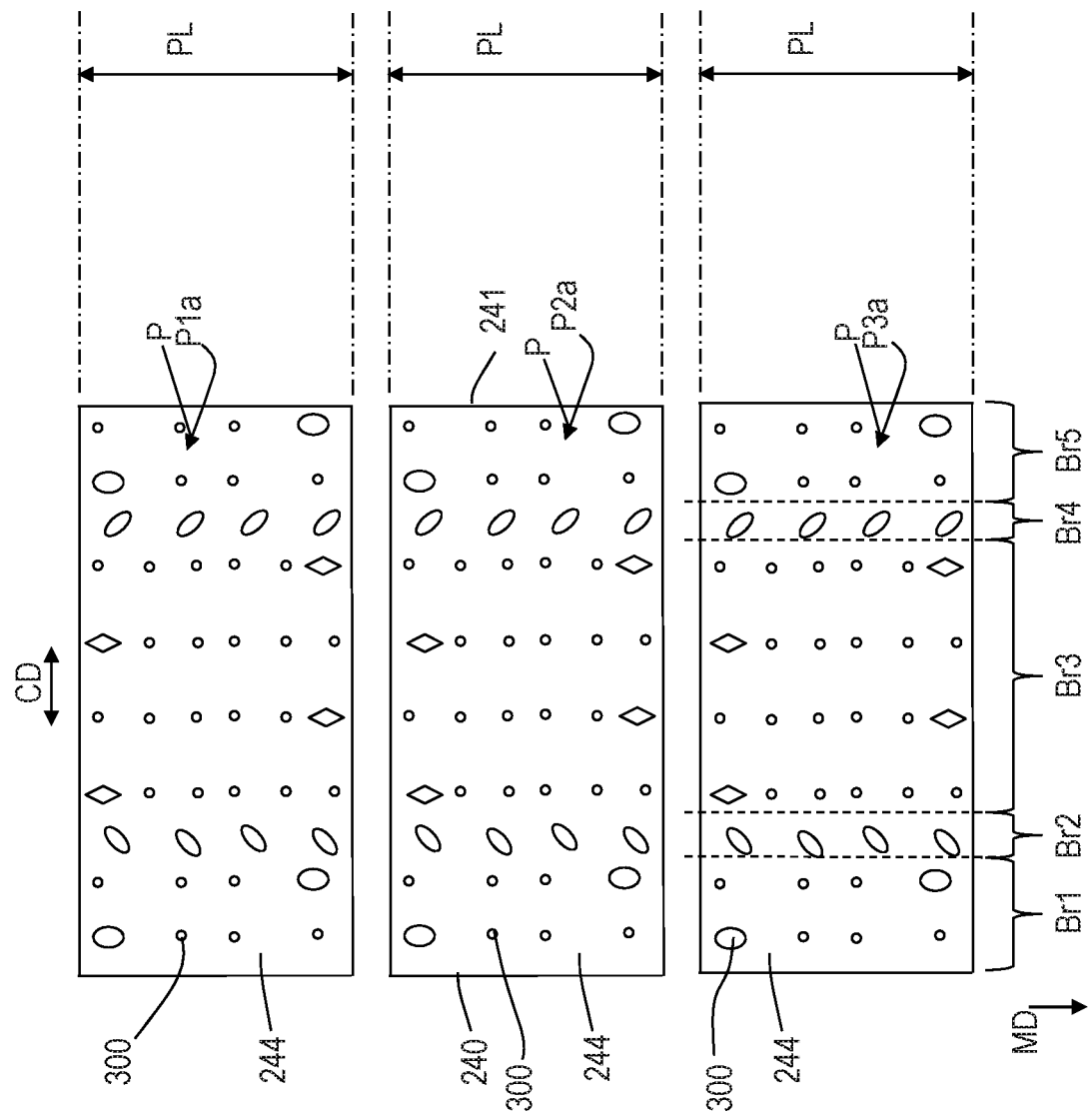
FIG. 11D is a top plan view of discrete pieces cut from the first elastic laminate in FIG. 11C.

The patterns P of bonds 300 may be repeated along the machine direction MD of the elastic laminate 200. In turn, the patterns P may be pitched such that individual components or pieces cut from the elastic laminate 200 may include one or more patterns P. For example, as shown in FIG. 11B, the patterns P1, P2, P3 are illustrated as having the same shapes and sizes. Thus, the patterns P are shown as repeating at repeat lengths RL along the machine direction MD. As previously mentioned, an assembled elastic laminate 200 may be subsequently slit along the machine direction MD into a first elastic laminate 202 and a second elastic laminate 204, such as shown in FIG. 11C. As such, the patterns P of the elastic laminate 200 may also be divided, wherein the first elastic laminate 202 and the second elastic laminate 204 may include an entirety of or a portion of each pattern P. For example, the first elastic laminate 202 is illustrated as including patterns P1a, P2a, P3a and the second elastic laminate 204 is illustrated as including patterns P1b, P2b, P3b, each representing portions of patterns P1, P2, P3, respectively from FIG. 11B. In addition, the first elastic laminate 202 and/or the second elastic laminate 204 may also be cut along the cross direction CD and separated into discrete parts or pieces 244, such as shown in FIGS. 2A and 11D. Each discrete piece 244 may be cut to have a pitch length PL and may each include a pattern P of bonds 300. It is also to be appreciated that the apparatuses and methods herein may also be configured with a registration system. Thus, it is to be appreciated that the speed of the elastic laminates 200, 202, 204 and/or the cutter 144 shown in FIG. 2A may be controlled to cut the elastic laminates into pieces having pitch lengths PL that are registered with the patterns P of bonds 300 in accordance with respective repeat lengths RL.

Figure 12B:
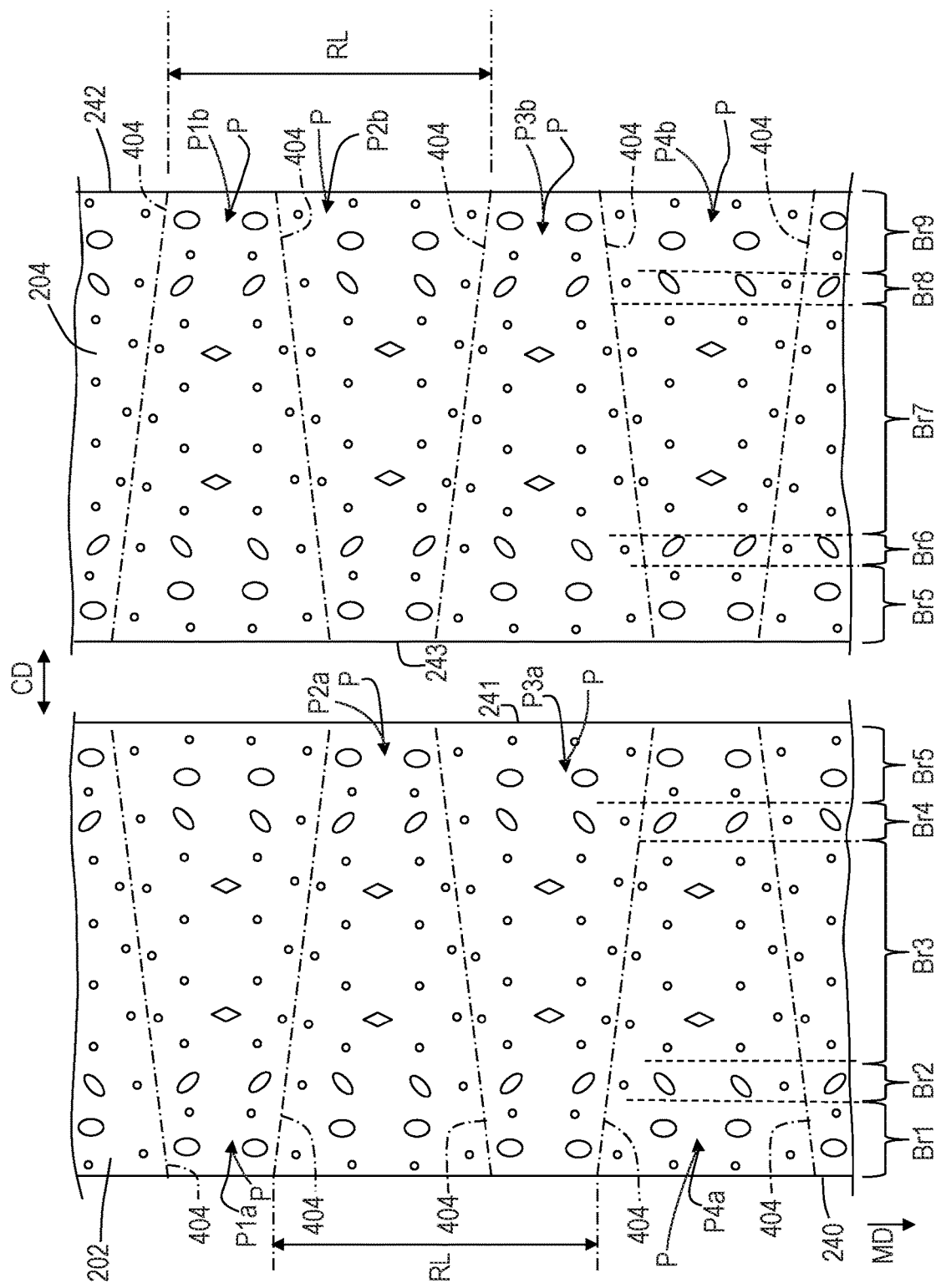
FIG. 12B is a top plan view of a first elastic laminate and a second elastic laminate formed from the elastic laminate in FIG. 12A.
Figure 12C:
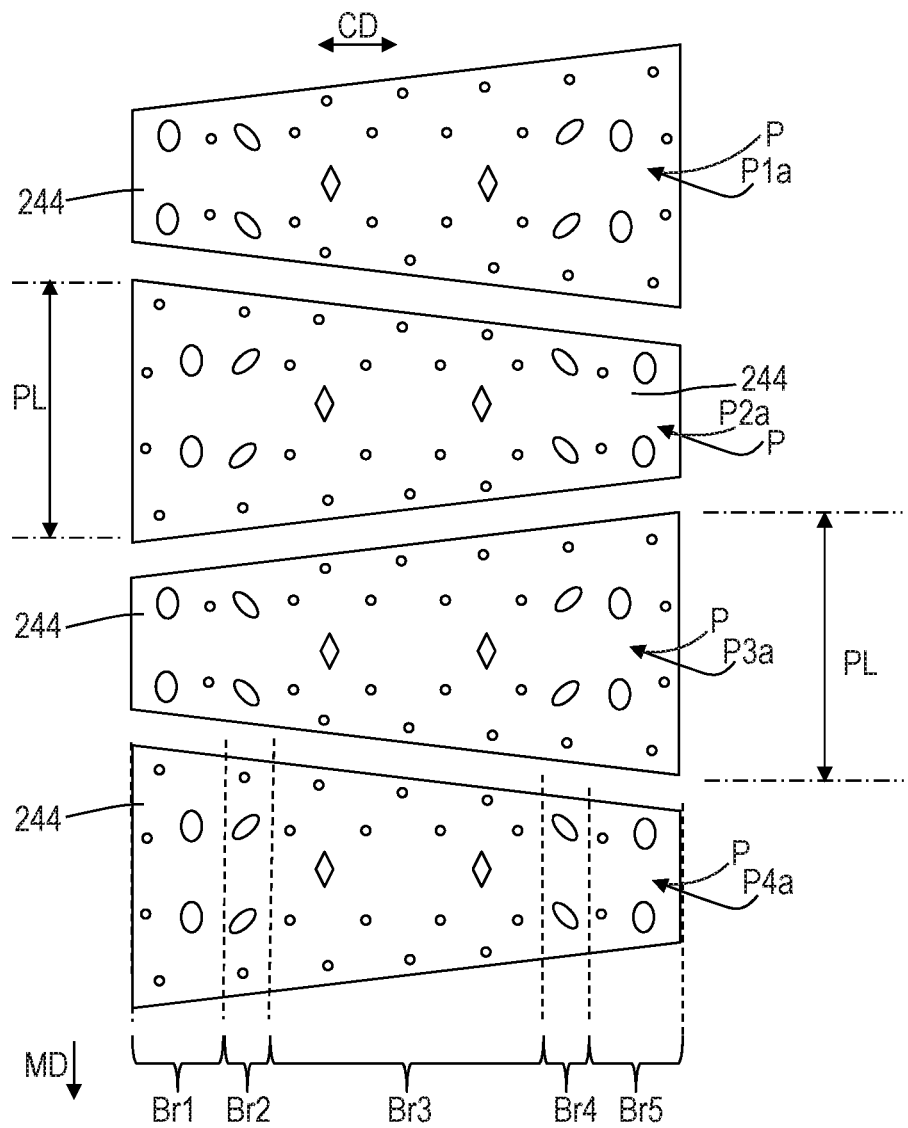
FIG. 12C is a top plan view of discrete pieces cut from the first elastic laminate in FIG. 12B.

As previously mentioned, the apparatuses 100 herein may be configured to apply bonds 300 in patterns P having various shapes and sizes. For example, FIG. 12A shows examples of patterns P of bonds of varying shapes. For the purposes of clarity, dashed lines 404 are shown in FIG. 12A to represent example boundaries and shapes of a first pattern P1, a second pattern P2, a third pattern P3, and a fourth pattern P4 of bonds 300. As previously discussed, the patterns P of bonds 300 may be repeated along the machine direction MD of the elastic laminate 200. And the patterns P may be pitched such that individual components or pieces cut from the elastic laminate 200 may include one or more patterns P. For example, as shown in FIG. 12A, the patterns P1, P3 are illustrated as having the same shapes and sizes, and the patterns P2, P4 are illustrated as having the same shapes and sizes. In addition, the patterns P1, P3 shapes that are different from the shapes of patterns P2, P4. The patterns P are shown as repeating at repeat lengths RL along the machine direction MD. As previously mentioned, an assembled elastic laminate 200 may be slit along the machine direction MD into a first elastic laminate 202 and a second elastic laminate 204, such as shown in FIG. 12B. As such, the patterns P of the elastic laminate 200 may also be divided, wherein the first elastic laminate 202 and the second elastic laminate 204 may include an entirety of or a portion of each pattern P. For example, the first elastic laminate 202 is illustrated as including patterns P1a, P2a, P3a, P4a and the second elastic laminate 204 is illustrated as including patterns P1b, P2b, P3b, P4b, each representing portions of patterns P1, P2, P3, P4, respectively from FIG. 12A. In addition, the first elastic laminate 202 and/or the second elastic laminate 204 may also be cut along the cross direction CD and separated into discrete parts or pieces 244, such as shown in FIGS. 2A and 12C. Each discrete piece 244 may be cut to have a pitch length PL and may each include a pattern P of bonds 300.

It is to be appreciated that the apparatus 100 herein may be configured to include various types of accessories to help reduce capital costs and/or ensure consistent quality of manufactured products. For example, it is to be appreciated that components discussed herein that may be used to assemble elastic laminates, such as elastic films and nonwoven substrates may have a high neckdown modulus, resulting in different strip widths for small changes in tension. During assembly, transient neckdown may result in loss of film spreading in the laminate or require additional substrate width at additional product cost. As such, the apparatus 100 herein may utilize various accessories to help reduce such variations in width. For example, the apparatus may include a linear or rotary dancer system, such as disclosed in European Patent Publication No. EP 2 841 364 A1. Such a dancer system may be operatively connected with a servo motor and drive controller operating in torque mode, and may result in substantially improved tension control of elastic films and nonwoven substrates, which in turn, may help reduce width variation. Various types of servo motor and drive controllers may be used, such as for example, a Kinetix 5700 system and MPL-B540K-SJ72AA motor from Rockwell Automation. The metering flow rate of an elastic film or nonwoven substrate may be controlled by a servo driven roller downstream of the servo tensioner.

In some configurations, the apparatus 100 herein may include an additional flywheel, such as a large diameter pulley, that may be added to a motor used for a nonwoven substrate or elastic film spindle drive. Such a flywheel may help increase the motor side inertia and may reduce the ratio of motor inertia to load inertia of a spindle drive. A lower inertia ratio between the driving and driven sides of the belt drive may improve tuning of the position loop in the commercial servo drive. In turn, capital costs may then be reduced by enabling the use of relatively smaller motors.

In some configurations, the bonding elements 132 on the anvil 102 may be arranged in a counterbalance pattern. Such a counterbalance pattern may reduce the variation in amount of bonding pattern which may be operatively engaged against the ultrasound sonotrode as the anvil 102 rotates. In some configurations, continuous bond patterns may be nominally balanced. In contrast, the variation in bond area exposed to the sonotrode as the anvil 102 rotates may be substantial when arranging the bonding surfaces to define regional bond patterns. In some configurations, the counterbalance pattern may be positioned in a non-functional region of the elastic laminate, for example, such as using such a bond pattern in a trim region to reduce the variation in the bond pattern area as the anvil rotates.

In some configurations, the elastic films and/or nonwoven substrates may be tracked in the cross direction CD relative to the regional bond patterns. For example, the elastic film may be tracked to a slitter, wherein the tracking may be provided by a commercial offset pivot guide, such as available commercially from Erhardt+Leimer or Maxcess Corporation. The pivot guide may be in a center-guiding mode. By slitting one film into two, the width error of the incoming roll for each of the slit films may be half or less that of the original film width error. By center guiding again onto a spreading device, which may be a canted vacuum wheel with a single row of nubs, the original substrate width variation at each edge position may be reduced to one quarter or less of the original width variation. The center-guiding may be by a single sensor, such as an E+L FR6001 sensor. The sensor may be of a light curtain type, such as available from Wenglor Sensor LLC. The setpoint position may be configurable for different products, via communication over Ethernet/IP. Such techniques may allow a minimal film width in the CD, which may reduce product costs. Accurate tracking, such as within 2 mm, 1 mm, 0.5 mm, or less may allow an unstretched film width at edges of the film substrate to be made relatively small, such as 3 mm or less. Accurate tracking may be required to align the film edges with a vacuum pattern in the anvil 102. Each of the films or substrates may be tracked individually, and each of the films or substrates may be tracked near to the lamination in the process flow. For films, the tracking may be immediately before a set of canted spreader disks. And substrate may be delivered as a wide material, and slit into two or more substrates. Narrow substrates may be repositioned in the cross direction by feedback controlled offset pivot guides, a set of parallel canted idlers, web twists, turn bars, and/or grooved idlers. Sensors may measure and output an error measurement for cross direction CD tracking location or width of film, corrugation zone, nonwoven substrate, or zonal pattern to an operator display device. Operators may have the ability to fine tune manual setup adjustments. The web guides or optical sensors near the lamination unit may detect edge positions, widths, or center positions of the substrates. The output of such commercial devices may trigger a reject of one or more pads from a converting line.

Zoned patterns on the anvil may also be phased in the machine direction MD and tracked in the cross direction CD relative to an electronic timing position, a final knife, a back ear die cutter, a back ear application unit, a tape application unit, a tape bonding unit, an insignia on one of the substrates or another product feature. In addition, a downstream machine vision system may be used to inspect the elastic laminate quality. Such quality inspections may include width of the corrugation, edges and/or appearance of the bond patterns and/or insignia, machine direction MD placement of the regional bond patterns, cross direction CD placement of the zonal pattern. Such inspections may include edge positions of the substrates 206, 230, first film 226, second film 228, unstretched film regions 226a, 226b, 228a, 228b, as well as the corrugation region, a folded edge, or a reinforcement layer 212, 214, 216. Such inspections may include detection of flipped or folded edges in the films. The downstream system may inspect for delamination. The downstream system may detect film tears and/or enlarged bond sites in the zonal patterns. Backlit lighting may be used to highlight the ultrasound bond sites. The vision system may also be used to identify and reject splices in a substrate. The apparatuses herein may also include tracking sensors and/or a vision system operatively connected with an operator display or to a quality monitoring system to monitor the width of a substrate, including film substrate throughout a roll of material, including as a function of roll diameter, and between rolls, including recording the lot of material, the roll identification number, the supplier line, the supplier plant and/or the supplier lane from a material tracking system.

In some configurations, an output of the ultrasonic system may be used to identify out of specification product. Such output may be a sensor value, a calculated value in the ultrasound generator, or a fault signal in the ultrasound generator. Ultrasound frequency, power consumption, metal to metal contract, and/or compression force may be monitored. The ultrasound generator may be a commercial unit, such as a Herrmann Ultrasonic VE20 Micrond CSI with an Ultrabond digital generator and microGap controller. The fault condition may be calculated in programmable logic controller or computer connected via network such as CAN-bus or Ethernet/IP to the ultrasonic commercial parts. The limits may be adjusted based on the phase position of the ultrasound controller. The compression force may be varied with line speed, substrate basis weight, substrate width, or substrate type. A home position sensor may be used to identify the position of the zonal bond patterns.

It is to be appreciated that aspects of the apparatus 100 herein may be configured in various ways and may operate to assemble elastic laminates 200, 202 from various types of material and/or components. For example, it is to be appreciated that the in some configurations, the elastic laminate assembly operations may be performed separate to a final assembly process, such as for example, assembling the elastic laminates offline wherein the elastic laminates may be stored until needed for production. For example, elastic laminate assembly operations may be accomplished on discrete assembly lines, separately from converting lines that may be dedicated to manufacturing disposable absorbent articles. After assemblage on the discrete lines, the elastic laminates may be delivered to the absorbent article converting lines, such as in a form of rolls of continuous elastic laminates. It is to be appreciated that such rolls of continuous elastic laminates may be planetary wound or traversely wound. It is also to be appreciated that the elastic laminate assembly process may be done online during the article assembly process.

Figure 13B:
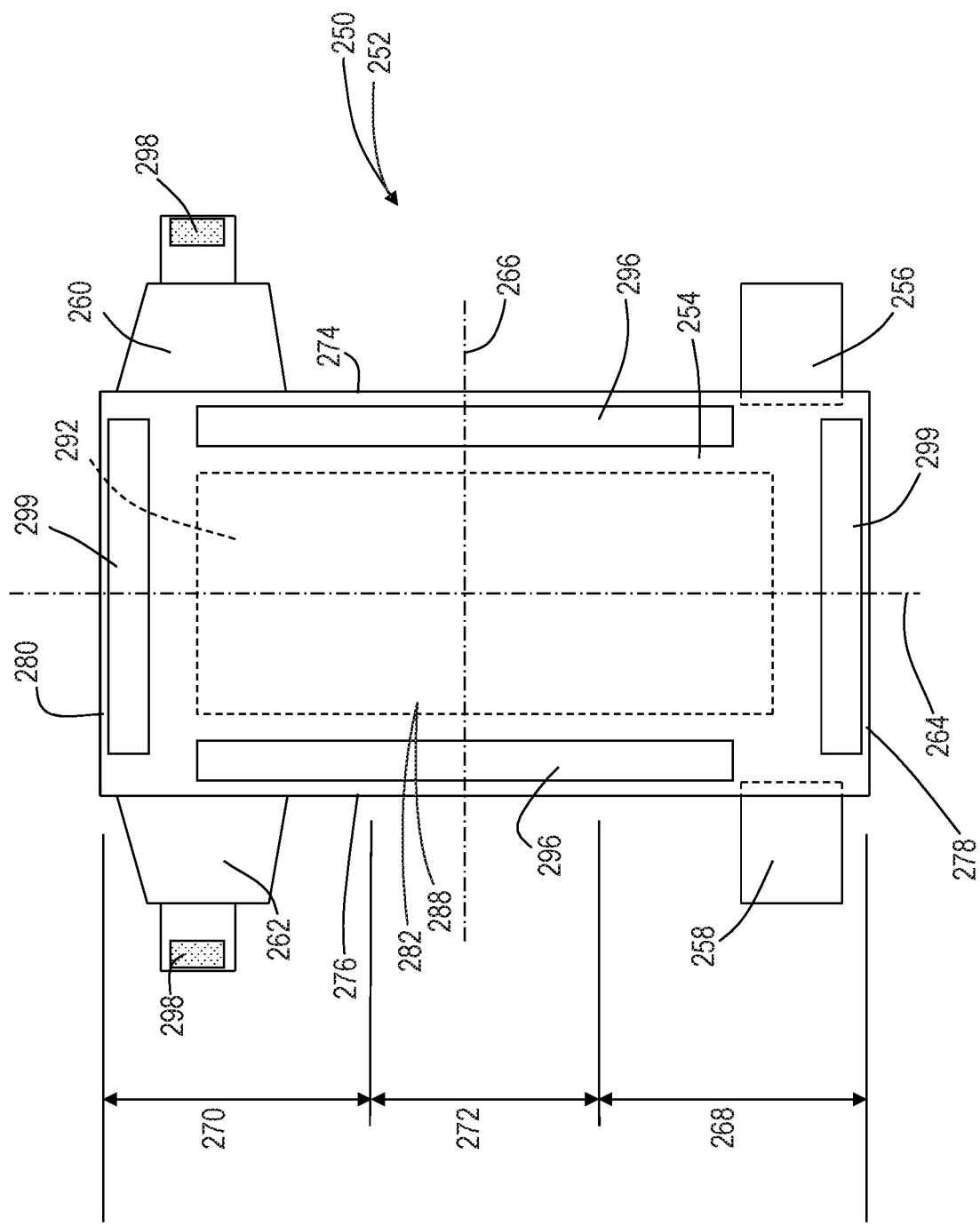
FIG. 13B is a plan view of the absorbent article of FIG. 13A that may include one or more elastic laminates manipulated during manufacture according to the apparatuses and methods disclosed herein with the portion of the diaper that faces toward a wearer oriented towards the viewer.

As mentioned above, apparatuses and methods of the present disclosure may be utilized to assemble various forms of elastic laminates used in the manufacture of absorbent articles. Such elastic laminates may be utilized in absorbent article components such as, for example: backsheets, topsheets, absorbent cores, front and/or back ears, fastener components, and various types of elastic webs and components such as leg elastics, barrier leg cuff elastics, and waist elastics. For the purposes of a specific illustration, FIGS. 13A and 13B show an example of a disposable absorbent article 250 in the form of a diaper 252 that may be constructed from such elastic laminates manipulated during manufacture according to the apparatuses and methods disclosed herein. In particular, FIG. 13A is a partially cut away plan view of an absorbent article in the form of a taped diaper that may include one or more elastic laminates assembled during manufacture according to the apparatuses and methods disclosed herein with the portion of the diaper that faces away from a wearer oriented towards the viewer. FIG. 13B is a plan view of the absorbent article of FIG. 13A that may include one or more elastic laminates assembled during manufacture according to the apparatuses and methods disclosed herein with the portion of the diaper that faces toward a wearer oriented towards the viewer.

As shown in FIGS. 13A-13B, the diaper 252 includes a chassis 254 having a first ear 256, a second ear 258, a third ear 260, and a fourth ear 262. To provide a frame of reference for the present discussion, the chassis is shown with a longitudinal axis 264 and a lateral axis 266. The chassis 254 is shown as having a first waist region 268, a second waist region 270, and a crotch region 272 disposed intermediate the first and second waist regions. The periphery of the diaper is defined by a pair of longitudinally extending side edges 274, 276; a first outer edge 278 extending laterally adjacent the first waist region 268; and a second outer edge 280 extending laterally adjacent the second waist region 270. As shown in FIGS. 13A-13B, the chassis 254 includes an inner, body-facing surface 282, and an outer, garment-facing surface 284. A portion of the chassis structure is cut-away in FIG. 13A to more clearly show the construction of and various features that may be included in the diaper. As shown in FIGS. 13A-13B, the chassis 254 of the diaper 252 may include a topsheet 288 defining the inner, body-facing surface 282, and a backsheet 290 defining the outer, garment-facing surface 284. An absorbent core 292 may be disposed between a portion of the topsheet 288 and the backsheet 290. As discussed in more detail below, any one or more of the regions may be stretchable and may include an elastomeric material or laminate as described herein. As such, the diaper 252 may be configured to adapt to a specific wearer's anatomy upon application and to maintain coordination with the wearer's anatomy during wear.

The absorbent article 250 may also include an elastic waist feature 299 shown in FIG. 13B in the form of a waist band and may provide improved fit and waste containment. The elastic waist feature 299 may be configured to elastically expand and contract to dynamically fit the wearer's waist. The elastic waist feature 299 can be incorporated into the diaper and may extend at least longitudinally outwardly from the absorbent core 292 and generally form at least a portion of the first and/or second outer edges 278, 280 of the diaper 252. In addition, the elastic waist feature may extend laterally to include the ears. While the elastic waist feature 299 or any constituent elements thereof may comprise one or more separate elements affixed to the diaper, the elastic waist feature may be constructed as an extension of other elements of the diaper, such as the backsheet 290, the topsheet 288, or both the backsheet and the topsheet. In addition, the elastic waist feature 299 may be disposed on the outer, garment-facing surface 284 of the chassis 254; the inner, body-facing surface 282; or between the inner and outer facing surfaces. The elastic waist feature 299 may be constructed in a number of different configurations including those described in U.S. Patent Publication Nos. 2007/0142806 A1; 2007/0142798 A1; and 2007/0287983 A1, all of which are hereby incorporated by reference herein.

As shown in FIGS. 13A-13B, the diaper 252 may include leg cuffs 296 that may provide improved containment of liquids and other body exudates. In particular, elastic gasketing leg cuffs can provide a sealing effect around the wearer's thighs to prevent leakage. It is to be appreciated that when the diaper is worn, the leg cuffs may be placed in contact with the wearer's thighs, and the extent of that contact and contact pressure may be determined in part by the orientation of diaper on the body of the wearer. The leg cuffs 296 may be disposed in various ways on the diaper 252.

The diaper 252 may be provided in the form of a pant-type diaper or may alternatively be provided with a re-closable fastening system, which may include fastener elements in various locations to help secure the diaper in position on the wearer. For example, fastener elements 298 may be located on the ears and may be adapted to releasably connect with one or more corresponding fastening elements located in the first or second waist regions. For example, as shown in FIG. 13A, the diaper 252 may include a connection zone 282, sometimes referred to as a landing zone, in the first waist region 268. It is to be appreciated that various types of fastening elements may be used with the diaper.

Test Methods
Bond Dimension Test Method

The Bond Dimension Test is used to measure bond density of the laminate in the various bonding regions. For purposes of this method, a bond is the intentional joining of two or more layers and is the deformed area caused during the bonding process (e.g., the reduced caliper at the site of bonding). It is recognized that in some cases, the deformed area may include one or more apertures.

Specimen Collection
1. Uniform pattern regions: To measure bond density of the bonding region having a uniform pattern, a square specimen of 1 cm$^2$ area is cut from the patterned bonded region of the laminate. Care should be taken to avoid collecting specimen from an adjacent region, if it is different. If specimen collection size of 1 cm$^2$ square is larger than the bonding region, the specimen is collected in the rectangle shape having a 1 cm$^2$ area: the shorter dimension of the bonding region forms one side of the rectangle and the other is selected such a way that rectangle area is 1 cm$^2$.
2. Other regions: To measure bond density of a bonding region without a uniform pattern, identify the plurality of bonds of interest and outline the resulting periphery. The specimen is collected by cutting along the periphery.

Bond Frequency: Bond density by bond frequency is calculated by counting number of bonds on the specimen and dividing the number of bonds by the area of the specimen. To the extent that specimen collection creates a partial bond within the specimen area, the partial bond is counted as a fraction equal to the fraction of the area of the bond included within the specimen relative to the area of the whole bond (i.e., the bond prior to cutting the specimen). Bond dimensions are measured to accuracy of 0.01 mm using a microscope and/or imaging software. The dimensions for each bond are used to calculate the bond area as per the mathematical formula for the shape of the bond. A total of five specimens are used, and an average bond density by bond frequency is calculated.

Aggregate Bond Coverage: Bond density by aggregate bond coverage is calculated by summing the bond areas for each bond in the specimen and dividing the sum of the bond areas by the area of the specimen. Bond dimensions are measured to accuracy of 0.01 mm using a microscope and/or imaging software. The dimensions for each bond are used to calculate the bond area as per the mathematical formula for the shape of the bond. The areas of partial bonds inside the specimen are also measured. All bond areas within the specimen are added to calculate aggregate bond area for the specimen and then the aggregate bond area is divided by the area of the specimen to determine aggregate bond coverage. A total of five specimen are used and an average bond density by aggregate bond coverage is calculated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling elastic laminates, the method comprising steps of:
   providing a first substrate and a second substrate, the first substrate and the second substrate each comprising a first surface and an opposing second surface, a first longitudinal edge and a second longitudinal edge separated from the first longitudinal edge to define a width in a cross direction;
   providing a first elastic film and a second elastic film, each of the first elastic film and the second elastic film comprising a stretched central region;
   positioning the stretched central region of the first elastic film in contact with the second surface of the first substrate;
   positioning the stretched central region of the second elastic film in contact with the second surface of the first substrate;
   forming an elastic laminate by advancing the second substrate in a machine direction to position the first surface of the second substrate in contact with the stretched central regions of the first and second elastic films, wherein the elastic laminate comprises a first bonding region and a second bonding region, wherein the first bonding region is defined where the stretched central region of the first elastic film is in direct contact with the second surface of the first substrate and the first surface of the second substrate, and wherein the second bonding region is positioned completely outside the first bonding region;

applying a first plurality of ultrasonic bonds to the elastic laminate to define a first bond density in the first bonding region; and applying a second plurality of ultrasonic bonds to the elastic laminate to define a second bond density in the second bonding region, wherein the first bond density is not equal to the second bond density and wherein the elastic laminate comprises at least one more layer in the second bonding region than in the first bonding region.

2. The method of claim 1 wherein the at least one more layer comprises a reinforcement layer.

3. The method of claim 1 wherein the at least one more layer comprises a folded portion of the first substrate, wherein the first longitudinal edge of the first substrate is positioned between an edge region of the first elastic material and the second surface of the first substrate.

4. The method of claim 1 further comprising the step of: cutting the elastic laminate along the machine direction between the first elastic film and the second elastic film into a first elastic laminate and a second elastic laminate.

5. The method of claim 4 wherein the step of cutting the elastic laminate further comprises cutting through the second bonding region.

6. The method of claim 1 wherein the second bonding region at least partially overlaps an unstretched edge region of the first elastic film.

7. The method of claim 1 wherein the second bonding region at least partially overlaps an unstretched edge region of the second elastic film.

8. The method of claim 1, wherein the step of providing a first elastic film and a second elastic film further comprises stretching a central region of the first elastic film in the cross direction and stretching the central region of the second elastic film in the cross direction.

9. The method of claim 1, further comprising steps of:
stretching a central region of an elastic film in the cross direction;
positioning the stretched central region of the elastic film in contact with the first substrate; and
cutting the stretched central region of the elastic film along the machine direction into the first elastic film and the second elastic film.

10. A method for assembling elastic laminates, the method comprising steps of:
providing a first substrate and a second substrate, the first substrate and the second substrate each comprising a first surface and an opposing second surface, a first longitudinal edge and a second longitudinal edge separated from the first longitudinal edge to define a width in a cross direction;

providing a first elastic film and a second elastic film, each of the first elastic film and the second elastic film comprising a stretched central region;

positioning the stretched central region of the first elastic film in contact with the second surface of the first substrate;

positioning the stretched central region of the second elastic film in contact with the second surface of the first substrate;

forming an elastic laminate by advancing the second substrate in a machine direction to position the first surface of the second substrate in contact with the stretched central regions of the first and second elastic films, wherein the elastic laminate comprises a first bonding region and a second bonding region, wherein the first bonding region is defined where the stretched central region of the first elastic film is in direct contact with the second surface of the first substrate and the first surface of the second substrate, and wherein the second bonding region is positioned completely outside the first bonding region;

applying a first plurality of ultrasonic bonds to the elastic laminate to define a first bond density in the first bonding region; and applying a second plurality of ultrasonic bonds to the elastic laminate to define a second bond density in the second bonding region, wherein the first bond density is not equal to the second bond density, or wherein the first bond density is equal to the second bond density and wherein at least one of the first plurality of ultrasonic bonds comprises a shape that is different from a shape of at least one of the second plurality of ultrasonic bonds.

11. The method of claim 10 further comprising the step of: cutting the elastic laminate along the machine direction between the first elastic film and the second elastic film into a first elastic laminate and a second elastic laminate.

12. The method of claim 11, wherein the step of cutting the elastic laminate further comprises cutting through the second bonding region.

13. The method of claim 10, wherein first bond density is defined by a first bond frequency and the second bond density is defined by a second bond frequency.

14. The method of claim 10, wherein first bond density is defined by a first aggregate bond coverage and the second bond density is defined by a second aggregate bond coverage.

15. The method of claim 10, wherein the first bond density is less than the second bond density.

16. The method of claim 10, wherein the step of forming an elastic laminate further comprises positioning the first substrate in direct contact with the second substrate, and wherein the second bonding region is defined where the first substrate is in direct contact with the second substrate.

* * * * *